US006833372B2

(12) United States Patent
Christie et al.

(10) Patent No.: US 6,833,372 B2
(45) Date of Patent: Dec. 21, 2004

(54) NON-PEPTIDE GNRH AGENTS, PHARMACEUTICAL COMPOSITIONS, AND METHODS FOR THEIR USE

(75) Inventors: Lance C. Christie, Vista, CA (US); Mark B. Anderson, Orinda, CA (US); Jun Feng, Carlsbad, CA (US); Yufeng Hong, San Diego, CA (US); Ved P. Pathak, San Diego, CA (US); Ranjan J. Rajapakse, Poway, CA (US); Eileen V. Tompkins, Escondido, CA (US); Haresh Vazir, Salinas, CA (US); Haitao Li, San Diego, CA (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/364,193

(22) Filed: Feb. 11, 2003

(65) Prior Publication Data

US 2004/0053951 A1 Mar. 18, 2004

Related U.S. Application Data

(60) Provisional application No. 60/356,561, filed on Feb. 12, 2002.

(51) Int. Cl.[7] ..................... A61K 31/505; C07D 239/46
(52) U.S. Cl. ................. 514/269; 514/235.8; 514/252.5; 514/270; 514/272; 514/274; 544/123; 544/295; 544/299; 544/300; 544/301; 544/302; 544/304
(58) Field of Search .............................. 544/299, 300, 544/301, 302, 321, 123, 295; 514/269, 270, 272, 274, 235.8, 252.5

(56) References Cited

U.S. PATENT DOCUMENTS 5,981,521 A   11/1999   Haviv et al.

FOREIGN PATENT DOCUMENTS

| WO | WO 93/03058 | 2/1993 |
|---|---|---|
| WO | WO 96/34012 | 10/1996 |
| WO | WO 96/38438 | 12/1996 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 99/44987 | 9/1999 |
| WO | WO 99/50276 | 10/1999 |
| WO | WO 00/04013 | 1/2000 |
| WO | WO 00/12521 | 3/2000 |
| WO | WO 00/12522 | 3/2000 |
| WO | WO 00/20358 | 4/2000 |
| WO | WO 00/68959 | 11/2000 |
| WO | WO 01/29044 | 4/2001 |

OTHER PUBLICATIONS

Abdel–Magid, et al., "Reductive Amination of Aldehydes and Ketones with Sodium Triacetoxyborohydride. Studies on Direct and Indirect Reductive Amination Procedures[1ʺ]", J. Org. Chem., 1996, p. 3849–3862, vol. 61.

Bagshawe, "Anti–Body Directed Enzyme Prodrug Therapy: A Review", Drug, Dev. Res., 1995, pp. 220–230, vol. 34.

Bertolini, et al., "A New Rational Hypothesis for the Pharmacophore of the Active Metabolite of Leflunomide, a Potent Immunosuppressive Drug", J. Med. Chem. 1997, pp. 2011–2016, vol. 40.

Bodor, "Novel Approaches to the Design of Safer Drugs: Soft Drugs and Site–Specific Chemical Delivery Systems", Advances in Drug Res., 1984, pp. 224–231, vol. 13.

Bowers, et al., "On the Inhibitory Effects of Luteinizing Hormone–Releasing Hormone Analogs", Endocrinology, 1980, pp. 674–683, vol. 106. (in vitro).

Bundgaard, Design of Prodrugs, (1985, Elsevier Press; Amsterdam—New York—Oxford).

Chapman, et al., "Synthesis of NN–Dialkyl–N'–arylalkyl–N'–4–quinazolyl(or 6–methyl–4–pyrimidyl or 4–methyl–2pyrimidyl)ethylenediamines of Potential Pharmacological Interest", J. Chem. Soc., 1961, pp. 1908–1918.

Cheng, et al., "Relationship Between the Inhibition Constant ($K_1$) and the Concentration of Inhibitor Which Causes 50 Per Cent Inhibition ($I_{50}$) of an Enzymatic Reaction*", Biochemical Pharmacol., 1973, pp. 3099–3108, vol. 22.

Cho, et al., "Discovery of a Novel, Potent, and Orally Active Nonpeptide Antagonist of the Human Luteinizing Hormone–Releasing Hormone (LHRH) Receptor", J. Med. Chem., 1998, p. 4190–4195, vol. 41(22).

Corbin, et al., "Inhibition of the Pre–Ovulatory Proestrous Gonadotropin Surge, Ovulation and Pregnancy with a Peptide Analogue of Luteinizing Hormone Releasing Hormone", Endocr. Res. Commun., 1975, pp. 1–23, vol. 2.

Dear, et al., "Mass Directed Peak Selection, an Efficient Method of Drug Metabolite Identification Using Directly Coupled Liquid Chromatography—Mass Spectrometry—Nuclear Magnetic Resonance Spectroscopy", J. Chromatogr. B, 2000, pp. 281–293, vol. 748.

Goetz, "Research Letters: Decreased Recovery of CD4 Lymphocytes in Older HIV–infected Patients Beginning Highly Active Antiretroviral Therapy", AIDS, 2001, pp. 1576–1578, vol. 15.

Harms, et al., "A Rapid and Simple Procedure for Chronic Cannulation of the Rat Jugular Vein", Applied Physiol., 1974, pp. 391–392, vol. 36.

(List continued on next page.)

Primary Examiner—Richard L. Raymond
(74) Attorney, Agent, or Firm—Keith D. Hutchinson; Bryan C. Zielinski; Peter C. Richardson

(57) ABSTRACT

Non-peptide GnRH agents that inhibit the effect of gonadotropin-releasing hormone are described. Such agents are useful for treating mammalian reproductive disorders and steroid hormone-dependent tumors as well as for regulating fertility, where suppression of gonadotropin release is indicated.

15 Claims, No Drawings

OTHER PUBLICATIONS

Harnden, et al. "Synthesis of Compounds with Potential Central Nervous System Stimulant Activity. II. 5–Spiro–Substituted 2–Amino–2–oxazolines", *J. Med. Chem.,* 1970, pp. 305–308.

Jungwirth, et al., "Luteinizing Hormone–Releasing Hormone Antagonist Cetrorelix (SB–75) and Bombesin Antagonist RC–3940–II Inhibit the Growth of Androgen–Independent PC–3 Prosate Cancer in Nude Mice", *Prostate,* 1997, pp. 164–172, vol. 32(3).

Koppan, et al., "Targeted Cytotoxic Analog of Luteinizing Hormone–Releasing Hormone AN–207 Inhibits the Growth of PC–82 Human Prostate Cancer in Nude Mice", *Prostate,* 1999, p. 151–158, vol. 38(2).

Kottler, et al., "The Genes for Gonadotropin–Releasing Hormone and Its Receptor are Expressed in Human Breast with Fibrocystic Disease and Cancer", *Int. J. Cancer,* 1997, pp. 595–599, vol. 71(4).

Larsen, "Design and Application of Prodrugs", *Drug Design and Development,* (1991, Krogsgaard–Larsen et al eds., Harwood Academic Publishers).

Montagnani, et al., "Effects of LHRH Agonists on the Growth of Human Prostatic Tumor Cells: 'in vitro' and 'in vivo' Studies", *Arch. Ital. Urol. Androl.,* 1997, pp. 257–263, vol. 69(4).

Nagy, et al., "Stability of Cytotoxic Luteinizing Hormone–Releasing Hormone Conjugate (AN–152) Containing Doxorubicin 14–O–Hemiglutarate in Mouse and Human Serum in Vitro: Implications for the Design of Preclinical Studies", *Proc Natl Acad Sci USA,* 2000, pp. 829–834, vol. 97(2).

Norwood Abbey press release dated Mar. 5, 2001, "Norwood Abbey Announces Breakthrough In Immunology".

Prox, et al., "Rapid Structure Elucidation of Drug Metabolites by Use of Stable Isotopes", *Xenobiol.,* 1992, pp. 103–112, vol. 3(2).

Scriabine, "Methode de Preparation des ω–aminopentanols et des Piperidines Substituees a L'azote (8)", *Bull. Soc. Chim. Fr.,* 1947, p. 454–456, vol. 14.

Shan, et al., "Prodrug Strategies Based on Intramolecular Cyclization Reactions", *J. Pharm. Sci.,* 1997, pp. 765–767, vol. 86(7).

Singh, "Rearrangement of β–Ionone to 1,1,6–Trimethyltetralin", *Indian J. Chem. Sect. B,* 1984, 23B(1), pp. 87–88.

Spraul, et al., "Liquid Chromatography Coupled with High–Field Proton NMR for Profiling *Human Urine for Endogenous Compounds and Drug Metabolites*", *J. Pharmaceutical & Biomedical Analysis,* 1992, pp. 601–605, vol. 10(8).

Srkalovic, et al., "Presence and Characteristics of Receptors for [D–Trp $^6$] Luteinizing Hormone Releasing Hormone and Epidermal Growth Factor in Human Ovarian Cancer", *Int. J. Oncol.,* 1998, pp. 489–498, vol. 12(3).

Still, et al., "Rapid Chromatographic Technique for Preparative Separations with Moderate Resolution", A.J. Org. Chem., 1978, p. 2923, vol. 43.

Walsh, et al., "Potent Antagonists of Gonadotropin Releasing Hormone Receptors Derived from Quinolone–6–Carboxamides", *Bioorg & Med Chem Ltrs.,* 2000, pp. 443–447, vol. 10.

NON-PEPTIDE GNRH AGENTS, PHARMACEUTICAL COMPOSITIONS, AND METHODS FOR THEIR USE

CROSS-REFERENCE TO RELATED APPLICATIONS

This application claims priority from and incorporates by reference in its entirety pending prior U.S. application Ser. No. 60/356,561, filed Feb. 12, 2002.

TECHNICAL FIELD AND INDUSTRIAL APPLICABILITY OF THE INVENTION

This invention relates generally to compounds that affect the action of human gonadotropin-releasing hormone (GnRH). More particularly, it relates to certain non-peptide GnRH antagonists or agonists and to their preparation. These non-peptide GnRH agents have advantageous physical, chemical, and biological properties, and are useful medicaments for diseases or conditions mediated by modulation of the pituitary-gonadal axis. The invention also relates to methods for treating individuals needing therapeutic regulation of GnRH—i.e., methods for treating diseases and conditions mediated by GnRH regulation—involving the administration of such GnRH agents.

BACKGROUND OF THE INVENTION

Gonadotropin-Releasing Hormone (GnRH), also known as luteinizing hormone-releasing hormone (LH-RH), plays a central role in the biology of reproduction. Various analogs have been used for an increasing number of clinical indications. The GnRH decapeptide (pyro-Glu-His-Trp-Ser-Tyr-Gly-Leu-Arg-Pro-Gly-NH$_2$ or p-EHWSYGLRPG-NH$_2$) is produced in neurons of the medial basal hypothalamus from a larger precursor by enzymatic processing. The decapeptide is released in a pulsatile manner into the pituitary portal circulation system where GnRH interacts with high-affinity receptors (7-Transmembrane G-Protein Coupled Receptors) in the anterior pituitary gland located at the base of the brain. In the pituitary, GnRH triggers the release of two gonadotropic hormones (gonadotropins): luteinizing hormone (LH) and follicle-stimulating hormone (FSH). In testes and ovaries, LH stimulates the production of testosterone and estradiol, respectively. FSH stimulates follicle growth in women and sperm formation in men. When correctly functioning, the pulse-timed release and concentration levels of GnRH are critical for the maintenance of gonadal steroidogenesis and for normal functions of reproduction related to growth and sexual development.

The pituitary response to GnRH varies greatly throughout life. GnRH and the, gonadotropins first appear in the fetus at about ten weeks of gestation. The sensitivity to GnRH declines, after a brief rise during the first three months after birth, until the onset of puberty. Before puberty, the FSH response to GnRH is greater than that of LH. Once puberty begins, sensitivity to GnRH increases, and pulsatile LH secretion ensues. Later in puberty and throughout the reproductive years, pulsatile release of GnRH occurs throughout the day, with LH responsiveness being greater than that of FSH. Pulsatile GnRH release results in pulsatile LH and FSH release from the pituitary and, hence, testosterone and estradiol release from the gonads. After menopause, FSH and LH-concentrations rise, and post-menopausal FSH levels are higher than those of LH.

Chronic administration of GnRH agonists and antagonists to animals or to man results in decreased circulating levels of both LH and FSH. GnRH agonists are compounds that mimic endogenous GnRH to stimulate receptors on the pituitary gland, resulting in release of LH and FSH. After a transient rise in gonadal hormone production or "flare" response, chronic administration of GnRH agonists results in a down-regulation of GnRH receptors. GnRH receptor down-regulation and desensitization of the pituitary results in a decrease of circulating levels of LH and FSH. In spite of the symptom-exacerbating hormonal flare experienced, GnRH agonists have been the treatment of choice for sex-steroid-dependent pathophysiologies. For example GnRH agonists have been used to reduce testosterone production, thereby reducing prostate volume in benign prostatic hyperplasia (BPH) and slowing tumor growth in prostate cancer. These compounds have also been used to treat breast and ovarian cancers.

Recently, GnRH antagonists have become available for clinical evaluation GnRH antagonists have an immediate effect on the pituitary without the observed flare associated with agonists. Use of GnRH antagonists (e.g., decapeptides) has been reported in the literature for treatment of breast, ovarian, and prostatic cancers. Other uses of antagonists, like agonists, include endometriosis (including endometriosis with pain), uterine myoma, ovarian and mammary cystic diseases (including polycystic ovarian disease), prostatic hypertrophy, amenorrhea (e.g., secondary amenorrhea), uterine fibroids, and precocious puberty. These agents may also be useful in the symptomatic relief of premenstrual syndrome (PMS), pregnancy regulation, infertility remedy, or menstruation regulation. Furthermore, antagonists may be useful to regulate the secretion of gonadotropins in male mammals to arrest spermatogenesis (e.g., as male contraceptives), and for treatment of male sex offenders. Importantly, GnRH antagonists (and agonists) have found utility in treatments where a reversible suppression of the pituitary-gonadal axis is desired and in the treatment of sleep disorders (e.g., apnea.)

For over fifty years, androgen deprivation has been the most effective systematic therapy for the treatment of metastatic carcinoma of the prostate. The rationale is simple—the prostate gland requires androgens for proper growth, maintenance, and function. Yet, prostate cancer and benign prostate hyperplasia are common in men and develop in an environment of continuous androgen exposure. Thus, utilizing a GnRH antagonist to interrupt the pituitary-gonadal axis reduces androgen production and results in tumor growth modulation. Furthermore, GnRH antagonists may have a direct effect on tumor growth by blocking receptors on the tumor cells. For those cancer types that respond both to sex hormones and to GnRH directly, antagonists should be effective in slowing tumor growth by these two mechanisms. Since GnRH receptors are present on many prostate and breast cancer cells, it has recently been speculated that GnRH antagonists may also be effective in treating non-hormone-dependent tumors. Recent literature examples indicate that GnRH receptors are present on a number of cancer cell lines, including:

prostate cancer: GnRH agonists exert both in vitro, and in vivo, a direct inhibitory action on the growth of both androgen-dependent (LNCaP) and androgen-independent (DU 145) human prostatic cancer cell lines [Montagnani et al., *Arch. Ital. Urol. Androl.*, 69(4), 257–263 (1997); Jungwirth et al., "GnRH Antagonist Inhibit the Growth of Androgen-Independent PC-3 Prostate Cancer in Nude Mice," *Prostate*, 32(3), 164–172 (1997)];

ovarian cancer: The demonstration of GnRH receptors in human ovarian cancers provides a rationale for the use of therapeutic approaches based on GnRH analogues in this malignancy [Srkalovic et al., *Int. J. Oncol.*, 12(3), 489–498 (1998)].

breast cancer: Breast cancer is the most common type of cancer in women over the age of forty and is the leading cause of cancer-related death in women. Systematic endocrine intervention represents a major treatment option for the management of advanced breast cancer, especially with estrogen-dependent cancers. The genes for gonadotropin-releasing hormone and its receptor are expressed in human breast with fibrocystic disease and cancer [Kottler et al., *Int. J. Cancer*, 71(4), 595–599 (1997)].

GnRH agents may also be useful in treating cancer through generation of thymus re-growth and therefore induction of the development of new T-cells. See Norwood Abbey press release dated Mar. 5, 2001, "Norwood Abbey Announces Breakthrough In Immunology." These white blood cells, which develop in the thymus gland, are a fundamental component of the immune system's involvement in a range of diseases, including viral infections, transplant organ rejection, cancer, and autoimmune diseases. Thus, for example, since the human immunodeficiency virus (HIV) preferentially infects and destroys T-cells, GnRH agents may be useful for treating HIV infection or acquired immune deficiency syndrome (AIDS). Additionally, GnRH agents may be useful in combating infection in tissue-transplant patients where immunosuppressive drugs, which remove T-cells, are being administered to counteract rejection of the transplanted tissue. Similarly, since adequate and effective T-cells help defend against cancer, and chemotherapy and radiation regimens detrimentally impact T-cells, GnRH agents may be useful in conjunction with a chemotherapeutic agent or radiation regimen in treating cancer. Furthermore, GnRH agents may be useful for treating autoimmune diseases such as multiple sclerosis (MS), where T-cells are produced that react against a molecule surrounding nerve cells. GnRH agents may also benefit patients who have been shown to have a decreased likelihood of immune recovery with HAART. See *AIDS*. 2001; 15:1576–1578.

Heretofore, available GnRH antagonists have included peptide analogs of GnRH. See, e.g., International Publication Nos. WO 93/03058, WO 99/50276, WO 00/12521, and WO 00/12522; Koppan et al., Prostate, 38(2), 151–158 (1999); and Nagy et al., *Proc Natl Acad Sci USA*, 97(2), 829–834 (2000). Though peptide antagonists of peptide hormones are often quite potent, the use of peptide antagonists is typically associated with problems because peptides are degraded by physiological enzymes and often poorly distributed within the organism being treated.

A non-peptide antagonist of the human leuteinizing hormone-releasing hormone (LHRH) receptor was reported by Cho et al. (*J Med Chem*, 41(22), 4190 (1998)). Other non-peptide GnRH antagonists have been reported in the literature. For example, certain quinolone-6-carboxamides were reported by Walsh et al. in *Bioorg & Med Chem Ltrs.*, 10, 443–447 (2000). Certain tricyclic diazepines and cyclic pentapeptides were reported in International Publication Nos. WO 96/38438 and WO 96/34012, respectively. Certain tetrahydroisoquinoline derivatives were reported in U.S. Pat. No. 5,981,521. For additional examples of non-peptide GnRH antagonists, see International Publication Nos. WO 97/21435, WO 97/21703, WO 97/21704, WO 97/21707, WO 99/44987, WO 00/04013, WO 00/12522, WO 00/12521, WO 00/04013, WO 00/68959, and WO 01/29044. Additionally, active non-peptide GnRH agents are described in International Publication No. WO 00/20358.

Despite recent advances, there continues to be a need for potent non-peptide antagonists of the peptide hormone GnRH with desirable pharmacokinetic and pharmacological properties. For example, there is a desire for non-peptide GnRH agents having advantageous physical, chemical and biological properties, which are useful medicaments for treating diseases mediated via the pituitary-gonadal axis and by directly targeting the receptor on tumor cells. Furthermore, there is a need for non-peptide GnRH agents having a desirable combination of activity, solubility, and ADME (absorption, distribution, metabolism, excretion) properties. There is also a need for GnRH agents that act upon receptors to treat both hormone-dependent and hormone-independent cancers.

SUMMARY OF THE INVENTION

In one general aspect, the invention is directed to compounds represented by the following Formula I:

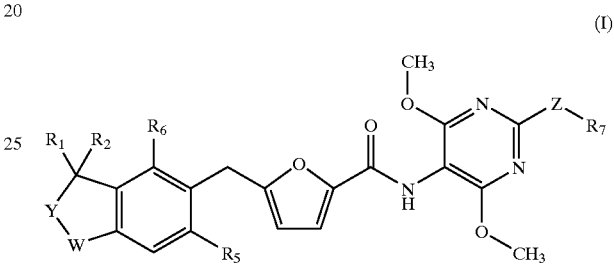

wherein:

Y is O or $(CH_2)_n$ where n is 1 or 2;

$R_1$ and $R_2$ are each independently: hydrogen; =O; or a halogen; or an alkyl, alkenyl, heteroalkyl, haloalkyl, alkynyl, aryl, cycloalkyl, heterocycloalkyl, or heteroaryl group unsubstituted or substituted with one or more substituents independently selected from the group consisting of: halogens; =O; =S; —CN; and —$NO_2$; and alkyl, alkenyl, heteroalkyl, haloalkyl, alkynyl, aryl, cycloalkyl, heterocycloalkyl, heteroaryl, —$(CH_2)_2)_z$CN where z is an integer from 0 to 4, =NH, —NHOH, —OH, —C(O)H, —OC(O)H, —C(O)OH, —OC(O)OH, —OC(O)OC(O)H, —OOH, —C(NH)$NH_2$, —NHC(NH)$NH_2$, —C(S)$NH_2$, —NHC(S)$NH_2$, —NHC(O)$NH_2$, —S($O_2$)H, —S(O)H, —$NH_2$, —C(O)$NH_2$, —OC(O)$NH_2$, —NHC(O)H, —NHC(O)OH, —C(O)NHC(O)H, —OS($O_2$)H, —S(O)H, —OSH, —SC(O)H, —S(O)C(O)OH, —$SO_2$C(O)OH, —NHSH, —NHS(O)H, —$NHO_2$H, —C(O)SH, —C(O)S(O)H, —C(O)S($O_2$)H, —C(S)OH, —C(SO)OH, —C($SO_2$)OH, —NHC(S)H, —OC(S)OH, —OC($SO_2$)H, —S($O_2$)$NH_2$, —S(O)$NH_2$, —$SNH_2$, —NHCS($O_2$)H, —NHC(SO)H, —NHC(S)H, and —SH groups unsubstituted or substituted with one or more substituents independently selected from the group consisting of halogens, =O, —$NO_2$, —CN, —$(CH_2)_z$—CN where z is an integer from 0 to 4, —$OR_c$, —$NR_cOR_c$, —$NR_cR_c$, —C(O)$NR_c$, —C(O)$OR_c$, —C(O)$R_c$, —$NR_cC(O)NR_cR_c$, —$NR_cC(O)R_c$, —OC(O)$OR_c$, —OC(O)$NR_cR_c$, —$SR_c$, unsubstituted alkyls, unsubstituted alkenyls, unsubstituted alkynyls, unsubstituied aryls, unsubstituted cycloalkyls, unsubstituted heterocycloalkyls, and unsubstituted heteroaryls, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group;

W is O or $C(R_3)(R_4)$, where $R_3$ and $R_4$ are each independently selected from the group consisting of hydrogen; =O; and halogens; and alkyl, alkenyl, heteroalkyl, haloalkyl, alkynyl, aryl, cycloalkyl, heterocycloalkyl, and heteroaryl groups unsubstituted or substituted with one or more substituents selected from the group consisting of: halogens; =O; =S; —CN; and —$NO_2$; and alkyl, alkenyl, heteroalkyl, haloalkyl, alkynyl, aryl, cycloalkyl, heterocycloalkyl, heteroaryl, —$(CH_2)_z CN$ where z is an integer from 0 to 4, =NH, —NHOH, —OH, —C(O)H, —OC(O)H, —C(O)OH, —OC(O)OH, —OC(O)OC(O)H, —OOH, —C(NH)$NH_2$, —NHC(NH)$NH_2$, —C(S)$NH_2$, —NHC(S)$NH_2$, —NHC(O)$NH_2$, —S($O_2$)H, —S(O)H, —$NH_2$, —C(O)$NH_2$, —OC(O)$NH_2$, —NHC(O)H, —NHC(O)OH, —C(O)NHC(O)H, —OS($O_2$)H, —OS(O)H, —OSH, —SC(O)H, —S(O)C(O)OH, —$SO_2$C(O)OH, —NHSH, —NHS(O)H, —$NHSO_2$H, —C(O)SH, —C(O)S(O)H, —C(O)S($O_2$)H, —C(S)H, —C(S)OH, —C(SO)OH, —C($SO_2$)OH, —NHC(S)H, —OC(S)H, —OC(S)OH, —OC($SO_2$)H, —S($O_2$)$NH_2$, —S(O)$NH_2$, —$SNH_2$, —NHCS($O_2$)H, —NHC(SO)H, —NHC(S)H, and —SH groups unsubstituted or substituted with one or more substituents selected from the group consisting of halogens, =O, —$NO_2$, —CN, —($CH_2$), —CN where z is an integer from 0 to 4, —$OR_c$, —$NR_c OR_c$, —$NR_c R_c$, —C(O)$R_c$, —C(O)$OR_c$, —C(O)$R_c$, —$NR_c C(O)NR_c R_c$, —$NR_c C(O)R_c$, —OC(O)$OR_c$, —OC(O)$NR_c R_c$, —$SR_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group;

$R_5$ is hydrogen, halogen, unsubstituted $C_1$–$C_3$ alkyl, or unsubstituted $C_1$–$C_3$ heteroalkyl;

$R_6$ is hydrogen, halogen, unsubstituted $C_1$–$C_3$ alkyl, or unsubstituted $C_1$–$C_3$ heteroalkyl;

Z is O or $NR_x$, where $R_x$ is hydrogen, unsubstituted alkyl, or unsubstituted heteroalkyl; and $R_7$ is hydrogen; a halogen; or an alkyl, alkenyl, heteroalkyl, haloalkyl, alkynyl, aryl, cycloalkyl, heterocycloalkyl, or heteroaryl group unsubstituted or substituted with one or more substituents selected from the group consisting of: halogens; =O—S; —CN; and —$NO_2$; and alkyl, alkenyl, heteroalkyl, haloalkyl, alkynyl, aryl, cycloalkyl, heterocycloalkyl, heteroaryl, —$(CH_2)_z CN$ where z is an integer from 0 to 4, =NH, —NHOH, —OH, —C(O)H, —OC(O)H, —C(O)OH, —OC(O)OH, —OC(O)OC(O)H, —OOH, —C(NH)$NH_2$, —NHC(NH)$NH_2$, —C(S)$NH_2$, —NHC(S)$NH_2$, —NHC(O)$NH_2$, —S($O_2$)H, —S(O)H, —$NH_2$, —C(O)$NH_2$, —OC(O)$NH_2$, —NHC(O)H, —NHC(O)OH, —C(O)NHC(O)H, —OS($O_2$)H, —OS(O)H, —OSH, —SC(O)H, —S(O)C(O)OH, —$SO_2$C(O)OH, —NHSH, —NHS(O)H, —$NHSO_2$H, —C(O)SH, —C(O)S(O)H, —C(O)S($O_2$)H, —C(S)H, —C(S)OH, —C(SO)OH, —C($SO_2$)OH, —NHC(S)H, —OC(S)H, —OC(S)OH, —OC($SO_2$)H, —S($O_2$)$NH_2$, —S(O)$NH_2$, —$SNH_2$, —NHCS($O_2$)H, —NHC(SO)H, —NHC(S)H, and —SH groups unsubstituted or substituted with one or more substituents selected from the group consisting of halogens, =O, —$NO_2$, —CN, —($CH_2$), —CN where z is an integer from 0 to 4, —$OR_c$, —$NR_c OR_c$, —C(O)$OR_c$, —C(O)$NR_c$, —C(O) $OR_c$, —C(O)$R_c$, —$NR_c C(O)NR_c R$, —$NR_c C(O)R_c$, —OC(O)$OR_c$, —OC(O)$NR_c R_c$, —$SR_c$, unsubstituted alkyl, unsubstituted alkenyl, unsubstituted alkynyl, unsubstituted aryl, unsubstituted cycloalkyl, unsubstituted heterocycloaplkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substitute with an unsubstituted alkyl group;

or $R_7$ and $R_x$ cyclize to form a heterocycloalkyl or heteroaryl group unsubstituted or substituted with one or more substituents independently selected from the group consisting of =O; and halogens; and alkyl, alkenyl, heteroalkyl, haloalkyl, alkynyl, aryl, cycloalkyl, heterocycloalkyl, and heteroaryl groups unsubstituted or substituted with one or more substituents selected from the group consisting of: halogens, —O; —S; —CN; and —$NO_2$; and alkyl, alkenyl, heteroalkyl, haloalkyl, alkynyl, aryl, cycloalkyl, heterocycloalkyl, heteroaryl, —$(CH_2)_z CN$ where z is an integer from 0 to 4, —NH, —NHOH, —OH, —C(O)H, —OC(O)H, —C(O)OH, —OC(O)OH, —OC(O)OC(O)H, —OOH, —C(NH)$NH_2$, —NHC(NH)$NH_2$, —C(S)$NH_2$, —NHC(S)$NH_2$, —NHC(O)$NH_2$, —S($O_2$)H, —S(O)H, —$NH_2$, —C(O)$NH_2$, —OC(O)$NH_2$, —NHC(O)H, —NHC(O)OH, —C(O)NHC(O)H, —OS($O_2$)H, —OS(O)H, —OSH, —SC(O)H, —S(O)C(O)OH, —$SO_2$C(O)OH, —NHSH, —NHS(O)H, —$NHSO_2$H, —C(O)SH, —C(O)S(O)H, —C(O)S($O_2$)H, —C(S)H, —C(S)OH, —C(SO)OH, —C($SO_2$)OH, —NHC(S)H, —OC(S)H, —OC(S)OH, —OC($SO_2$)H, —S($O_2$)$NH_2$, —S(O)$NH_2$, —$SNH_2$, —NHCS($O_2$)H, —NHC(SO)H, —NHC(S)H, and —SH groups unsubstituted or substituted with one or more substituents selected from the group consisting of halogens, =O, —$NO_2$, —CN, —($CH_2$), —CN where z is an integer from 0 to 4, —$OR_c$, —$NR_c OR_c$, —$NR_c R_c$, —C(O)$NR_c$, —C(O)$OR_c$, —C(O)$R_c$, —$NR_c C(O)$ $NR_c R_c$, —$NR_c C(O)R_c$, —OC(O)$OR_c$, —OC(O)$NR_c R_c$, —$SR_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group.

In preferred embodiments of compounds of the formula I:

Y is O;

W is $C(R_3)(R_4)$, where $R_3$ and $R_4$ are each independently selected from the group consisting of hydrogen; and alkyl and heteroalkyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH) NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O) NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O) NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$), —CN where z is an integer from 0 to 4, —OR$_c$, —NR$_c$OR$_c$, —NR$_c$R$_c$, —C(O)NR$_c$, —C(O) OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group; and R$_1$ and R$_2$ are each independently hydrogen; or an alkyl or heteroalkyl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O) OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O) NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O) NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$), —CN where z is an integer from 0 to 4, —OR$_c$, —NR$_c$OR$_c$, —NR$_c$R$_c$, —C(O)NR$_c$, —C(O) OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group, and where at least one of R$_1$ or R$_2$ is not hydrogen;

R$_5$ is hydrogen, halogen, unsubstituted C$_1$–C$_3$ alkyl, or unsubstituted C$_1$–C$_3$ heteroalkyl;

R$_6$ is hydrogen, halogen, unsubstituted C$_1$–C$_3$ alkyl, or unsubstituted C$_1$–C$_3$ heteroalkyl;

Z is O or NR$_x$, where R$_x$ is hydrogen, unsubstituted alkyl, or unsubstituted heteroalkyl; and R$_7$ is an alkyl, alkenyl, heteroalkyl, or an alkynyl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)—H, —OOH, —C(NH)NH$_2$, —NHC (NH)NH$_2$, —C(S)NH$_2$, —NHC(S)NH$_2$, —NHC(O) NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$), —CN where z is an integer from 0 to 4—OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$; —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two-or more R$_c$ groups together cyclize to form part of a heteroaryl or heterocycloalkyl group unsubstituted or substituted with an unsubstituted alkyl group.

In other preferred embodiments:

Y is O;

W is C(R$_3$)(R$_4$), where R$_3$ and R$_4$ are each independently selected from the group consisting of hydrogen, unsubstituted alkyls, and unsubstituted heteroalkyls;

R$_1$ and R$_2$ are each independently hydrogen, unsubstituted alkyl, or unsubstituted heteroalkyl, and where at least one of R$_1$ or R$_2$ is not hydrogen;

R$_5$ is hydrogen, halogen, unsubstituted C$_1$–C$_3$ alkyl, or unsubstituted C$_1$–C$_3$ heteroalkyl;

R$_6$ is hydrogen, halogen, unsubstituted C$_1$–C$_3$ alkyl, or unsubstituted C$_1$–C$_3$ heteroalkyl;

Z is NH or O, and

R$_7$ is an alkyl, alkenyl, heteroalkyl, or an alkynyl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH₂, —NHC(NH)NH₂, —C(S)NH₂, —NHC(S)NH₂, —NHC(O)NH₂, —S(O₂)H, —S(O)H, —NH₂, —C(O)NH₂, —OC(O)NH₂, —NHC(O)H, —NHC(O)OH, —C(O)NHC(O)H, —OS(O₂)H, —OS(O)H, —OSH, —SC(O)H, —S(O)C(O)OH, —SO₂C(O)OH, —NHSH, —NHS(O)H, —NHSO₂H, —C(O)SH, —C(O)S(O)H, —C(O)S(O₂)H, —C(S)H, —C(S)OH, —C(SO)OH, —C(SO₂)OH, —NHC(S)H, —OC(S)H, —OC(S)OH, —OC(SO₂)H, —S(O₂)NH₂, —S(O)NH₂, —SNH₂, —NHCS(O₂)H, —NHC(SO)H, —NHC(S)H, and —SH groups unsubstituted or substituted with one or more substituents selected from the group consisting of halogens, =O, —NO₂, —CN, —(CH₂)ₓ—CN where z is an integer from 0 to 4, —OR_c, —NR_cOR_c, —NR_cR_c, —C(O)NR_c, —C(O)OR_c, —C(O)R_c, —NR_cC(O)NR_cR_c, —NR_cC(O)R_c, —OC(O)OR_c, —OC(O)NR_cR_c, —SR_c, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R_c is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R_c groups together cyclize to form part of a heteroaryl or heterocycloalkyl group unsubstituted or substituted with an unsubstituted alkyl group.

In another general aspect, the invention is directed to compounds represented by the following Formula II:

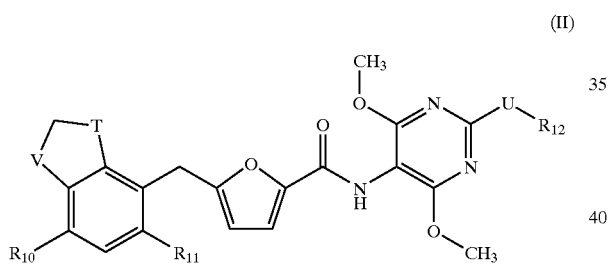

(II)

wherein:

T is O or (CH₂)ₙ, where n is 1 or 2;

V is O or C(R₈)(R₉), where R₈ and R₉ are each independently selected from the group consisting of hydrogen; =O; and halogens; and alkyl, alkenyl, heteroalkyl, haloalkyl, alkynyl, aryl, cycloalkyl, heterocycloalkyl, and heteroaryl groups unsubstituted or substituted with one or more substituents selected from the group consisting of: halogens; =O; =S; —CN; and —NO₂; and alkyl, alkenyl, heteroalkyl, haloalkyl, alkynyl, aryl, cycloalkyl, heterocycloalkyl, heteroaryl, —(CH₂)ₓCN where z is an integer from 0 to 4, =NH, —NHOH, —OH, —C(O)H, —OC(O)H, —C(O)OH, —OC(O)OH, —OC(O)OC(O)H, —OOH, —C(NH)NH₂, —NHC(NH)NH₂, —C(S)NH₂, —NHC(S)NH₂, —NHC(O)NH₂, —S(O₂)H, —S(O)H, —NH₂, —C(O)NH₂, —OC(O)NH₂, —NHC(O)H, —NHC(O)OH, —C(O)NHC(O)H, —OS(O₂)H, —OS(O)H, —OSH, —SC(O)H, —S(O)C(O)OH, —SO₂C(O)OH—, —NHSH, —NHS(O)H, —NHSO₂H, —C(O)SH, —C(O)S(O)H, —C(O)S(O₂)H, —C(S), —C(S)OH, —C(SO)OH, —C(SO₂)OH, —NHC(S)H, —OC(S)H, —OC(S)OH, —OC(O₂)NH₂; —S(O)NH₂, —SNH₂, —NHCS(O₂)H, —NHC(SO)H, —NHC(S)H, and —SH groups unsubstituted or substituted with one or more substituents selected from the group consisting of halogens, =O, —NO₂, —CN, —(CH₂), —CN where z is an integer from 0 to 4, —OR_c, —NR_cOR_c, —NR_cR_c, —C(O)NR_c, —C(O)OR_c, —C(O)R_c, —NR_cC(O)NR_c, —NR_cC(O)NR_c, —OC(O)OR_c, —OC(O)NR_cR_c, —SR_c, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R_c is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R_c groups together cyclize to form part of a heteroaryl or heterocycloalkyl group unsubstituted or substituted with an unsubstituted alkyl group;

R₁₀ is hydrogen, halogen, unsubstituted C₁–C₃ alkyl, or unsubstituted C₁–C₃ heteroalkyl;

R₁₁ is hydrogen, halogen, unsubstituted C₁–C₃ alkyl, or unsubstituted C₁–C₃ heteroalkyl;

R₁₂ is hydrogen or a halogen, or an alkyl, alkenyl, heteroalkyl, haloalkyl, alkynyl, aryl, cycloalkyl, heterocycloalkyl, or heteroaryl group unsubstituted or substituted with one or more substituents selected from the group consisting of: halogens; =O; =S; —CN; and NO₂; and alkyl, alkenyl, heteroalkyl, haloalkyl, alkynyl, aryl, cycloalkyl, heterocycloalkyl, heteroaryl, —(CH₂)ₓCN where z is an integer from 0 to 4, =NH, —NHOH, —OH, —C(O)H, —OC(O)H, —C(O)OH, —OC(O)OH, —OC(O)OC(O)H, —OOH, —C(NH)NH₂, —NHC(NH)NH₂, —C(S)NH₂, —NHC(S)NH₂, —NHC(O)NH₂, —S(O₂)H, —S(O)H, —NH₂, —C(O)NH₂, —OC(O)NH₂, —NHC(O)H, —NHC(O)OH, —C(O)NHC(O)H, —OS(O₂)H, —OS(O)H, —OSH, —SC(O)H, —S(O)C(O)OH, —SO₂C(O)OH, —NHSH, —NHS(O)H, —NHSO₂H, —C(O)SH, —C(O)S(O)H, —C(O)S(O₂)H, —C(S)H, —C(S)OH, —C(SO)OH, —C(SO₂)OH, —NHC(S)H, —OC(S)H, —OC(S)OH, —OC(SO₂)H, —S(O₂)NH₂, —S(O)NH₂, —SNH₂, —NHCS(O₂)H, —NHC(SO)H, —NHC(S)H, and —SH groups unsubstituted or substituted with one or more substituents selected from the group consisting of halogens, =O, —NO₂, —CN, —(CH₂)ₓ—CN where z is an integer from 0 to 4, —OR_c, —NR_cOR_c, —NR_cR_c, —C(O)NR_c, —C(O)OR_c, —C(O)R_c, —NR_cC(O)NR_cR_c, —NR_cC(O)R_c, —OC(O)OR_c, —OC(O)NR_cR_c, —SR_c, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R_c is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R_c groups together cyclize to form part of a heteroaryl or heterocycloalkyl group unsubstituted or substituted with an unsubstituted alkyl group; and U is O or NR_x, where R_x is hydrogen, alkyl, or heteroalkyl;

or R₁₂ and R_x cyclize to form a heterocycloalkyl unsubstituted or substituted with one or more substituents independently selected from the group consisting of halogens; =O; =S; —CN; and —NO₂; and alkyl, alkenyl, heteroalkyl, haloalkyl, alkynyl, aryl, cycloalkyl, heterocycloalkyl, heteroaryl, —(CH₂)ₓCN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group; or a pharmaceutically acceptable salt, pharmaceutically acceptable prodrug, or pharmaceutically active metabolite of said compound.

In preferred embodiments of formula II:

T is O;

V is C(R$_8$)(R$_9$), and R$_8$ and R$_9$ are each independently selected from the group consisting of hydrogen and alkyl, alkenyl, heteroalkyl, and alkynyl groups unsubstituted or substituted with one or more substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, —NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

R$_{10}$ is hydrogen, halogen, unsubstituted C$_1$–C$_3$ alkyl, or unsubstituted C$_1$–C$_3$ heteroalkyl;

R$_{11}$ is hydrogen, halogen, unsubstituted C$_1$–C$_3$ alkyl, or unsubstituted C$_1$–C$_3$ heteroalkyl;

U is NH or O; and

R$_{12}$ is an alkyl, alkenyl, heteroalkyl, or alkynyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$), —CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

More preferably, the invention is directed to compounds described in the examples herein and to pharmaceutically acceptable salts of such compounds.

In addition to compounds of formulae I and II, the invention is also directed to pharmaceutically acceptable salts, pharmaceutically acceptable prodrugs, and pharmaceutically active metabolites of such compounds, and pharmaceutically acceptable salts of such metabolites. Such compounds, salts, prodrugs and metabolites are at times collectively referred to herein as "GnRH agents."

The invention also relates to pharmaceutical compositions each comprising a therapeutically effective amount of a GnRH agent of the invention in combination with a pharmaceutically acceptable carrier or diluent.

Further, the invention is directed to therapeutic methods for treating a disease or condition mediated by regulating secretion of gonadotropins or suppressing the pituitary-gonadal axis in a mammal, comprising administering a therapeutically effective amount of a compound of formula I or II, or a salt, prodrug, or metabolite thereof. The invention is also directed to methods for antagonizing gonadotropin-releasing hormone in a patient subject suffering from a gonadotropin-releasing hormone derived disorder, comprising administering to the patient a therapeutically effective amount of a compound of formula I or II or a salt thereof. In one preferred embodiment, the method is for treating a disorder that is a sex hormone related condition, such as of endometriosis, polycystic ovarian disease, uterine fibroids, or precocious puberty. In another preferred embodiment, the method is for treating a sex hormone dependent cancer (such as prostatic cancer, uterine cancer, breast cancer, and pituitary gonadotrophe adenomas), benign prostatic hypertropy, amenorrhea syndrome, or myoma of the uterus. The invention is also directed to methods employing a compound of formula I or II, or a salt thereof, for treating premenstrual syndrome, regulating pregnancy, treating infertility, or regulating menstruation in a patient. Moreover, the invention is directed to methods for treating sleep apnea by administering a compound of formula I or II or a salt thereof.

Other aspects, features, and advantages of the invention will become apparent from the detailed description of the invention and its preferred embodiments.

DETAILED DESCRIPTION OF INVENTION AND PREFERRED EMBODIMENTS

As used herein, the terms "comprising" and "including" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by "/"), ethyl (Et), n-propyl, isopropyl, butyl, isobutyl, sec-butyl, tert-butyl (tBu), pentyl, isopentyl, tert-pentyl, hexyl, isohexyl, and the like.

The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary alkyl amines, alkyl sulfides, and the like.

The term "alkenyl" refers to a straight- or branched-chain alkenyl group having from 2 to 12 carbon atoms in the chain. Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. Illustrative alkynyl groups include prop-2-ynyl, but-2-ynyl, but-3-ynyl, 2-methylbut-2-ynyl, hex-2-ynyl, and the like.

The term "haloalkyl" refers to a straight- or branched-chain alkenyl group having from 2–12 carbon atoms in the chain and where one or more hydrogens is substituted with a halogen. Illustrative haloalkyl groups include trifluoromethyl, 2-bromopropyl, 3-chlorohexyl, 1-iodoisobutyl, and the like.

The term "aryl" (Ar) refers to a monocyclic, or fused or spiro polycyclic, aromatic carbocycle (ring structure having ring atoms that are all carbon) having from 3 to 12 ring atoms per ring. Illustrative examples of aryl groups include the following moieties:

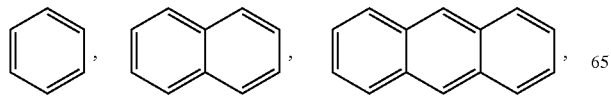

-continued

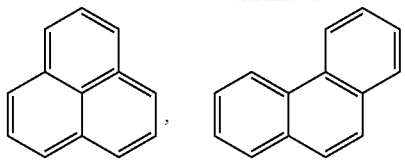

, and the like.

The term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

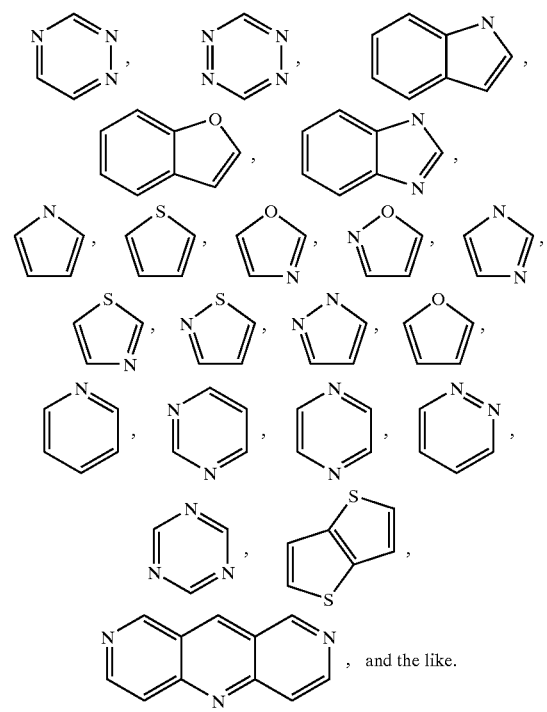

, and the like.

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

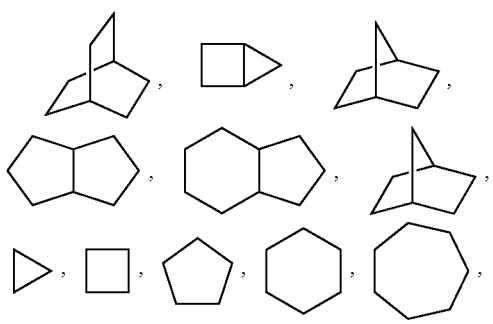

-continued

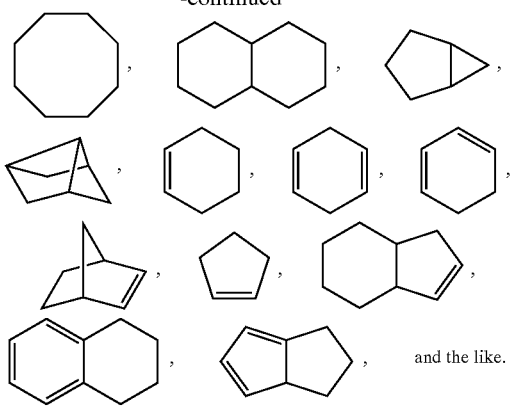

A "heterocycloalkyl" refers to a monocyclic, or fused or Spiro polycyclic, ring structure that is saturated or partially saturated and has from 3 to 12 ring atoms per ring selected from C atoms and N, O, and S heteroatoms. Illustrative examples of heterocycloalkyl groups include:

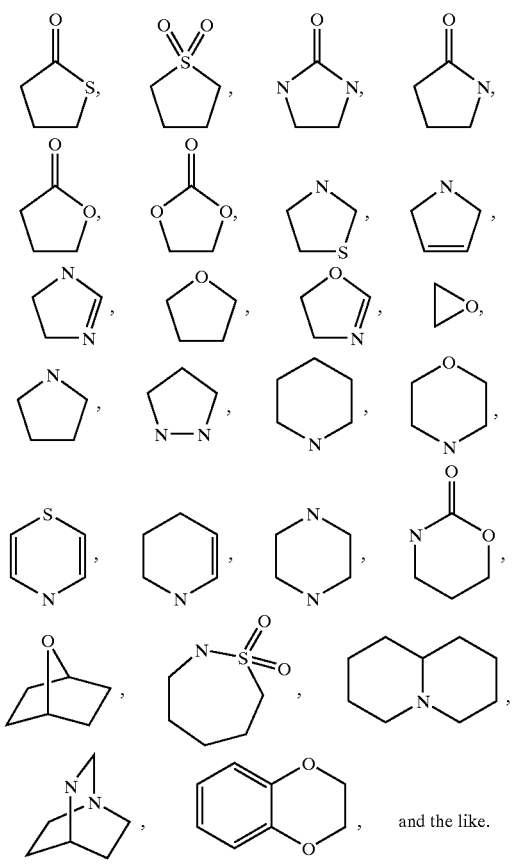

and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents.

Preferred GnRH agents of the invention include those having a $K_i$ value of about 100 nM or less against GnRH. Especially preferred GnRH agents are those having a $K_i$ value of about 10 nM or less against human GnRH (hGnRH), and even more preferred agents are those having a $K_i$ value of about 1 nM or less against hGnRH.

Preferred compounds of the invention include the examples described further below.

It is understood that while a compound may exhibit the phenomenon of tautomerism, the formula drawings within this specification expressly depict only one of the possible tautomeric forms. It is therefore to be understood that a formula is intended to represent any tautomeric form of the depicted compound and is not to be limited merely to a specific compound form depicted by the structural formula.

It is also understood that a compound of Formula I or II may exist as an "E" or "Z" configurational isomer, or a mixture of E and Z isomers. It is therefore to be understood that a formula is intended to represent any configurational form of the depicted compound and is not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. In one preferred embodiment, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

As indicated above, GnRH agents in accordance with the invention also include active tautomeric and stereoisomeric forms of the compounds of Formula I and II, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, Formulas I and II are intended to cover, where applicable, solvated as well as unsolvated forms of the compounds. Thus, each formula includes compounds having the indicated structure, including the hydrated as well as the non-hydrated forms.

In addition to compounds of the Formulas I and II, the GnRH agents of the invention include pharmaceutically acceptable salts, prodrugs, and active metabolites of such compounds, and pharmaceutically acceptable salts of such metabolites. A "pharmaceutically acceptable prodrug" is a compound that may be converted under physiological conditions or by solvolysis to the specified compound or to a pharmaceutically acceptable salt of such compound. A "pharmaceutically active metabolite" is a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86(7), 765–767 (1997); Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); Larsen, *Design and Application of Prodrugs*, Drug Design and Development (Krogsgaard-Larsen et al. eds., Harwood Academic Publishers, 1991); Dear et al., *J. Chromatogr. B.* 748, 281–293 (2000); Spraul et al., *J. Pharmaceutical & Biomedical Analysis*, 10(8), 601–605 (1992); and Prox et al., *Xenobiol.*, 3(2), 103–112 (1992).

The term "pharmaceutically acceptable salts" refers to salt forms that are pharmacologically acceptable and substantially non-toxic to the subject being administered the GnRH agent. Pharmaceutically acceptable salts include conventional acid-addition salts or base-addition salts formed from suitable nontoxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isothionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammomnum hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

A variety of known assays and techniques may be employed to determine the level of activity of various forms of the compounds in the GnRH system. Ligand-binding assays are used to determine interaction with the receptor of interest. Where binding is of interest, a labeled receptor may be used, where the label is a fluorescer, enzyme, radioisotope, or the like, which registers a quantifiable change upon the binding of the receptor. Alternatively, the artisan may provide for an antibody to the receptor, where the antibody is labeled, which may allow for amplification of the signal. Binding may also be determined by competitive displacement of a ligand bound to the receptor, where the ligand is labeled with a detectable label. Where agonist and/or antagonist activity is of interest, an intact organism or cell may be studied, and the change in an organismic or cellular function in response to the binding of the compound of interest may be measured. Various devices are available for detecting cellular response, such as a microphysiometer available from Molecular-Devices, Redwood City, Calif. In vitro and in vivo assays useful in measuring GnRH antagonist activity are known in the art. See, e.g., Bowers et al., "LH suppression in cultured rat pituitary cells treated with 1 ng of LHRH," *Endocrinology*, 106, 675–683 (1980) (in vitro); and Corbin et al., "Antiovulatory activity (AOA) in rats," *Endocr. Res. Commun.*, 2, 1–23 (1975)., Particular test protocols that may be used are described below.

For example, GnRH-receptor antagonists may be functionally assessed by measurement of change in extracellular acidification rates as follows. The ability of compounds to block the extracellular rate of acidification mediated by GnRH in HEK 293 cells expressing human GnRH receptors is determined as a measure of the compound's antagonist activity in vitro. Approximately 100,000 cells/chamber are immobilized in agarose suspension medium (Molecular Devices) and perfused with unbuffered MEM media utilizing the Cytosensor® Microphysiometer (Molecular Devices). Cells are allowed to equilibrate until the basal acidification rate remains stable (approximately one hour). Control dose-response curves are performed to GnRH ($10^{-11}$ M to $10^{-7}$ M). Compounds are allowed to incubate 15 minutes prior to stimulation with GnRH, and are assessed for antagonist activity. After incubation with test compounds, repeat dose-response curves to GnRH in the presence or absence of various concentrations of the test compounds are obtained. Schild regression analysis is performed on compounds to determine whether compounds antagonize GnRH-mediated increases in extracellular acidification rates through a competitive interaction with the GnRH receptor.

In another test, accumulation of total inositol phosphates may be measured by formic acid extraction from cells, followed by separation of the phosphates on Dowex columns. Cells are split using trypsin into two 12-well plates and pre-labeled with $^3$H-myoinositol (0.5 Ci to 2 mCi per mL) for 16–18 hours in inositol-free medium. The medium is then aspirated and the cells rinsed with either 1×HBSS, 20 mM HEPES (pH 7.5), or serum-free DMEM, 1×HBSS, 20 mM HEPES (pH 7.5) containing test compound, and 20 mM LiCl is then added and the cells are incubated for the desired time. The medium is aspirated and the reaction stopped by addition of ice-cold 10 mM formic acid, which also serves to extract cellular lipids. Inositol phosphates are separated by ion-exchange chromatography on Dowex columns, which are then washed with 5 mL of 10 mM myoinositol and 10 mM formic acid. The columns are then washed with 10 mL of 60 mM sodium formate and 5 mM borax, and total inositol phosphates are eluted with 4.5 mL 1 M ammonium formate, 0.1 M formic acid.

It will be appreciated that the actual dosages of the agents of this invention will vary according to the particular agent being used, the particular composition formulated, the mode of administration, and the particular site, host, and disease being treated. Optimal dosages for a given set of conditions may be ascertained by those skilled in the art using conventional dosage-determination tests in view of the experimental data for a given compound. For oral administration, an exemplary daily dose generally employed will be from about 0.001 to about 1000 mg/kg of body weight, with courses of treatment repeated at appropriate intervals. Administration of prodrugs may be dosed at weight levels that are chemically equivalent to the weight levels of the fully active compounds.

To treat diseases or conditions mediated by GnRH agonism or antagonism, a pharmaceutical composition of the invention is administered in a suitable formulation prepared by combining a therapeutically effective amount (i.e., a GnRH modulating, regulating, or inhibiting amount effective to achieve therapeutic efficacy) of at least one GnRH agent of the invention (as an active ingredient) with one or more pharmaceutically suitable carriers, which may be selected from diluents, excipients and auxiliaries that facilitate processing of the active compounds into the final pharmaceutical preparations. Optionally, one or more additional active ingredients, such as a second GnRH agent, may be employed in a pharmaceutical composition according to the invention.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or nonaqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of an inventive agent may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration chosen. For injection, the agents of the invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellaant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartidges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly-soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used. Further, the pharmaceutical composition may be incorporated into a skin patch for delivery of the drug directly onto the skin.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

Synthesis of GnRH Reagents and Compounds:

The inventive agents may be prepared using the reaction routes and synthesis schemes as described below, employing the techniques available in the art using starting materials that are readily available. The preparation of preferred compounds of the present invention is described in detail in the following examples, but the artisan will recognize that the chemical reactions described may be readily adapted to prepare a number of other GnRH agents of the invention. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the invention.

Reagents useful for synthesizing compounds may be obtained or prepared according to techniques known in the art. For example, the preparation of free amines from common salt forms and stock reagent solutions can be useful for small-scale reactions. See also Abdel-Magid et al., "Reductive Amination of Aldehydes and Ketones with Sodium Triacetoxyborohydride," *J. Org. Chem.* 61: 3849 (1996).

Methanolic solutions of the free bases can be prepared from hydrochloride, dihydrochloride, hydrobromide, or other salts when the free base is soluble in methanol. In this procedure, once the sodium methoxide is added, care should be taken to prevent exposure to air, since amine free bases, particularly primary amines, absorb carbon dioxide from the air to form salts. A 10-mL quantity of a 0.1 M solution of a free base in methanol may be prepared as follows. Weigh 1.0 mmol of a monohydrochloride salt into a tared Erlenmeyer flask containing a stirring bar, and add 7 mL of methanol. To the stirred slurry, add 229 mL (1.0 mmol, 1 equiv.) of sodium methoxide in methanol (25 wt %, 4.37 M), stopper the flask, and stir the mixture vigorously for 2 hours. The slurry will sometimes change in appearance as a finer, milky precipitate of sodium chloride is formed. Filter the slurry through a 15-mL medium fritted glass funnel, wash the filter case with 1-2 mL methanol, transfer the filtrate to a 20-mL vial, and dilute to 10 mL with methanol. The theoretical yield of sodium chloride is nearly 59 mg, but the recovery is usually not quantitative, owing to a slight solubility in methanol. For a dihydrochloride salt, a second equivalent of sodium methoxide is required (458 mL).

A 0.5 M solution of sodium borohydride in ethanol may be prepared as follows. Sodium borohydride (520 mg, 13.8 mmol) is stirred in pure (non-denatured) anhydrous ethanol (25 mL) for ~2–3 minutes. The suspension is filtered through a medium fritted glass funnel to remove a small amount of undissolved solid (typically about 5% of the total mass of borohydride, or 25 mg). The filtrate should appear as a colorless solution that evolves only a little hydrogen. This solution should be used immediately, as it decomposes significantly over a period of a few hours, resulting in the formation of a gelatinous precipitate. Sodium borohydride is hygroscopic, so avoid exposure to air by making the solution at once after weighing the solid. Sodium borohydride has a solubility of about 4% in ethanol at room temperature. This corresponds to a little over 0.8 M. However, sometimes a small percentage of the solid remains undissolved regardless of the concentration being prepared, even after stirring for ≧5 minutes.

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal® bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60° F. 254 plates (Analtech (0.25 mm)) and eluted with the appropriate solvent ratios (v/v). The reactions were assayed by TLC and terminated as judged by the consumption of starting material.

The TLC plates were visualized by UV, absorption or with a p-anisaldehyde spray reagent or a phosphomolybdic acid reagent (Aldrich Chemical, 20 wt % in ethanol) which was activated with heat. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous $Na_2SO_4$ prior to filtration, and evaporation of the solvents was under reduced pressure on a rotary evaporator and noted as solvents removed in vacuo. Flash column chromatography [Still et al., A. J. Org. Chem. 43:2923 (1978)] was conducted using Baker-grade flash silica gel (47–61 mm) and a silica gel: crude material ratio of about 20:1 to 50:1, unless otherwise stated. Hydrogenolysis was done at the pressure indicated or at ambient pressure.

$^1$H-NMR spectra were recorded on a Bruker instrument operating at 300 MHz, 500 MHz, and $^{13}$C-NMR spectra was recorded operating at 75 MHz. NMR spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as $CDCl_3$ solutions, and when reported are in wave numbers ($cm^{-1}$). The mass spectra were obtained using LC/MS or APCI. All melting points are uncorrected.

All final products had greater than 95% purity (by HPLC at wavelengths of 220 nm and 254 nm).

Preparation of Intermediate

Compound 202, an intermediate used in examples described below, was synthesized according to the following scheme:

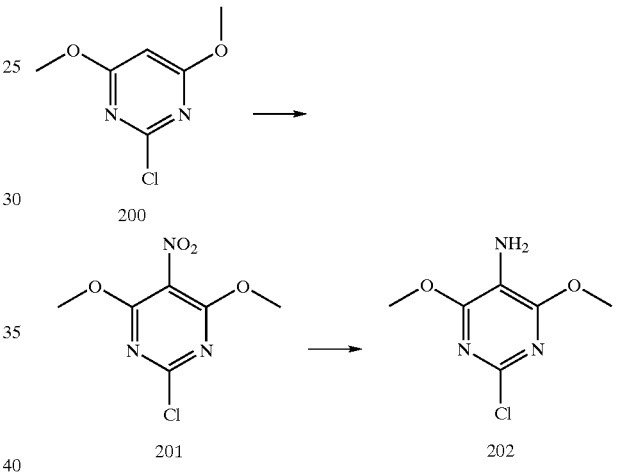

Into a three-necked, round bottom flask fitted with an overhead mechanical stirrer, was placed 920 g (0.675 mole) of 2-tetramethylammonium nitrate and 1 L DCM. The reaction flask was fitted with a thermometer and addition funnel. The suspension was stirred under nitrogen gas for 15 minutes at room temperature. Into the addition funnel was placed 190 g (0.675 mole, 118 mL) of trifluoromethanesulfonic anhydride that was added dropwise to the stirred suspension over a 35 minute duration so the temperature did not rise more than 5° C. The addition funnel was rinsed with a small amount of DCM, and this rinse was added to the stirred reaction suspension. The resultant suspension was stirred at room temperature for 1.5 hours. The addition funnel was charged with compound 200 (0.452 mole) dissolved in a minimum amount of DCM and was added dropwise at room temperature over 85 minutes such that the reaction temperature did not rise more than 5° C., and a bright crimson red suspension resulted. The reaction was stirred overnight at room temperature. Work up entailed adding 5 kg of ice to the stirred reaction suspension followed by 10% $NaHCO_3$ solution until a pH 8 was reached and the reaction turned from a burgundy to purple to blue to green to yellow color change. The lower DCM layer was separated and washed with 3×1.5 L of water. The DCM portion was then dried sodium sulfate, filtered, and the DCM solvent was removed by rotary evaporation giving compound 201.

Recrystallization from methanol/water afforded purified product. A three-necked, round-bottom flask containing a Teflon-coated magnetic stirring bar and a thermometer was charged with compound 201, 190-proof ethanol, and saturated aqueous ammonium chloride solution. The resultant suspension was stirred at room temperature for several minutes while iron powder (−325 mesh) was added in several portions over a 22 minute period such that the reaction temperature from a slow rising exotherm did not exceed 56° C. After addition of all the iron powder, the reaction was stirred for two and one-half hours in a room temperature environment. The reaction suspension was suction filtered, and the isolated iron powder was washed with 2×25 mL of ethanol, followed by 3×25 mL of ethyl acetate. Too the organic filtrate was added 200 mL water and 50 mL more ethyl acetate to effect separation. The upper organic layer was separated, and the lower aqueous layer was extracted with 3×50 mL of ethyl acetate. All ethyl acetate portions were combined and dried over anhydrous magnesium sulfate. Suction filtration, washing the spent magnesium sulfate with 15 mL ethyl acetate, and rotary evaporation left a pinkish, wet solid. The wet solid was dissolved in 75 mL dichloromethane, and the dichloromethane was washed with 3×25 mL of water. The combined water washings were back-extracted with 25 mL dichloromethane. The combined dichloromethane portions were dried over anhydrous magnesium sulfate. Suction filtration, washing the spent magnesium sulfate with 25 mL dichloromethane, and rotary evaporation afforded compound 202.

As described in examples below, compounds of formula 13 were prepared according to Scheme A set forth below:

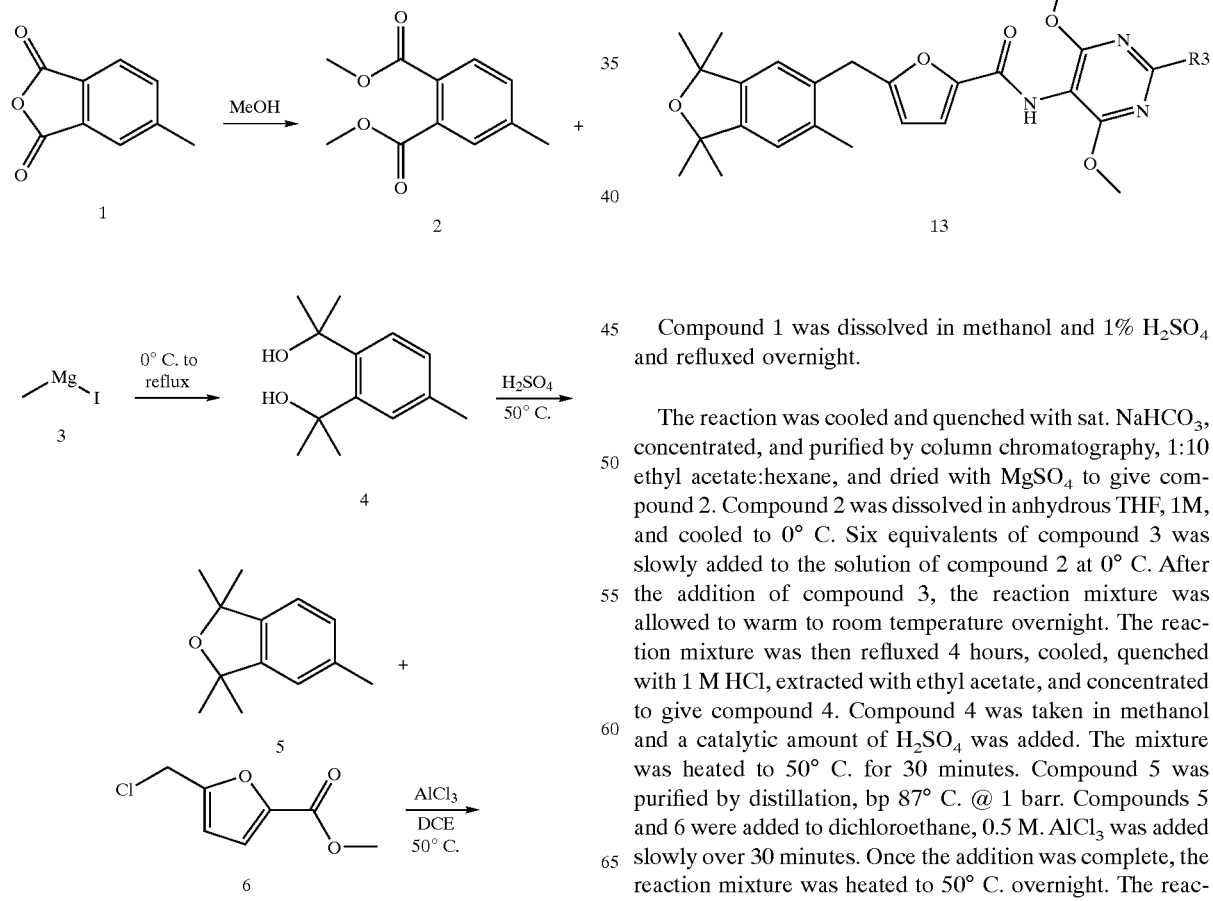

Compound 1 was dissolved in methanol and 1% $H_2SO_4$ and refluxed overnight.

The reaction was cooled and quenched with sat. $NaHCO_3$, concentrated, and purified by column chromatography, 1:10 ethyl acetate:hexane, and dried with $MgSO_4$ to give compound 2. Compound 2 was dissolved in anhydrous THF, 1M, and cooled to 0° C. Six equivalents of compound 3 was slowly added to the solution of compound 2 at 0° C. After the addition of compound 3, the reaction mixture was allowed to warm to room temperature overnight. The reaction mixture was then refluxed 4 hours, cooled, quenched with 1 M HCl, extracted with ethyl acetate, and concentrated to give compound 4. Compound 4 was taken in methanol and a catalytic amount of $H_2SO_4$ was added. The mixture was heated to 50° C. for 30 minutes. Compound 5 was purified by distillation, bp 87° C. @ 1 barr. Compounds 5 and 6 were added to dichloroethane, 0.5 M. $AlCl_3$ was added slowly over 30 minutes. Once the addition was complete, the reaction mixture was heated to 50° C. overnight. The reaction was then cooled, quenched with $H_2O$, concentrated, and purified by column chromatography using 5% ethyl acetate/hexane, to give compound 7. Compound 7 was dissolved in THF, 1 M, and 10 eq of NaOH in minimal H₂O was added. The reaction mixture was refluxed overnight, cooled and quenched with 1 M HCl to afford an acetic pH. The reaction was then extracted with dichloromethane and concentrated to give compound 8. Compound 8 was taken up in dichloromethane, 1 M, and SOCl₂ was slowly added. The reaction was allowed to stir overnight at room temperature. The mixture was then refluxed 4 hours, cooled back to room temperature, concentrated and purified by column-chromatography using hexanes. Compound 9 was then crystallized from hexanes. Compound 9 was then dissolved in ethyl acetate, 0.4M, and a compound of formula 12 and triethylamine were added. The mixture was allowed to stir overnight at room temperature. The resulting compound of formula 13 was filtered, washed with ethyl acetate, concentrated, taken back up in CHCl₃ and then washed with H₂O. The mixture was then purified by column chromatography using 100% acetonitrile to 20% methanol/79.5% acetonitrile/0.5% DIPEA to give purified compound of formula 13.

the compound of formula 13 was compound 108. Compound 108 was dissolved in methanol (0.25M) and MeONa (25% w/w) was added. The reaction mixture was allowed to stir at room temperature overnight. The mixture was then evaporated to dryness and an extraction was performed using ethyl acetate and water. The organic layer was concentrated and purified by prep-TLC with 50% ethyl acetate-:hexanes to give compound A1. NMR and mass spectrometry data consistent with the title product were as follows: $^1$H NMR (CDCl₃) δ 1.51(m, 12H), 2.34(s, 3H), 3.97(m, 9H), 4.03(s, 2H), 6.05(d, 1H, J=3.40 Hz), 6.86(s, 1H), 6.92(s, 1H), 7.11(d, 1H, J=3.40 Hz). M/z 482.2(M+1).

Example A2

5-(1,1,3,3,6-Pentamethyl-1,3-dihydro-isobenzofuran-5-ylmethyl)-furan-2-carboxylic acid (4,6-dimethoxy-2-phenoxy-pyrimidin-5-yl)-amide Example A1
5-(1,1,3,3,6-Pentamethyl-1,3-dihydro-isobenzofuran-5-ylmethyl)-furan-2-carboxylic Acid (2,4,6-trimethoxy-pyrimidin-5-yl)-amide

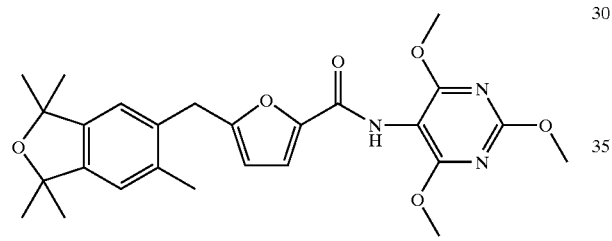

A1

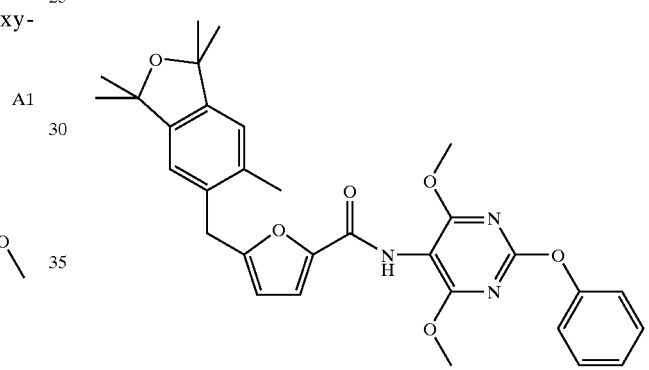

A2

The synthesis of compound A1 from compound 108 is shown below.

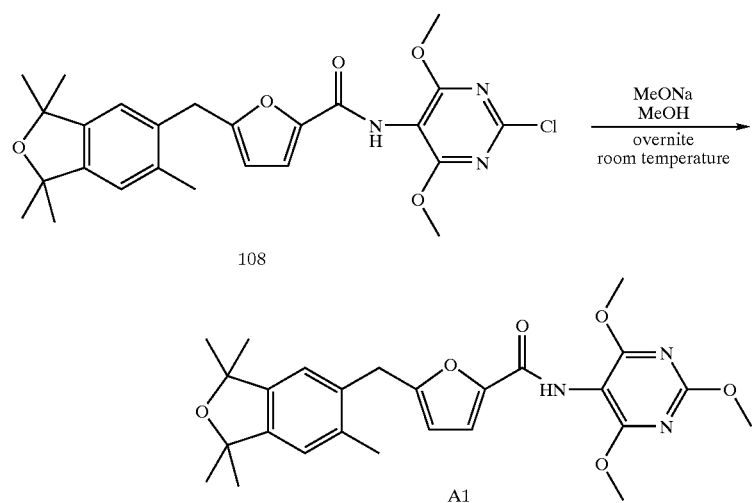

Compound A1 was synthesized according to Scheme A where the compound of formula 12 was compound 202 and The synthesis of compound 104 is outlined below.

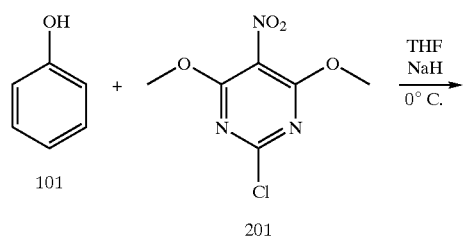

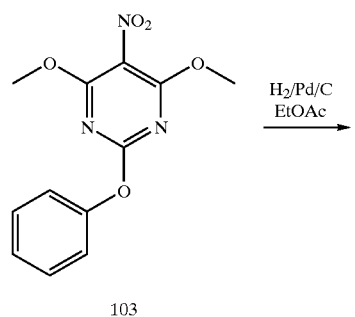

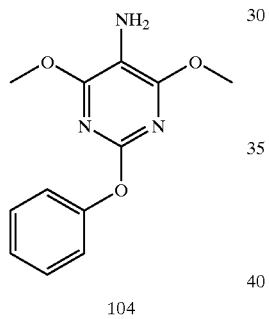

Example A3
5-(1,1,3,3,6-Pentamethyl-1,3-dihydro-isobenzofuran-5-ylmethyl)-furan-2-carboxylic acid [2-(2-hydroxy-ethoxy)-4,6-dimethoxy-pyrimidin-5-yl]-amide

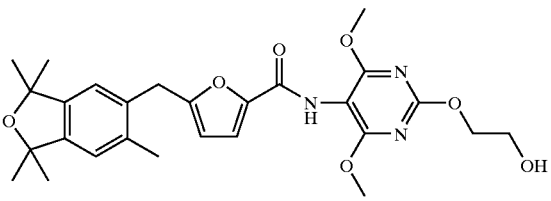

The synthesis of compound 113 is outlined below.

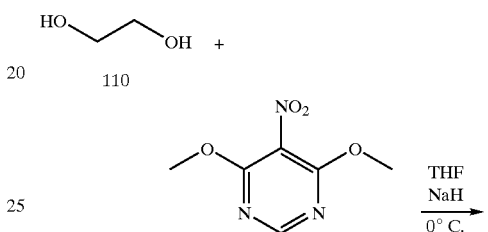

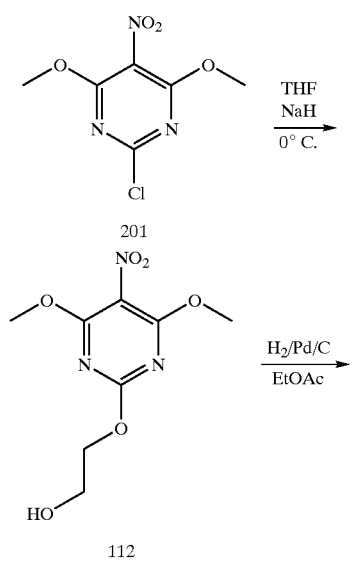

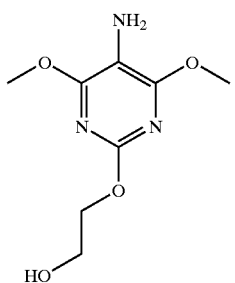

Compound 101 (12.9 g, 0.137 mol) and compound 201 (30 g, 0.137 mol) were taken in anhydrous THF (600 ml) and cooled to 0° C. NaH, 1 eq, was added slowly so that the temperature was never >5° C. Reaction was monitored by TLC, DCM:hexanes 1:1. Once complete, the reaction mixture was quenched by pouring mixture into ice water. Extracted with DCM and washed with water and brine then dried over MgSO$_4$. Filtered and concentrated, then crystallized from ethanol to give compound 103 in 93% yield. Compound 103 (34.6 g, 0.125 mol) was taken in ethyl acetate (300 ml) and Pd/C (4–5 g) was added to hydrogenation bottle. Mixture was hydrogenated until theoretical H$_2$ was taken up. Filtered and concentrated then recrystallized from hexanes to give compound 104 in 90.6% yield. Compound A2 was synthesized according to-scheme A where compound 12 was compound 104. NMR and mass spectrometer data consistent with the title product were as follows: $^1$H NMR (MeOD) δ 1.47(m, 12H), 2.32(s, 3H), 3.81(s, 6H), 4.09(s, 3H), 6.06(d, 1H, J=3.40 Hz), 6.99(d, 2H, J=3.02 Hz), 7.10(d, 1H, J=3.02 Hz), 7.22(m, 2H), 7.42(m, 2H). M/z 544.3 (M+1).

Compounds 110 and 201 were taken up in anhydrous THF and cooled to 0° C. NaH, 1 eq, was added slowly so that the temperature was never >5° C. Reaction was monitored by TLC, DCM:hexanes 1:1. Once complete, the reaction mixture was quenched by pouring mixture into ice water. Extracted with DCM and washed with water and brine then dried over MgSO$_4$. Filtered and concentrated, then crystallized from ethanol to give compound 112. Compound 112 was taken in ethyl acetate and Pd/C was added to hydrogenation bottle. Mixture was hydrogenated until theoretical H$_2$ was taken up. Filtered and concentrated then recrystallized from hexanes to give compound 113. Compound A3 was synthesized according to scheme A where compound 12 was compound 113. NMR and mass spectrometry data consistent with the title product were as follows: $^1$H NMR (MeOD) δ 1.47(m, 12H), 2.33(s, 3H), 3.88(t, 2H, J=4.91 Hz), 3.93(s, 6H), 4.10(s, 3H), 4.44(t, 2H, J=4.91 Hz), 6.06(d, 1H, J=3.40 Hz), 6.98(m, 2H), 7.09(d, 1H, J=3.02 Hz). M/z 512.2 (M+1).

Example A4
5-(1,1,3,3,6-Pentamethyl-1,3-dihydro-isobenzofuran-5-ylmethyl)-furan-2-carboxylic acid [4,6-dimethoxy-2-(2-methoxy-ethoxy)-pyrimidin-5-yl]-amide

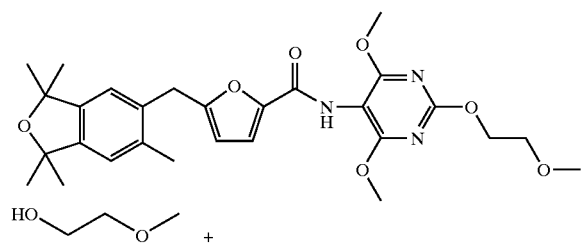

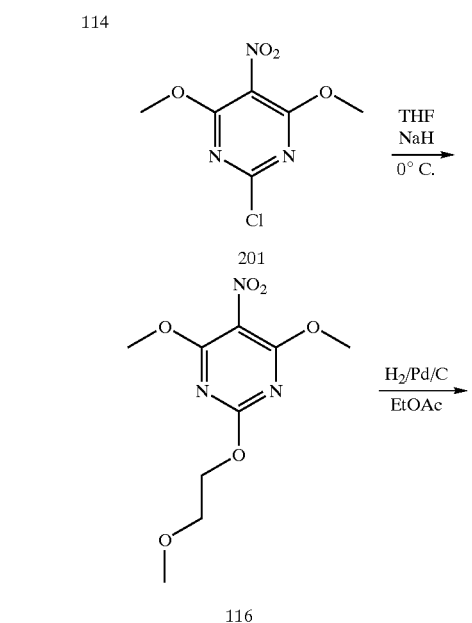

Compound 114 and compound 201 were taken in anhydrous THF and cooled to 0° C. NaH, 1 eq, was added slowly so that the temperature was never >5° C. Reaction was monitored by TLC, DCM:hexanes 1:1. Once complete, the reaction mixture was quenched by pouring mixture into ice water. Extracted with DCM and washed with water and brine then dried over MgSO$_4$. Filtered and concentrated, then crystallized from ethanol to give compound 116. Compound 116 was taken in ethyl acetate and Pd/C was added to hydrogenation bottle. Mixture was hydrogenated until theoretical H$_2$ was taken up. Filtered and concentrated then recrystallized from hexanes to give compound 117. Compound A4 was synthesized according to scheme A where compound 12 was compound 117. NMR and mass spectrometry data consistent with the title product were as follows: $^1$H NMR (MeOD) δ 1.46(m, 12H), 2.32(s, 3H), 3.40(s, 3H), 3.74(t, 2H, J=4.53 Hz), 3.93(s, 6H), 4.09(s, 3H), 4.50(t, 2H, J=4.53 Hz), 6.06(d, 1H, J=3.02 Hz), 6.98(m, 2H), 7.09(d, 1H, J=3.02 Hz). M/z 526.2 (M+1).

Compounds of formula 21 were prepared according to Scheme B set forth below:

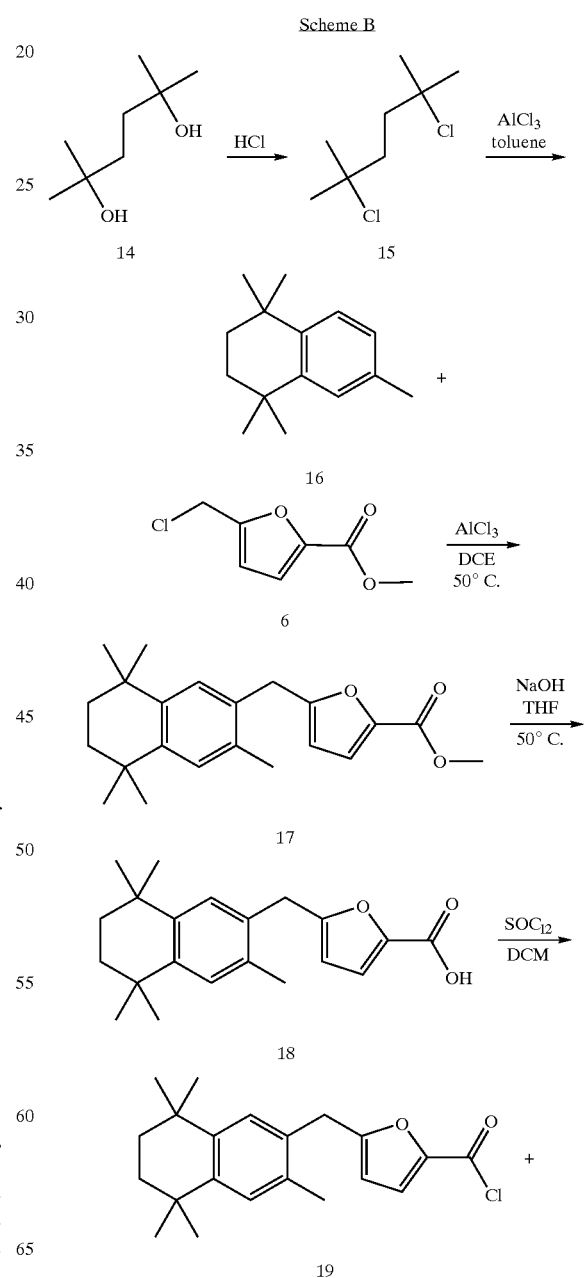

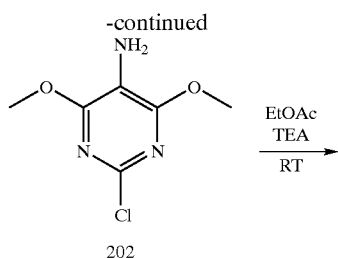

202

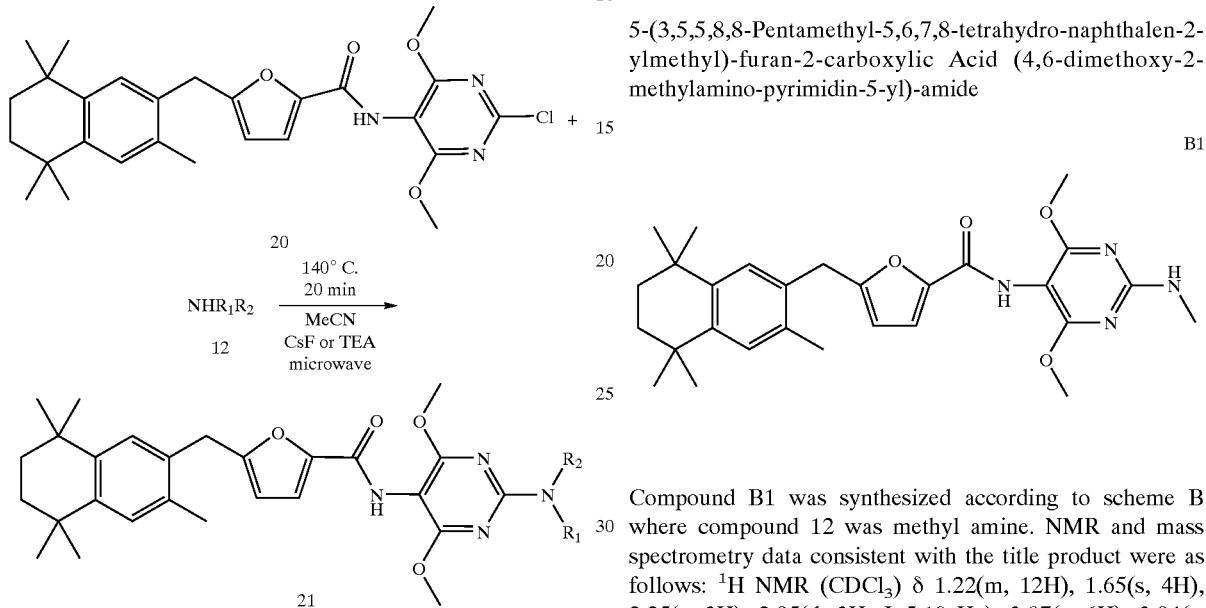

HCl (excess) was added to the diol, compound 14, neat, and allowed to stir for 30 minutes. The dichloride was extracted with hexanes and concentrated to give crude compound 15. The dichloride was then passed through silica gel with 10% ethyl acetate/hexanes to give purified product. The dichloride was then dissolved in toluene (10 eq) and 0.2 eq of aluminum chloride was added slowly over 30 min. Reaction was allowed to stir 2 hours then quenched with water. Organic layer was extracted and concentrated. Crude product was passed through silica gel to give purified product, compound 16. Compounds 16 and 6 were added to dichloroethane, 0.5M. AlCl₃ was added slowly over 30 minutes. Once the addition was complete, the reaction mixture was heated to 50° C. overnight. The reaction was then cooled, quenched with H₂O, concentrated, and purified by column chromatography using 5% ethyl acetate/hexane, to give compound 17. Compound 17 was dissolved in THF, 1 M, and 10 eq of NaOH in minimal H₂O was added. The reaction mixture was refluxed overnight, cooled and quenched with 1 M HCl to afford an acetic pH. The reaction was then extracted with dichloromethane and concentrated to give compound 18. Compound 18 was taken up in dichloromethane, 1 M, and SOCl₂ was slowly added. The reaction was allowed to stir overnight at room temperature. The mixture was then refluxed 4 hours, cooled back to room temperature, concentrated and purified by column chromatography using hexanes. Compound 19 was then crystallized from hexanes. Compound 19 was then dissolved in ethyl acetate, 0.4M, and compound 202 and triethylamine were added. The mixture was allowed to stir overnight at room temperature. Compound 20 was filtered, washed with ethyl acetate, concentrated, taken back up in CHCl₃ and then washed with H₂O. Compounds 20, 12, and CsF were added to acetonitrile, 1M, and microwaved for 20 minutes at 140° C. The mixture was then purified by column chromatography using 100% acetonitrile to 20% methanol/79.5% acetonitrile/0.5% DIPEA to give compound 21.

Example B1

5-(3,5,5,8,8-Pentamethyl-5,6,7,8-tetrahydro-naphthalen-2-ylmethyl)-furan-2-carboxylic Acid (4,6-dimethoxy-2-methylamino-pyrimidin-5-yl)-amide

B1

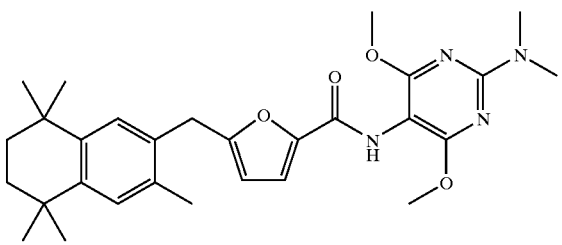

Compound B1 was synthesized according to scheme B where compound 12 was methyl amine. NMR and mass spectrometry data consistent with the title product were as follows: ¹H NMR (CDCl₃) δ 1.22(m, 12H), 1.65(s, 4H), 2.25(s, 3H), 2.95(d, 3H, J=5.10 Hz), 3.87(s, 6H), 3.94(s, 2H), 6.02(d, 1H, J=3.40 Hz), 7.03(s, 1H), 7.06(d, 1H, J=3.40 Hz), 7.09(s, 1H). M/z 493.2(M+1).

Example B2

5-(3,5,5,8,8-Pentamethyl-5,6,7,8-tetrahydro-naphthalen-2-ylmethyl)-furan-2-carboxylic Acid (dimethylamino-dimethoxy-pyrimidin-5-yl)-amide

B2

Compound B2 was synthesized according to scheme B where the compound of formula 12 was di-methyl amine. NMR and mass spectrometry data consistent with the title product were as follows: ¹H NMR(CDCl₃) δ 7.09(s, 1H), 7.06(d, 1H, J=3.40 Hz), 7.04(s, 1H), 6.02(d, 1H, J=3.40 Hz), 3.94(s, 2H), 3.89(s, 6H), 3.14(s, 6H), 2.26(s, 3H), 1.66(s, 4H), 1.27(s, 6H), 1.23(s, 6H). M/z 507.3(M+1)

Example B3
5-(3,5,5,8,8-Pentamethyl-5,6,7,8-tetrahydro-naphthalen-2-ylmethyl)-furan-2-carboxylic Acid (4,6-dimethoxy-2-morpholin-4-yl-pyrimidin-5-yl)-amide

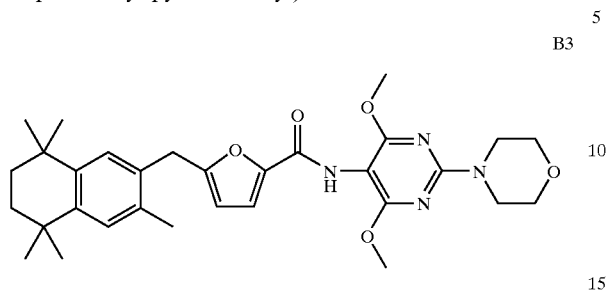

B3

Compound B3 was synthesized according to scheme B where compound 12 was morpholine. NMR and mass spectrometry data consistent with the title product were as follows: $^1$H NMR (CDCl$_3$) δ 1.24(m, 12H), 1.65(s, 4H), 2.25(s, 3H), 3.75(m, 8H), 3.87(s,), 3.94(s, 3H), 6.03(d, 1H, J=3.40 Hz), 7.03(s, 1H), 7.09(m, 2H). M/z 549.3 (M+1).

Example B4
5-(3,5,5,8,8-Pentamethyl-5,6,7,8-tetrahydro-naphthalen-2-ylmethyl)-furan-2-carboxylic Acid [4,6-dimethoxy-2-(3-morpholin-4-yl-propylamino)-pyrimidin-5-yl]-amide

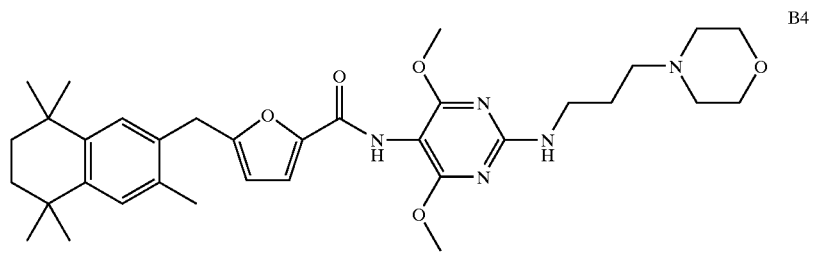

B4

Compound B4 was synthesized according to scheme B where compound 12 was N-(3-aminopropyl)morpholine. NMR and mass spectrometry data consistent with the title product were as follows: $^1$H NMR (CDCl$_3$) δ 1.23 and 1.27(s, 6H each), 1.66(s, 4H), 1.82(br s, 2H), 2.26(s, 3H), 2.45(br s, 6H), 2.54(m, 2H), 3.49(m, 2H), 3.77(br s, 4H), 3.88(s, 6H), 4.10(s, 2H), 5.72(t, 1H, J=10.39 Hz), 6.02(d, 1H, J=3.40 Hz), 7.06(d, 1H, J=3.40 Hz), 7.01(m, 3H and NH). M/z 606(M+1).

Example C1 was prepared according to Scheme C set forth below:

Scheme C

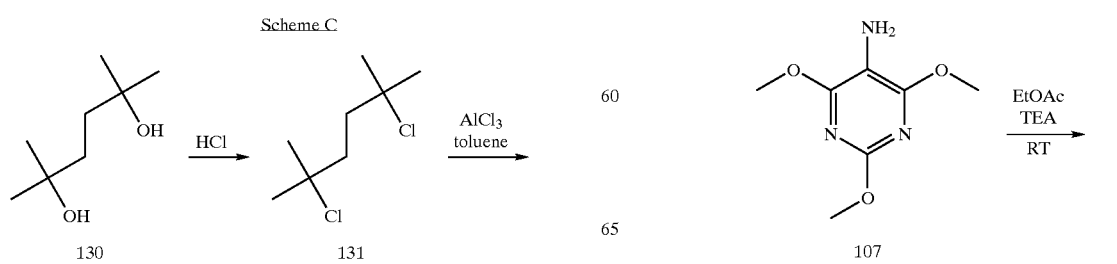

-continued

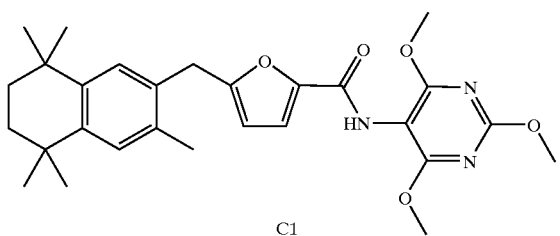

C1

HCl (excess) was added to the diol, compound 130, neat and allowed to stir for 30 minutes. The dichloride, compound 131, was extracted with hexanes and concentrated to give crude compound 131. Compound 131 was then passed through silica gel with 10% ethyl acetate/hexanes to give purified product and then dissolved in toluene (10 eq) and 0.2 eq of aluminum chloride was added slowly over 30 min. The reaction mixture was allowed to stir 2 hours then quenched with water. The organic layer was extracted and concentrated. The crude product was passed through silica gel to give purified product, compound 132. Compounds 132 and 133 were added to dichloroethane, 0.5M. AlCl₃ was added slowly over 30 minutes. Once the addition was complete, the reaction mixture was heated to 50° C. overnight. The reaction was then cooled, quenched with H₂O, concentrated, and purified by column chromatography using 5% ethyl acetate/hexane, to give compound 134. Compound 134 was dissolved in THF, 1 M, and 10 eq of NaOH in minimal H₂O120 was added. The reaction mixture was refluxed overnight, cooled and quenched with 1 M HCl to afford an acetic pH. The reaction was then extracted with dichloromethane and concentrated to give compound 135. Compound 135 was taken up in dichloromethane, 1 M, and SOCl₂ was slowly added. The reaction was allowed to stir overnight at room temperature. The mixture was then refluxed 4 hours, cooled back to room temperature, concentrated and purified by column chromatography using hexanes. Compound 136 was then crystallized from hexanes.

Example C1

5-(3,5,5,8,8-Pentamethyl-5,6,7,8-tetrahydro-naphthalen-2-ylmethyl)-furan-2-carboxylic Acid (2,4,6-trimethoxy-pyrimidin-5-yl)-amide

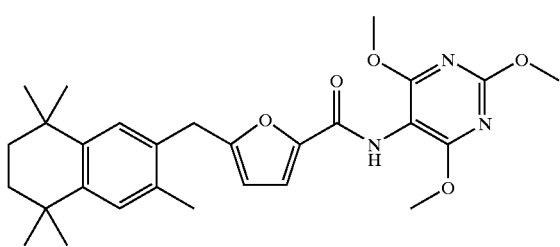

C1

The synthesis of compound 107 is outlined below.

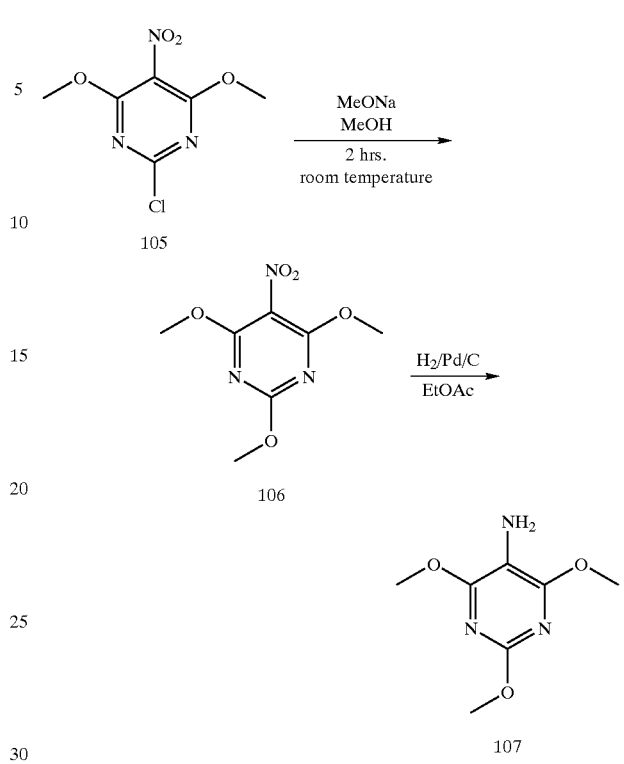

Compound 201, dimethoxynitropyrimidine chloride, was suspended in methanol (0.25M) and was added MeONa (25% w/w) and allowed to stir at room temperature for 2 hours. The reaction was evaporated to dryness then added ethyl acetate and water. The ethyl acetate layer is washed with water and evaporated to yield 77% of compound 106, trimethoxynitropyrimidine. The trimethoxynitropyrimidine was dissolved in methanol (0.25M), added catalytic amount of HCl and Pd/C. Mixture was hydrogenated until theoretical H₂ was taken up. Filtered and concentrated to give compound 107. Compound C1 was synthesized according to scheme C where compound 12 is compound 107. Compounds 107 and 136 were combined with triethylamine in EtOAc to give compound C1 which was purified by column chromatography. NMR and mass spectrometry data consistent with the title product were as follows, ¹HMR (CDCl₃). δ 1.23(m, 12H), 1.66(s, 4H), 2.26(s, 3H), 3.95(s, 2H), 3.96(s, 6H), 3.97(s, 3H), 6.04(d, 1H, J=3.40 Hz), 7.03(s, 1H), 7.09(s, 1H), 7.10(d, 1H, J=3.40 Hz). M/z 494.2 (M+1).

The following examples were prepared according to Scheme D set forth below:

Scheme D

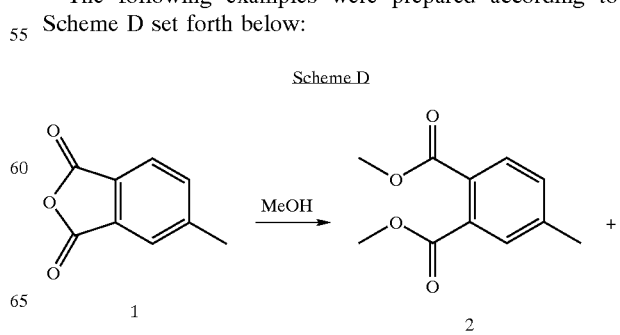

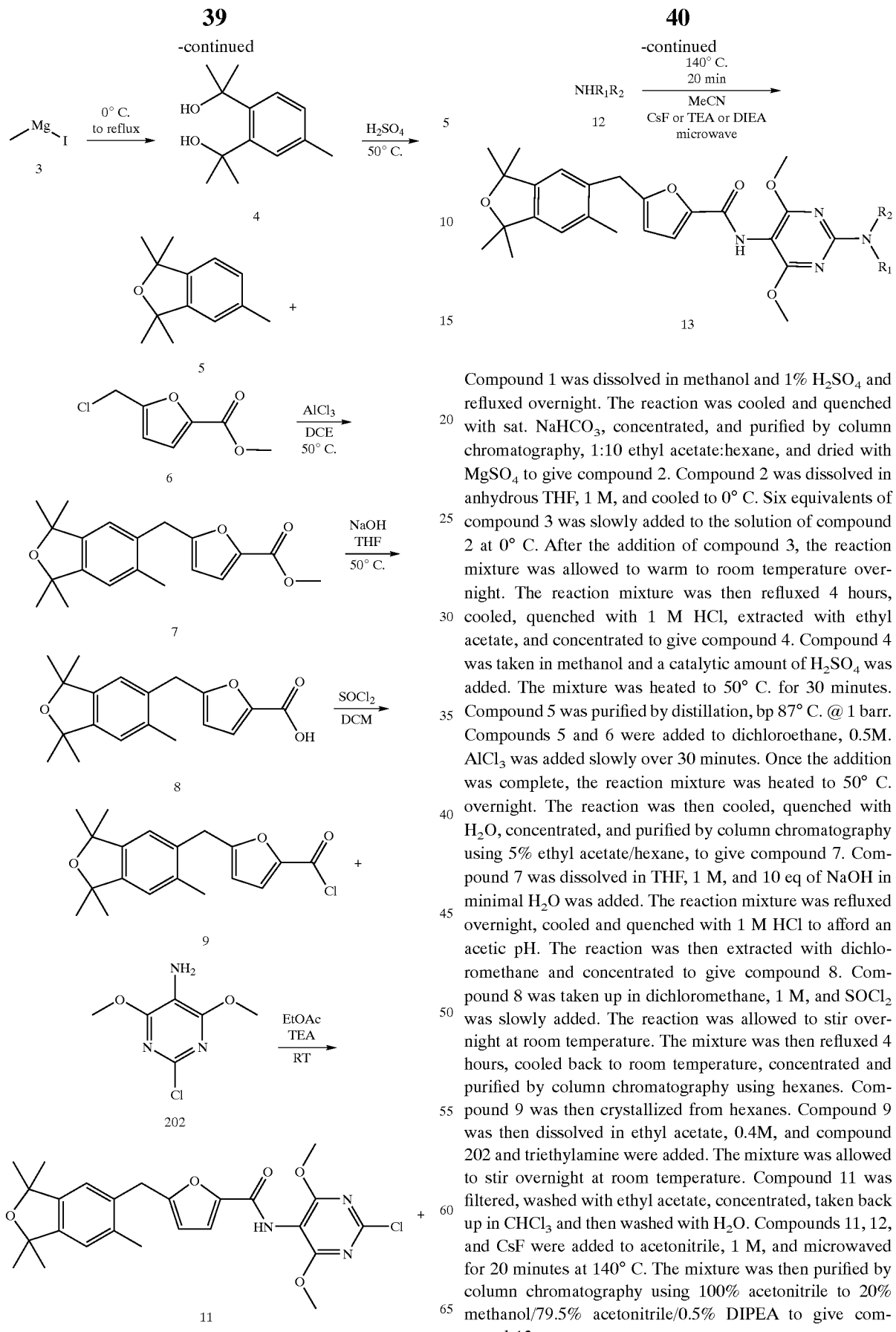

Compound 1 was dissolved in methanol and 1% $H_2SO_4$ and refluxed overnight. The reaction was cooled and quenched with sat. $NaHCO_3$, concentrated, and purified by column chromatography, 1:10 ethyl acetate:hexane, and dried with $MgSO_4$ to give compound 2. Compound 2 was dissolved in anhydrous THF, 1 M, and cooled to 0° C. Six equivalents of compound 3 was slowly added to the solution of compound 2 at 0° C. After the addition of compound 3, the reaction mixture was allowed to warm to room temperature overnight. The reaction mixture was then refluxed 4 hours, cooled, quenched with 1 M HCl, extracted with ethyl acetate, and concentrated to give compound 4. Compound 4 was taken in methanol and a catalytic amount of $H_2SO_4$ was added. The mixture was heated to 50° C. for 30 minutes. Compound 5 was purified by distillation, bp 87° C. @ 1 barr. Compounds 5 and 6 were added to dichloroethane, 0.5M. $AlCl_3$ was added slowly over 30 minutes. Once the addition was complete, the reaction mixture was heated to 50° C. overnight. The reaction was then cooled, quenched with $H_2O$, concentrated, and purified by column chromatography using 5% ethyl acetate/hexane, to give compound 7. Compound 7 was dissolved in THF, 1 M, and 10 eq of NaOH in minimal $H_2O$ was added. The reaction mixture was refluxed overnight, cooled and quenched with 1 M HCl to afford an acetic pH. The reaction was then extracted with dichloromethane and concentrated to give compound 8. Compound 8 was taken up in dichloromethane, 1 M, and $SOCl_2$ was slowly added. The reaction was allowed to stir overnight at room temperature. The mixture was then refluxed 4 hours, cooled back to room temperature, concentrated and purified by column chromatography using hexanes. Compound 9 was then crystallized from hexanes. Compound 9 was then dissolved in ethyl acetate, 0.4M, and compound 202 and triethylamine were added. The mixture was allowed to stir overnight at room temperature. Compound 11 was filtered, washed with ethyl acetate, concentrated, taken back up in $CHCl_3$ and then washed with $H_2O$. Compounds 11, 12, and CsF were added to acetonitrile, 1 M, and microwaved for 20 minutes at 140° C. The mixture was then purified by column chromatography using 100% acetonitrile to 20% methanol/79.5% acetonitrile/0.5% DIPEA to give compound 13.

Example D1

5-(1,1,3,3,6-Pentamethyl-1,3-dihydro-isobenzofuran-5-ylmethyl)-furan-2-carboxylic Acid (4,6-dimethoxy-2-phenylamino-pyrimidin-5-yl)-amide

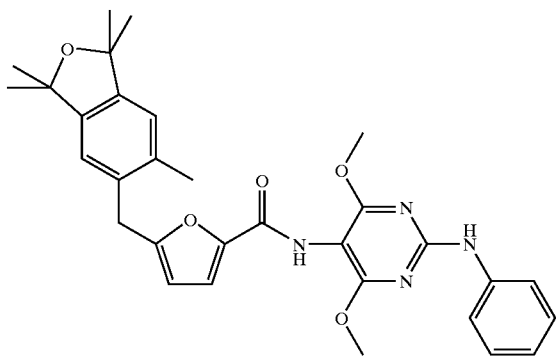

D1

Compound D1 was synthesized according to scheme D where compound 12 was benzyl amine. NMR and mass spectrometry data consistent with the title product were as follows: $^1$H NMR (MeOD) δ 1.47(m, 12H), 2.33(s, 3H), 3.94(s, 6H), 4.10(s, 3H), 6.05(d, 1H, J=3.40 Hz), 6.98(m, 3H), 7.09(d, 1H, J=3.02 Hz), 7.26(t, 2H, J=7.93 Hz), 7.71(d, 2H, J=7.93 Hz). M/z 543.3 (M+1).

Example D2

3-(1,1,3,3,6-pentamethyl-1,3-dihydro-isobenzofuran-5-yloxy)-furan-1-carboxylic acid{4,6-dimethoxy-2-[2-(methyl-{1-[5-(1,1,3,3,6-pentamethyl-1,3-dihydroisobenzofuran-5-yloxy)-furan-2-yl]-methanoyl}-amino)-ethylamino]-pyrimidin-5-yl}-amide

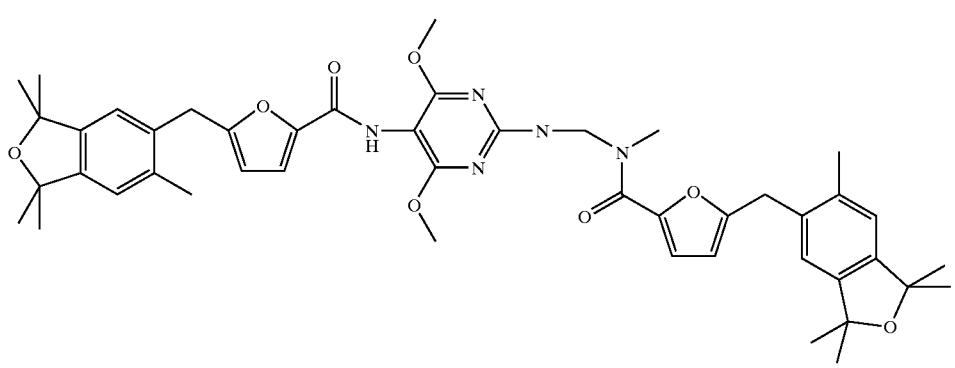

D2

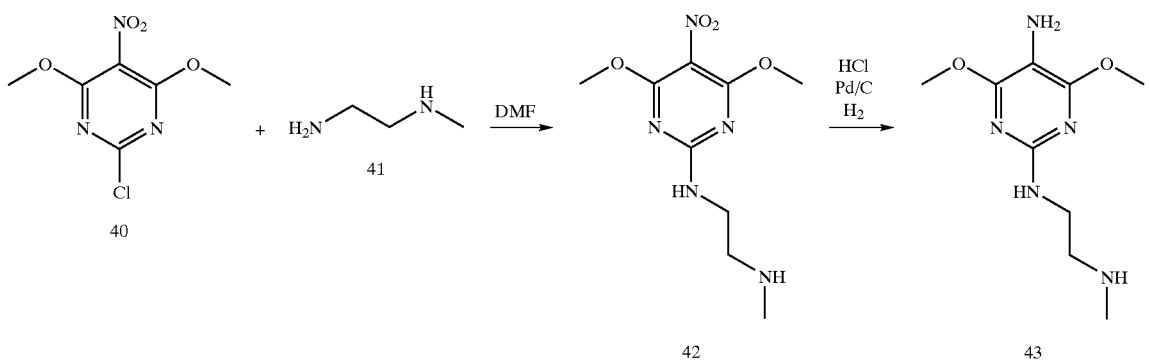

Compounds 40 and 41 were dissolved in DMF and stirred for 15 min. The resulting slurry was filtered to give compound 42. Compound 42 was dissolved in ethyl acetate and added-HCl(catalytic). Pd/C was added and-the mixture was hydrogenated overnight at 50 psi. The slurry was then filtered through Celite to give compound 43. Compound D2 was synthesized according to scheme D where compound 12 was compound 43 and two equivalents of compound 12 are reacted with compound 9 to give compound D2. NMR and mass spectrometry data consistent with the title product were as follows: $^1$H NMR (MeOD) δ 1.46(m, 24H), 2.25(s, 3H), 2.32(s, 3H), 3.20(s, 3H), 3.61(m, 2H), 3.84(m, 8H), 4.01(s, 2H), 4.08(s, 2H), 5.99(m, 1H), 6.06(m, 1H), 6.99(m, 6H). M/z 820.5 (M+1).

Example D3

5-(1,1,3,3,6-Pentamethyl-1,3-dihydro-isobenzofuran-5-ylmethyl)-furan-2-carboxylic Acid [4,6-dimethoxy-2-(3-morpholin-4-yl-propylamino)-pyrimidin-5-yl]-amide

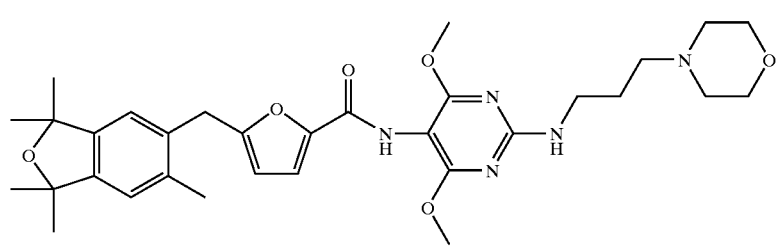

Compound D3 was synthesized according to scheme D where compound 12 was N-(3-aminopropyl)morpholine. NMR and mass spectrometry data consistent with the title product were as follows: $^1$H NMR (CDCl$_3$) δ 1.46(s, 6H), 1.52(s, 6H), 1.77(d, 2H, J=6.23 Hz), 2.31(s, 31H), 2.49(s, 4H), 3.47(t, 2H, J=6.04 Hz), 3.74(s, 4H), 3.86(s, 6H), 3.99(s, 2H), 5.76(t, 1H, J=5.57 Hz), 6.02(d, 1H, J=3.21 Hz), 6.83(s, 1H), 6.90(s, 1H), 7.02(s, 1H), 7.08(d, 1H, J=3.21 Hz). M/z 594(M+1).

Example D4

N-{4,6-dimethoxy-2-[(2-morpholin-4-ylethyl)amino]pyrimidin-5-yl}-5-[(1,1,3,3,6-pentamethyl-1,3-dihydro-2-benzofuran-5-yl)methyl]-2-furamide.

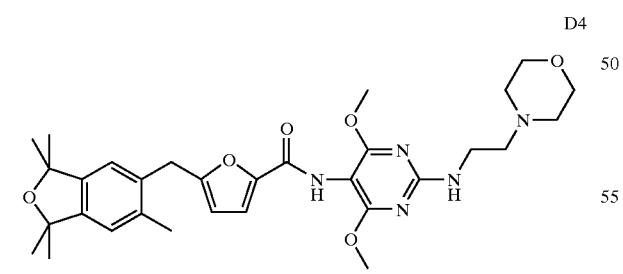

Compound D4 was synthesized according to scheme D where compound 12 was 4-(2-aminoethly)morpholine. NMR and mass spectrometry data consistent with the title product were as follows: $^1$H NMR (MeOD) δ 1.47(m, 12H), 2.33(s, 3H), 2.58(t, 4H, J=4.25 Hz), 2.65(t, 2H, J=6.61 Hz), 3.55(t, 2H, J=6.70 Hz), 3.71(t, 4H, J=4.63 Hz), 3.86(s, 6H), 4.10(s, 2H), 6.04(d, 1H, J=3.40 Hz), 6.98(s, 1H), 7.00(s, 1H), 7.06(d, 1H, J=3.40 Hz). M/z 580.3 (M+1).

Example D5

N-{4,6-dimethoxy-2-[(2-pyrrolidin-4-ylethyl)amino]pyrimidin-5-yl}-5-[(1,1,3,3,6-pentamethyl-1,3-dihydro-2-benzofuran-5-yl)methyl]-2-furamide.

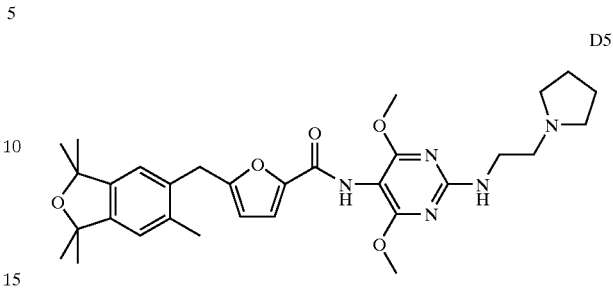

Compound D5 was synthesized according to scheme D where compound 12 was N-(2-aminoethyl)pyrrolidine. NMR and mass spectrometry data consistent with the title product were as follows: $^1$H NMR (MeOD) δ 1.47(m, 12H), 1.88(s, 4H), 2.32(s, 3H), 2.81(m, 4H), 2.91(t, 2H, J=6.42 Hz), 3.60(t, 2H, J=6.52 Hz), 3.87(s, 6H), 4.09(s, 2H), 6.05(d, 1H, J=3.40 Hz), 6.98(s, 1H), 7.00(s, 1H), 7.07(d, 1H, J=3.40 Hz). M/z 564.6 (M+1).

Example D6

N-{4,6-Dimethoxy-2-[(2-piperidin-1-ylethyl)amino]pyrimidin-5-yl}-5-[(1,1,3,3,6-pentamethyl-1,3-dihydro-2-benzofuran-5-yl)methyl]-2-furamide.

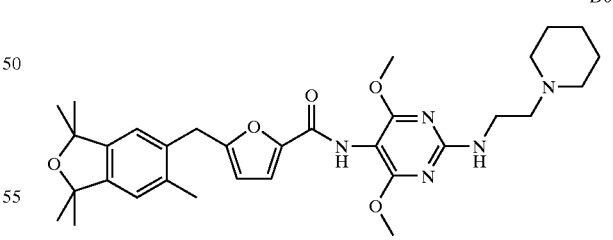

Compound D6 was synthesized according to scheme D where compound 12 was 1-(2-aminoethyl)piperidine. NMR and mass spectrometry data consistent with the title product were as follows: $^1$H NMR (MeOD) δ 1.47(m, 12H), 1.57(s, 2H), 1.72(m, 4H), 2.33(s, 3H), 2.89(m, 6H), 3.64(t, 2H, J=6.61 Hz), 3.87(s, 6H), 4.09(s, 2H), 6.05(d, 1H, J=3.40 Hz), 6.98(s, 1H), 7.00(s, 1H), 7.07(d, 1H, J=3.40 Hz). M/z 578.3 (M+1).

Example D7

N-(2-{[2-(Diethylamino)ethyl]amino}-4,6-dimethoxypyrimidin-5-yl)-5-[(1,1,3,3,6-pentamethyl-1,3-dihydro-2-benzofuran-5-yl)methyl]-2-furamide.

D7

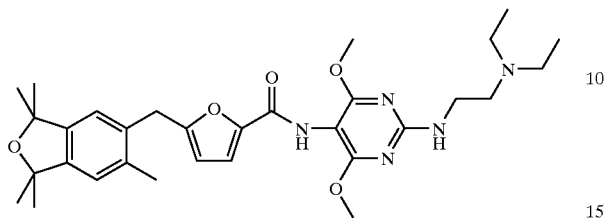

Compound D7 was synthesized according to scheme D where compound 12 was N,N-diethylethylenediamine. NMR and mass spectrometry data consistent with the title product were as follows: $^1$H NMR (MeOD) δ 1.26(t, 6H, J=7.18 Hz), 1.47(m, 12H), 2.32(s, 3H), 3.12(q, 4H, J=7.24 Hz), 3.22(t, 2H, J=6.42 Hz), 3.70(t, 2H, J=6.32 Hz), 3.88(s, 6H), 4.09(s, 2H), 6.05(d, 1H, J=3.40 Hz), 6.99(m, 2H), 7.07(d,1H, J=3.59 Hz). M/z 566.3 (M+1).

Example D8

N-[2-(Dimethylamino)-4,6-dimethoxypyrimidin-5-yl]-5-[(1,1,3,3,6-pentamethyl-1,3-dihydro-2-benzofuran-5-yl)methyl]-2-furamide

D8

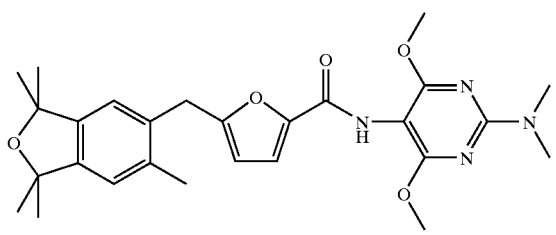

Compound D8 was synthesized according to scheme D where compound 12 was dimethylamine. NMR and mass spectrometry data consistent with the title product were as follows: $^1$H NMR (MeOD) δ 1.47(m, 12H), 2.32(s, 3H), 3.15(s, 6H), 3.88(s, 6H), 4.08(s, 2H), 6.04(d, 1H, J=3.40 Hz), 6.98(m, 2H), 7.06(d, 1H, J=3.40 Hz). M/z 495.2 (M+1).

Example D9

N-(2-{[3-(Dimethylamino)propyl]amino}-4,6-dimethoxypyrimidin-5-yl)-5-[(1,1,3,3,6-pentamethyl-1,3-dihydro-2-benzofuran-5-yl)methyl]-2-furamide.

D9

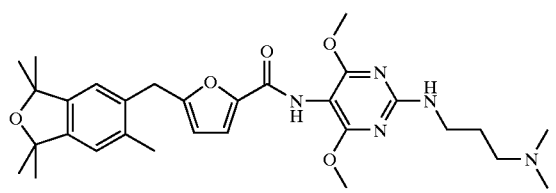

Compound D9 was synthesized according to scheme D where compound 12 was N,N-dimethyl-1,3-propanediamine. NMR and mass spectrometry data consistent with the title product were as follows: $^1$H NMR (MeOD) δ 1.48(m, 12H), 1.83(s, 2H), 2.32(s, 3H), 2.37(s, 4H), 2.55(s, 2H), 3.42(t, 2H, J=6.33 Hz), 3.87(s, 6H), 4.09(s, 2H), 6.04(d, 1H, J=3.40 Hz), 6.98(s, 1H), 7.00(s, 1H), 7.07(d, 1H, J=3.40 Hz). M/z 552.3 (M+1).

Example D10

N-(2-{[2-(Dimethylamino)ethyl]amino}-4,6-dimethoxypyrimidin-5-yl)-5-[(1,1,3,3,6-pentamethyl-1,3-dihydro-2-benzofuran-5-yl)methyl]-2-furamide.

D10

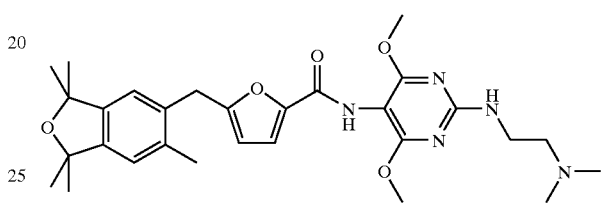

Compound D10 was synthesized according to scheme D where compound 12 was N,N-dimethylethylenediamine. NMR and mass spectrometry data consistent with the title product were as follows: $^1$H NMR (MeOD) δ 1.47(m, 12H), 2.32(s, 3H), 2.35(s, 4H), 2.62(t, 2H, J=6.61 Hz), 3.53(t, 2H, J=6.89 Hz), 3.87(s, 6H), 4.09(s, 2H), 6.06(d, 1H, J=3.21 Hz), 6.97(s, 1H), 7.00(s, 1H), 7.06(d, 1H, J=3.40 Hz). M/z 538.3 (M+1).

Example D11

N-(2-{[4-(Dimethylamino)butyl]amino}-4,6-dimethoxypyrimidin-5-yl)-5-[(1,1,3,3,6-pentamethyl-1,3-dihydro-2-benzofuran-5-yl)methyl]-2-furamide.

D11

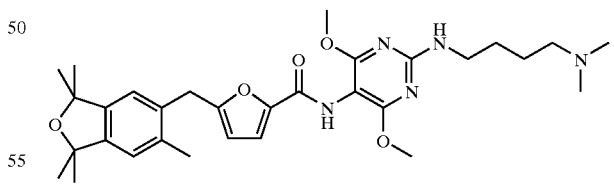

Compound D11 was synthesized according to scheme D where compound 12 was 4-dimethylaminobutylamine. NMR and mass spectrometry data consistent with the title product were as follows: $^1$H NMR (MeOD) δ 1.47(m, 12H), 1.73(m, 4H), 2.33(s, 3H), 2.75(s, 6H), 3.01(m, 2H), 3.44(t, 2H, J=6.61 Hz), 3.86(s, 6H), 4.09(s, 2H), 6.04(d, 1H, J=3.40 Hz), 6.98(s, 1H), 7.00(s, 1H), 7.07(d, 1H, J=3.40 Hz). M/z 566.3 (M+1).

Example D12

N-[2-({2-[(2-aminoethyl)amino]ethyl}amino)-4,6-dimethoxypyrimidin-5-yl]-5-[(1,1,3,3,6-pentamethyl-1,3-dihydro-2-benzofuran-5-yl)methyl]-2-furamide

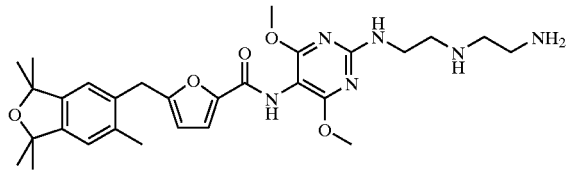

D12

Compound, D12 was synthesized according to scheme D where compound 12 was diethylenetriamine. NMR and mass spectrometry data consistent with the title product were as follows: $^1$H NMR (MeOD) δ 1.47(m, 12H), 2.31(s, 3H), 3.06(m, 6H), 3.59(m, 2H), 3.86(s, 6H), 4.08(s, 2H), 6.04(d, 1H, J=3.02 Hz), 6.97(s, 1H), 7.00(s, 1H), 7.07(d, 1H, J=3.02 Hz). M/z 553.3 (M+1).

Example D13

N-{4,6-Dimethoxy-2-[(1-methylpiperidin-4-yl)amino]pyrimidin-5-yl}-5-[(1,1,3,3,6-pentamethyl-1,3-dihydro-2-benzofuran-5-yl)methyl]-2-furamide

D13

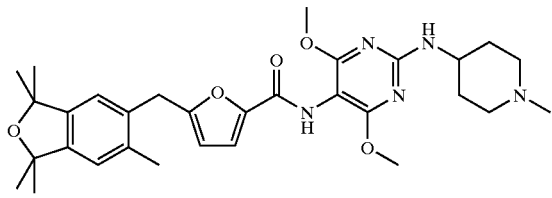

Compound D13 was synthesized according to scheme D where compound 12 was 1-methylpiperidin-4-amine. NMR and mass spectrometry data consistent with the title product were as follows: $^1$H NMR (MeOD) δ 1.47(m, 12H), 1.79(m, 4H), 1.93(s, 3H), 2.18(m, 4H), 2.33(s, 3H), 2.85(m, 4H), 3.23(m, 4H), 3.86(s, 6H), 3.97(m, 1H), 4.09(s, 2H), 6.05(d, 1H, J=3.40 Hz), 6.98(s, 1H), 7.00(s, 1H), 7.07(d, 1H, J=3.40 Hz). M/z 564.3 (M+1).

Example D14

N-{4,6-Dimethoxy-2-[(2-piperazin-1-ylethyl)amino]-pyrimidin-5-yl}-5-[(1,1,3,3,6-pentamethyl-1,3-dihydro-2-benzofuran-5-yl)methyl]-2-furamide.

D14

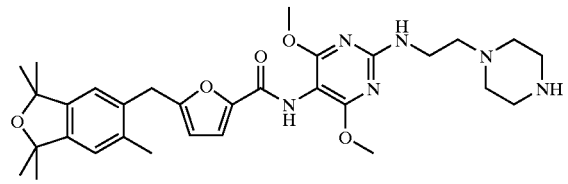

Compound D14 was synthesized according to scheme D where compound 12 was N-(2-aminoethyl)piperazine. NMR and mass spectrometry data consistent with the title product were as follows: $^1$H NMR (CDCl$_3$) δ 1.48(m, 12H) 2.32(s, 3H), 2.49(s, 4H), 2.57(m, 2H); 2.93(m, 4H), 3.48(m, 2H, J=6.33 Hz), 3.88(s, 6H), 4.00(s, 2H), 6.02(d, 1H, J=2.46 Hz), 6.84(s, 1H), 6.90(s, 1H), 7.08(d, 1H, J=3.02 Hz). M/z 579.3 (M+1).

Example D15

N-{2-[4-(2-Aminoethyl)piperazin-1-yl]-4,6-dimethoxypyrimidin-5-yl}-5-[(1,1,3,3,6-pentamethyl-1,3-dihydro-2-benzofuran-5-yl)methyl]-2-furamide

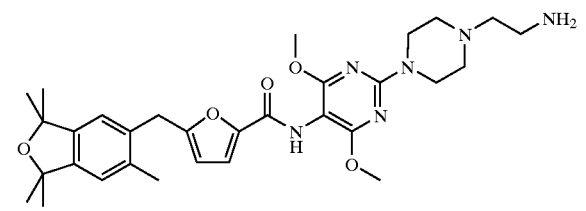

D15

Compound D15 was synthesized according to scheme D where compound 12 was N-(2-aminoethyl)piperazine. NMR and mass spectrometry data consistent with the title product were as follows: $^1$H NMR (CDCl$_3$) δ 1.48(m, 12H), 2.32(s, 3H), 2.48(m, 6H), 2.85(t, 2H, J=5.76 Hz), 3.80(t, 4H, J=4.25 Hz), 3.87(s, 6H), 4.00(s, 2H), 6.02(d, 1H, J=3.40 Hz), 6.82(s, 1H), 6.90(s, 1H), 7.09(d, 1H, J=3.21 Hz). M/z 579.3 (M+1).

Example D16

N-{2-[Bis(3-aminopropyl)amino]-4,6-dimethoxypyrimidin-5-yl}-5-[(1,1,3,3,6-pentamethyl-1,3-dihydro-2-benzofuran-5-yl)methyl]-2-furamide.

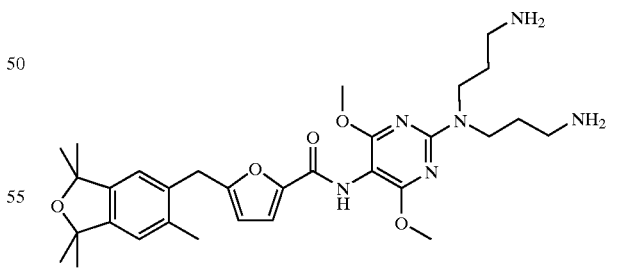

D16

Compound D16 was synthesized according to scheme D where compound 12 was 3,3'-diaminodipropylamine. NMR and mass spectrometry data consistent with the title product were as follows: $^1$H NMR (MeOD) δ 1.46(m, 12H), 2.31(s, 3H), 3.24(m, 4H), 3.91(m, 10H), 4.09(s, 2H), 6.06(d, 1H, J=3.40 Hz), 6.98(s, 2H), 7.09(d, 1H, J=3.40 Hz). M/z 581.3 (M+1).

Example D17
N-[2-({3-[(3-Aminopropyl)amino]propyl}amino)-4,6-dimethoxypyrimidin-5-yl}-5-[(1,1,3,3,6-pentamethyl-1,3-dihydro-2-benzofuran-5-yl)methyl]-2-furamide

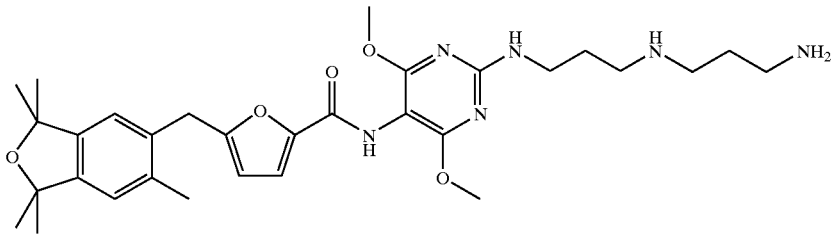

Compound D17 was synthesized according to scheme D where compound 12 was 3,3'-diaminodipropylamine. NMR and mass spectrometry data consistent with the title product were as follows: $^1$H NMR (MeOD) δ 1.47(m, 12H), 1.89(m, 4H), 2.33(s, 3H), 2.91(m, 6H), 3.47(t, 2H, J=6.42 Hz), 3.87(s, 6H), 4.09(s, 2H), 6.05(d, 1H, J=3.21 Hz), 6.98(s, 1H), 7.00(s, 1H), 7.07(d, 1H, 1=3.40 Hz). M/z 581.3 (M+1).

Example D18
N-[2-({3-[4-(3-Aminopropyl)piperazin-1-yl]propyl}amino)-4,6-dimethoxypyrimidin-5-yl}-5-[(1,1,3,3,6-pentamethyl-1,3-dihydro-2-benzofuran-5-yl)methyl]-2-furamide.

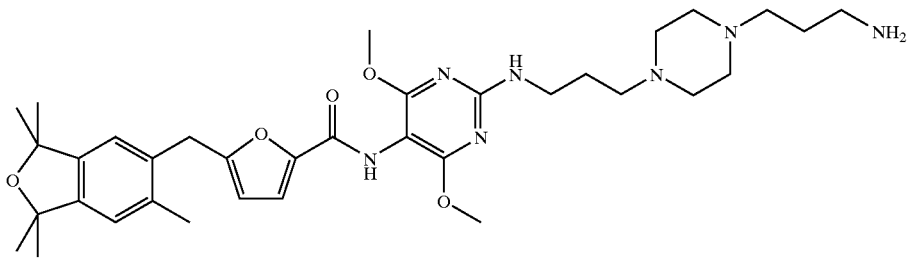

Compound D18 was synthesized according to scheme D where compound 12 was 1,4-bis(3-aminopropyl)piperazine. NMR and mass spectrometry data consistent with the title product were as follows: $^1$H NMR (MeOD) δ 1.47(m, 12H), 1.81(q, 4H, J=7.08 Hz), 2.33(s, 3H), 2.54(m, 12H), 2.98(t, 2H, J=7.18 Hz), 3.42(t, 2H, J=6.52 Hz), 3.86(s, 6H), 4.09(s, 2H), 6.05(d, 1H, J=3.40 Hz), 6.98(s, 1H), 7.00(s, 1H), 7.06(d, 1H, J=3.40 Hz). M/z 650.4 (M+1).

Example D19
N-(2-{[3-(1H-Imidazol-1-yl)propyl]amino}-4,6-dimethoxypyrimidin-5-yl}-5-[(1,1,3,3,6-pentamethyl-1,3-dihydro-2-benzofuran-5-yl)methyl]-2-furamide

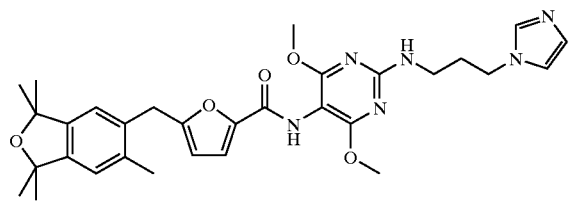

Compound D19 was synthesized according to scheme D where compound 12 was 1-(3-aminopropyl)imidazole.

NMR and mass spectrometry data consistent with the title product were as follows: $^1$H NMR (CDCl$_3$) δ 1.48(m, 12H), 2.11(m, 2H), 2.32(s, 3H), 3.40(q, 2H, J=6.42 Hz), 3.85(s, 6H), 4.00(s, 2H), 4.06(t, 2H, J=7.08 Hz), 6.03(d, 1H, J=3.40 Hz), 6.84(s, 11H), 6.90(s, 11H), 7.06(m, 3H), 7.51(s, 1H). M/z 575.3 (M+1H).

Example D20
N-(4,6-Dimethoxy-2-{[2-(methylamino)ethyl]amino}-pyrimidin-5-yl}-5-[(1,1,3,3,6-pentamethyl-1,3-dihydro-2-benzofuran-5-yl)methyl]-2-furamide

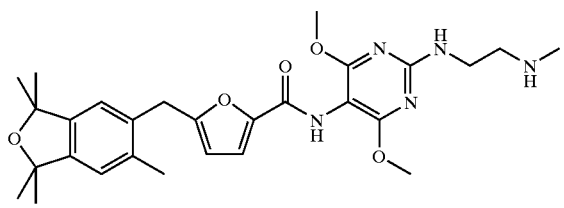

D20

Compound D20 was synthesized according to scheme D where compound 12 was N-methylethylenediamine. NMR and mass spectrometry data consistent with the title product were as follows: $^1$H NMR (CDCl$_3$) δ 1.49(m, 12H), 2.32(s, 3H), 2.98(t, 2H, J=5.85 Hz), 3.16(s, 3H), 3.68(t, 2H, J=6.14 Hz), 3.88(s, 6H), 4.00(s, 2H), 6.02(d, 1H, J=3.21 Hz), 6.84(s, 1H), 6.91(s, 1H), 7.08(d, 1H, J=3.21 Hz). M/z 524.3 (M+1).

Example D21
N-{2-[Bis(3-piperidin-1-ylpropyl)amino]-4,6-dimethoxypyrimidin-5-yl}-5-[(1,1,3,3,6-pentamethyl-1,3-dihydro-2-benzofuran-5-yl)methyl]-2-furamide.

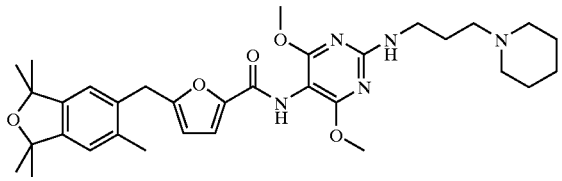

D22

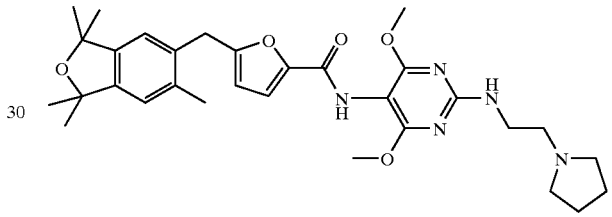

D23

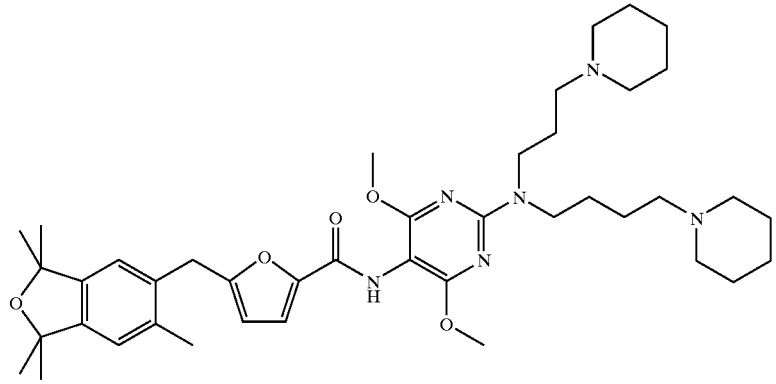

D21

Compound D21 was synthesized according to scheme D where compound 12 was N-aminopropyl piperidine. The product D21 was found as a side product of the reaction to make compound D22. NMR and mass spectrometry data consistent with the title product were as follows: $^1$H NMR (CDCl$_3$) δ 1.41(m, 4H), 1.49(m, 12H), 1.58(m, 8H), 1.83(m, 4H), 2.32(s, 3H), 2.39(m, 12H), 3.54(t, 4H, J=7.74 Hz), 3.86(s, 6H), 4.00(s, 2H), 6.02(d, 1H, J=3.40 Hz), 6.84(s, 1H), 6.90(s, 1H), 7.08(d, 1H, J=3.21 Hz). M/z 717.4 (M+1).

Example D22
N-(4,6-Dimethoxy-2-{[3-piperidin-1-ylpropyl)amino]-pyrimidin-5-yl}-5-[(1,1,3,3,6-pentamethyl-1,3-dihydro-2-benzofuran-5-yl)methyl]-2-furamide.

Compound D22 was synthesized according to scheme D where compound 12 was N-aminopropyl piperidine. NMR and mass spectrometry data consistent with the title product were as follows: $^1$H NMR (CDCl$_3$) δ 1.48(m, 12H), 1.66(m, 4H), 1.82(m, 2H), 2.31(s, 2H), 2.51(m, 6H), 3.44(m, 2H), 3.85(s, 6H), 3.99(s, 2H), 6.02(d, 1H, J=3.40 Hz), 6.83(s, 1H), 6.90(s, 1H), 7.08(d, 1H, 1=3.21 Hz). M/z 592.3 (M+1).

Example D23
N-{4,6-Dimethoxy-2-[(2-pyrrolidin-1-ylethyl)amino]-pyrimidin-5-yl}-5-[(1,1,3,3,6-pentamethyl-1,3-dihydro-2-benzofuran-5-yl)methyl]-2-furamide Acetate Compound D23 was synthesized according to scheme D where compound 12 was N-(2-aminoethyl)pyrrolidine. NMR and mass spectrometry data consistent with the title product were as follows: $^1$H NMR (MeOD) δ 1.48(m, 12H), 1.93(s, 3H), 2.07(m, 4H), 2.33(s, 3H), 3.39(m, 6H), 3.73(m, 2H), 3.88(s, 6H), 4.09(s, 2H), 6.05(d, 1H, J=3.21Hz), 6.97(s, 1H), 7.01(s, 1H), 7.08(d, 1H, J=3.40 Hz). M/z 564.6 (M+1).

Example D24 tert-Butyl 1-[4,6-dimethoxy-5-({5-[(1,1,3,3,6-pentamethyl-1,3-dihydro-2-benzofuran-5-yl)methyl]-2-furoyl}amino)pyrimidin-2-yl]prolinate.

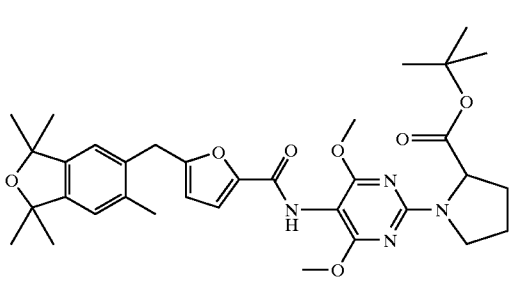

D24

Compound D24 was synthesized according to scheme D where compound 12 was H-Pro-O-tButyl (commercially available from Sigma, MFCD00037879). NMR and mass spectrometry data consistent with the title product were as follows: $^1$H NMR(MeOD) δ 1.43(s, 9H), 1.47(m, 12H), 2.02(s, 4H), 2.33(s, 3H), 2.34(s, 2H), 3.70(s, 2H), 3.88(m, 6H), 4.09(s, 2H), 4.43(t, 1H, J=2.74 Hz), 6.04(d, 1H, J=3.21 Hz), 6.97(s, 1H), 7.00(s, 1H), 7.06(d, 1H, J=3.40 Hz). M/z 620.74.

Example D25

N-{2-[(2-Furylmethyl)(2-methylprop-2-enyl)amino]-4,6-dimethoxypyrimidin-5-yl}-5-[(1,1,3,3,6-pentamethyl-1,3-dihydro-2-benzofuran-5-yl)methyl]-2-furamide

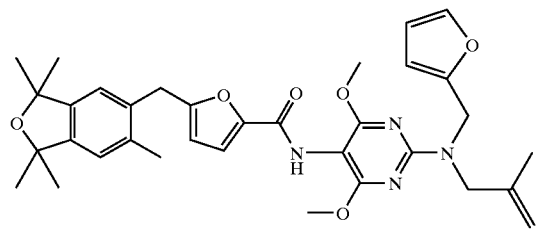

D25

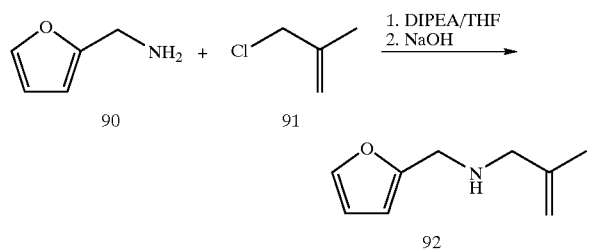

Furfurylamine 90 (376.0 g, 3.87 mol), THF (1.2 L) and di-isopropyl(ethyl)amine (DIPEA) (556.0 g, 4.3 mol, 1.1 eq) were added to a 3-necked flask, which was equipped with an overhead stirrer, a thermometer and a condensor. 3-Chloro-2-methylpropene 91 (385.7 g, 4.26 mol, 1.1 eq) was added slowly in a period of 1.5 h via a dropping funnel to the reaction mixture upon stirring at about 20° C. under nitrogen blanket. After stirring at room temperature for 18 h, the reaction mixture was heated to reflux for 18 h more. The mixture was cooled to room temperature. A solution of NaOH (400.0 g, 10.0 mol) dissolved in water (1 L) was added. The organic layer was separated, washed with brine (1×1 L), dried over Na$_2$SO$_4$ and filtered. After removing the solvent by rotary evaporation, a crude oil (497 g) was fractionally distilled to give the desired product 92 (202.4 g, 35% yield, 95% pure). Compound D25 was synthesized according to scheme D where compound 12 was compound 92. NMR and mass spectrometry data consistent with the title product were as follows: $^1$H NMR(MeOD) δ 1.47(m, 12H), 1.71(s, 3H), 2.33(s, 3H), 3.88(s, 6H), 4.09(s, 2H), 4.27(s, 2H), 4.76(s, 2H), 4.87(s, 2H), 6.04(d, 1H, J=3.40 Hz), 6.24(d, 1H, J=2.64 Hz), 6.33(s, 1H), 6.97(s, 1H), 7.00(s, 1H), 7.07(d, 1H, J=3.21 Hz), 7.39(d, 1H, J=1.70 Hz). M/z 600.71.

Example D26

N-{2-[4-(2-cyanoethyl)piperazin-1-yl]-4,6-dimethoxypyrimidin-5-yl}-5-[(1,1,3,3,6-pentamethyl-1,3-dihydro-2-benzofuran-5-yl)methyl]-2-furamide.

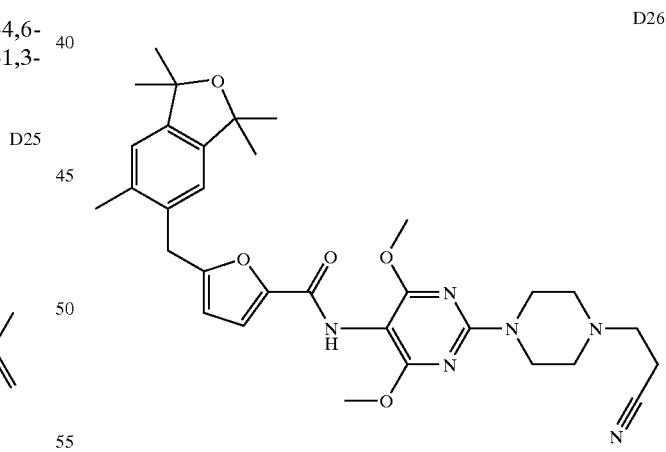

D26

Compound D26 was synthesized according to scheme D where compound 12 was 3-(1-piperazinyl)-propionitril. NMR and mass spectrometry data consistent with the title product were as follows: $^1$H NMR(MeOD) δ 1.47(m, 12H), 2.33(s, 3H), 2.56(m, 4H), 2.69(m, 4H), 3.85(m, 10H), 4.08 (s, 2H), 6.05(d, 1H, J=3.40 Hz), 6.98(s, 1H), 7.00(s, 1H), 7.07(d, 1H, J=3.40 Hz). M/z 588.71

Example D27

N-[4,6-Dimethoxy-5-({5-[(1,1,3,3,6-pentamethyl-1,3-dihydro-2-benzofuran-5-yl)methyl]-2-furoyl}amino)pyrimidin-2-yl]-N-methylglycine.

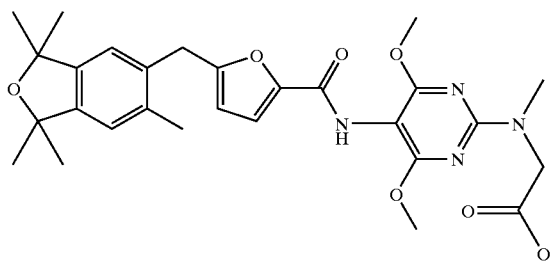

D27

Compound D27 was synthesized according to scheme D where compound 12 was sarcosine. NMR and mass spectrometry data consistent with the title product were as follows: $^1$H NMR(MeOD) δ 1.47(m, 12H), 3.23(s, 3H), 3.88(s, 6H), 4.09(s, 2H), 4.30(s, 2H), 6.05(d, 1H, J=3.21 Hz), 6.98(s, 1H), 7.00(s, 1H), 7.07(d, 1H, J=3.40 Hz). M/z 538.60

Example D28

N-{2-[(2-Bromobenzyl)amino]-4,6-dimethoxypyrimidin-5-yl}-5-[(1,1,3,3,6-pentamethyl-1,3-dihydro-2-benzofuran-5-yl)methyl]-2-furamide.

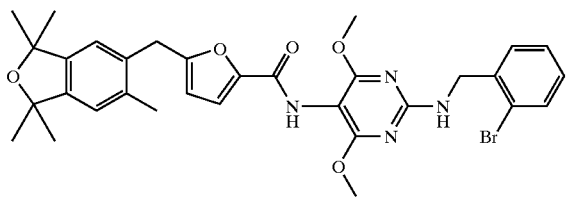

D28

Compound D28 was synthesized according to scheme D where compound 12 was 2-bromobenzylamine. NMR and mass spectrometry data consistent with the title product were as follows: $^1$H NMR(MeOD) δ 1.47(m, 12H), 2.32(s, 3H), 3.82(s, 6H), 4.09(s, 2H), 4.63(s, 2H), 6.04(d, 1H, J=3.40 Hz), 6.97(s, 1H), 6.99(s, 1H), 7.06(d, 1H, J=3.40 Hz), 7.13(td, 1H, J=1.42, 1.70 Hz), 7.28(q, 1H, J=1.07 Hz), 7.44(t, 1H, J=1.51 Hz), 7.54(t, 1H, J=1.13 Hz). M/z 635.56

Example D29

N-(4,6-Dimethoxy-2-{methyl[(6-methylpyridin-2-yl)methyl]amino}pyrimidin-5-yl)-5-[(1,1,3,3,6-pentamethyl-1,3-dihydro-2-benzofuran-5-yl)methyl]-2-furamide.

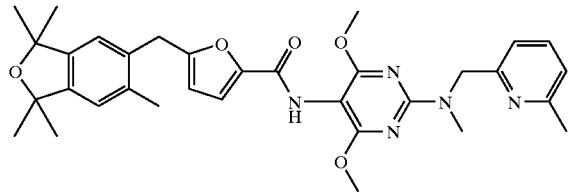

D29

Compound D29 was synthesized according to scheme D where compound 12 was 6-methyl-2-picolyl-methylamine. NMR and mass spectrometry data consistent with the title product were as follows: $^1$H NMR(MeOD) δ 1.47(m, 12H), 2.33(s, 3H), 2.52(s, 3H), 3.25(s, 3H), 3.82(s, 6H), 4.09(s, 2H), 4.92(s, 2H), 6.04(d, 1H, J=3.40 Hz) 6.98((s, 1H), 7.00(s, 1H), 7.06(s, 2H), 7.14(d, 1H, J=7.74 Hz), 7.63(t, 1H, J=7.74 Hz). M/z 585.70

Example D30

N-(2-{4-[2-(Dimethylamino)-2-oxoethyl]piperazin-1-yl}4,6-dimethoxypyrimidin-5-yl)-5-[(1,1,3,3,6-pentamethyl-1,3-dihydro-2-benzofuran-5-yl)methyl]-2-furamide

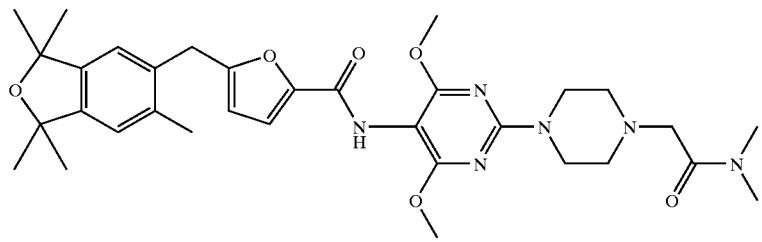

D30

Compound D30 was synthesized according to scheme D where compound 12 was piperazino-essigsaure-N,N-dimethylamide (available from Emkachem). NMR and mass spectrometry data consistent with the title product were as follows: $^1$H NMR(MeOD) δ 1.47(m, 12H), 2.33(s, 3H), 2.58(t, 8H, J=4.91 Hz), 2.95(s, 3H), 3.11(s, 3H), 3.28(s, 2H), 3.86(m, 6H), 4.09(s, 2H), 6.04(d, 1H, J=3.40 Hz), 6.98(s, 1H), 7.00(s, 1H), 7.07(d, 1H, J=3.40 Hz). M/z 620.75

Example D31

N-{2-[1,1'-Bi(cyclohexyl)-2-ylamino]4,6-dimethoxypyrimidin-5-yl}-5-[(1,1,3,3,6-pentamethyl-1,3-dihydro-2-benzofuran-2-benofuran-5-yl)methyl]-2-furamide

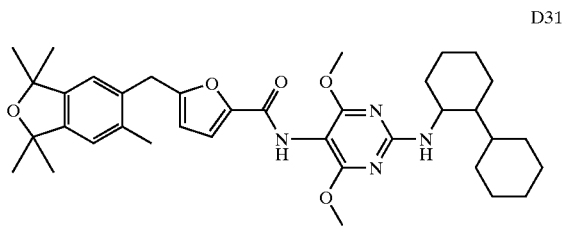

D31

Compound D31 was synthesized according to scheme D where compound 12 was O-aminobicyclohexyl. NMR and mass spectrometry data consistent with the title product were as follows: $^1$H NMR(MeOD) δ 1.09(s, 11H), 1.47(m, 12H), 1.81(s, 10H), 2.33(s, 3H), 3.85(m, 6H), 4.08(s, 2H), 6.04(d, 1H, J=3.21 Hz), 6.97(s, 1H), 7.00(s, 1H), 7.06(d, 1H, J=3.21 Hz). M/z 630.83

Example D32
N-(2-{[(1R,2R)-2-(Benzyloxy)cyclopentyl]amino}-4,6-dimethoxypyrimidin-5-yl)-5-[(1,1,3,3,6-pentamethyl-1,3-dihydro-2-benzofuran-5-yl)methyl]-2-furamide.

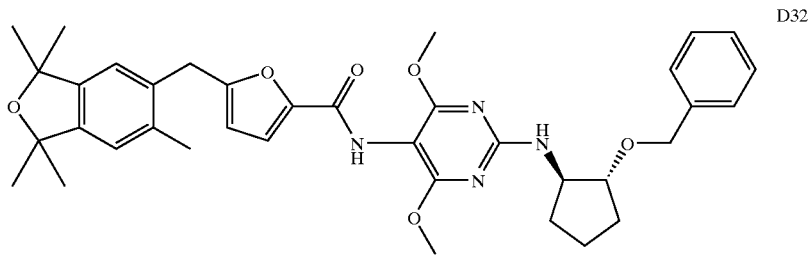

Compound D32 was synthesized according to scheme D where compound 12 was (1R,2R)-2-benzyloxycyclopentylamine. NMR and mass spectrometry data consistent with the title product were as follows: $^1$H NMR (MeOD) δ 1.48(m, 12H), 1.57(m, 2H), 1.78(m, 6H), 1.95(m, 2H), 2.17(m, 2H), 2.33(s, 3H), 3.86(s, 6H), 3.98(m, 1H), 4.09(s, 2H), 4.35(s, 1H), 4.63(dd, 2H, J=11.71, 11.90 Hz), 6.04(d, 1H, J=3.40 Hz), 6.98(s, 1H), 7.00(s, 1H), 7.07(d, 1H, J=3.40 Hz), 7.27(m, 5H). M/z 641.3 (M+1).

Example D33
N-{2-[(1-Benzylpiperidin-4-yl)amino]-4,6-dimethoxypyrimidin-5-yl}-5-[(1,1,3,3,6-pentamethyl-1,3-dihydro-2-benzofuran-5-yl)methyl]-2-furamide

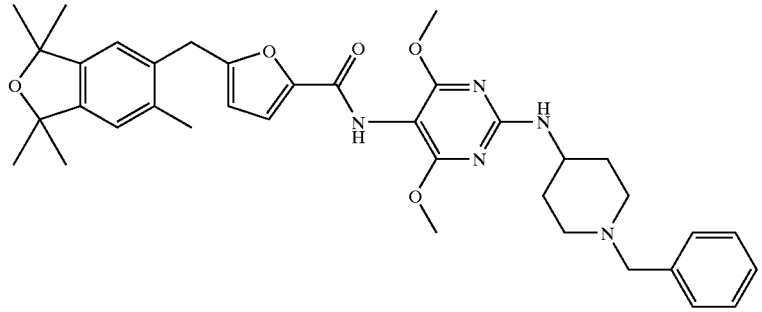

Compound D33 was synthesized according to scheme D where compound 12 was 4-amino-1-benzylpiperidine. NMR and mass spectrometry data consistent with the title product were as follows: $^1$H NMR(MeOD) δ 1.47(m, 12H), 1.71(s, 2H), 2.12(s, 4H), 2.33(s, 3H), 2.59(s, 2H), 3.11(s, 4H), 3.84(s, 6H), 3.93(s, 3H), 4.09(s, 2H), 6.05(d, 1H, J=3.40 Hz), 6.97(s, 1H), 6.99(s, 1H), 7.06(d, 1H, J=3.40 Hz), 7.38(m, 5H). M/z 639.79

Example D34
N-{4,6-Dimethoxy-2-[(3,4,5-trimethoxybenzyl)amino]-pyrimidin-5-yl}-5-[(1,1,3,3,6-pentamethyl-1,3-dihydro-2-benzofuran-5-yl)methyl]-2-furamide

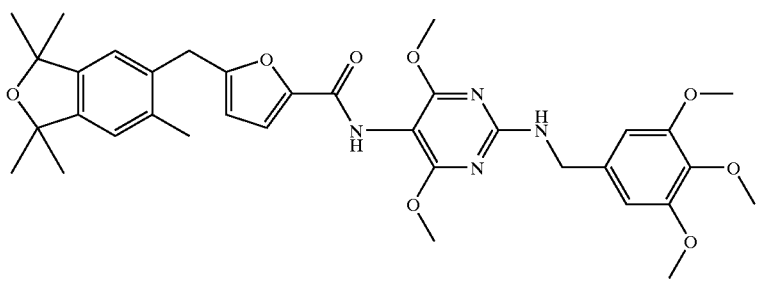

D34

Compound D34 was synthesized according to scheme D where compound 12 was 3,4,5-trimethoxy-benzylamine. NMR and mass spectrometry data consistent with the title product were as follows: $^1$H NMR (MeOD) δ 1.46(m, 12H), 2.32(s, 3H), 3.71(s, 3H), 3.79(s, 6H), 3.86(s, 6H), 4.07(s, 2H), 6.03(d, 1H, J=3.40 Hz), 6.68(s, 2H), 6.96(m, 2H), 7.06(d, 1H, J=3.40 Hz). M/z 647.3 (M+1).

Example D35
N-(2-{[2-(2-Adamantylamino)ethyl]amino}-4,6-dimethoxypyrimidin-5-yl)-5-[(1,1,3,3,6-pentamethyl-1,3-dihydro-2-benzofuran-5-yl)methyl]-2-furamide.

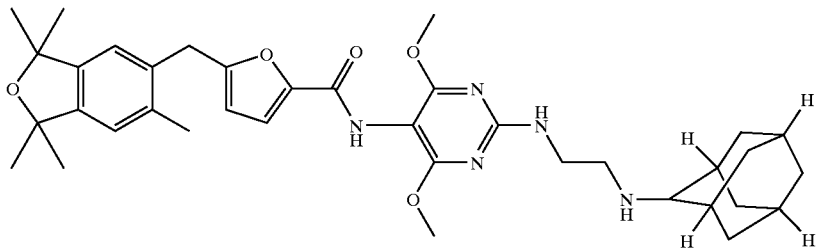

D35

Compound D35 was synthesized according to scheme D where compound 12 was N-(1-adamantyl)ethylenediamine (commercially available from TCI, MFCD02093421). NMR and mass spectrometry data consistent with the title product were as follows: $^1$H NMR(MeOD) δ 1.47(m, 12H), 1.75(s, 7H), 1.89(m, 8H), 2.33(s, 3H), 3.88(s, 6H), 4.09(s, 2H), 6.06(d, 1H, J=3.40 Hz), 6.99(m, 2H), 7.08(d, 1H, J=3.40 Hz). M/z 643.82

Example D36
N-[4,6-Dimethoxy-2-({[6-(trifluoromethyl)pyridin-3-yl]-methyl}amino)pyrimidin-5-yl]-5-[(1,1,3,3,6-pentamethyl-1,3-dihydro-2-benzofuran-5-yl)methyl]-2-furamide.

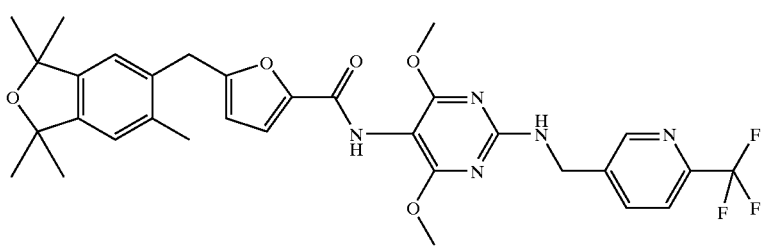

D36

Compound D36 was synthesized according to scheme D where compound 12 was 3-aminomethyl-6-(trifluoromethyl)pyridine. NMR and mass spectrometry data consistent with the title product were as follows: $^1$H NMR (MeOD) δ 1.47(m, 12H), 2.32(s, 3H), 3.81(s, 6H), 4.08(s, 2H), 4.65(s, 2H), 6.03(d, 1H, J=3.40 Hz), 6.97(s, 1H), 6.99(s, 1H), 7.06(d, 1H, J=3.40 Hz), 7.75(d, 1H, J=7.93 Hz), 8.03(d, 1H, J=9.44 Hz), 8.72(s, 1H). M/z 625.65

Example D37
N-{2-[Butyl(2-cyanoethyl)amino]-4,6-dimethoxypyrimidin-5-yl}-5-[(1,1,3,3,6-pentamethyl-1,3-dihydro-2-benzofuran-5-yl)methyl]-2-furamide.

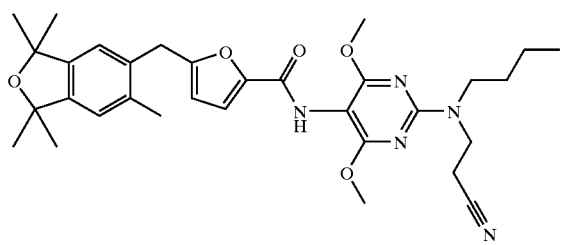

Compound D37 was synthesized according to scheme D where compound 12 was 3-(butylamino)-propionitrile. NMR and mass spectrometry data consistent with the title product were as follows: $^1$H NMR (MeOD) δ 0.93(m, 3H), 1.37(m, 2H), 1.47(m, 12H), 2.33(s, 3H), 2.84(m, 2H), 3.67 (m, 2H), 3.85(m, 2H), 3.90(s, 6H), 4.10(s, 2H), 6.05(d, 1H, J=3.40 Hz), 6.99(m, 2H), 7.08(d, 1H, J=3.40 Hz). M/z 576.3 (M+1).

Example D38
N-{4,6-Dimethoxy-2-[methyl(pyridin-3-ylmethyl)amino] pyrimidin-5-yl}-5-[(1,1,3,3,6-pentamethyl-1,3-dihydro-2-benzofuran-5-yl)methyl]-2-furamide.

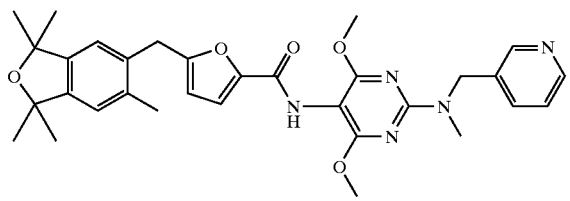

Compound D38 was synthesized according to scheme D where compound 12 was 3-picolylmethylamine. NMR and mass spectrometry data consistent with the title product were as follows: $^1$H NMR (MeOD) δ 1.47(m, 12H), 2.32(s, 31H), 3.21(s, 3H), 3.86(s, 6H), 4.09(s, 2H), 4.93(s, 2H), 6.04(d, 1H, J=3.40 Hz), 6.97(m, 2H), 7.08(d, 1H, J=3.40 Hz), 7.40(m, 1H), 7.77(d, 1H, J=7.93 Hz), 8.42(d, 1H, J=4.53 Hz), 8.53(s, 1H). M/z 572.2 (M+1).

Example D39
N-[2-({3-[(2-Ethylhexyl)oxy]propyl}amino)-4,6-dimethoxypyrimidin-5-yl]-5-[(1,1,3,3,6-pentamethyl-1,3-dihydro-2-benzofuran-5-yl)methyl]-2-furamide

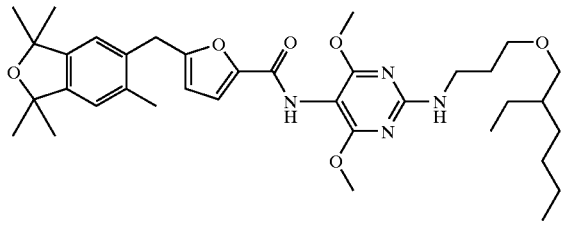

Compound D39 was synthesized according to scheme D where compound 12 was 3-(2-ethylhexyloxy)propylamine. NMR and mass spectrometry data consistent with the title product were as follows: $^1$H NMR (MeOD) δ 0.89(m, 6H), 1.33(m, 6H), 1.47(m, 12H), 1.85(m, 2H), 2.31(s, 3H) 3.34 (m, 2H), 3.45(m, 2H), 3.52(m, 2H), 3.86(s, 6H), 4.08(s, 2H), 6.04(d, 1H, J=3.21 Hz), 6.97(m, 2H), 7.06(d, 1H, J=3.21 Hz). M/z 637.4 (M+1).

Example D40
N-[4,6-Dimethoxy-2-(3-oxooctahydro-5H-pyrrolo[3,4-c] pyridin-5-yl)pyrimidin-5-yl]-5-[(1,1,3,3,6-pentamethyl-1,3-dihydro-2-benzofuran-5-yl)methyl]-2-furamide.

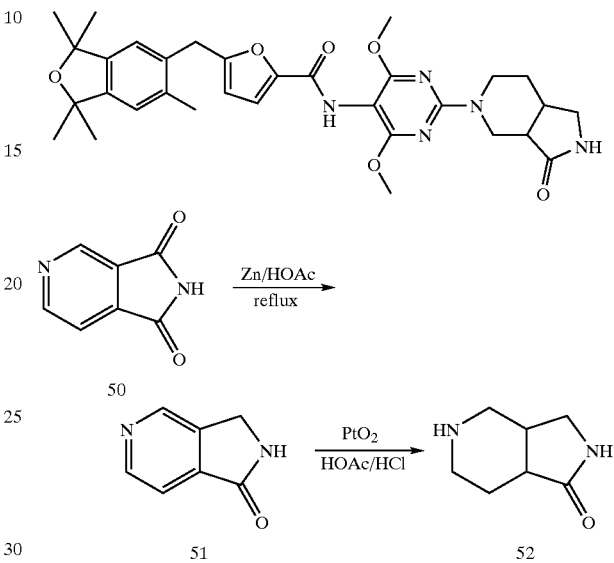

Dihydro-pyrrolopyridinone, compound 51 was prepared by reduction of 3,4-pyridinedicaboximide, compound 50, with zinc in glacial acetic acid. Octane-3H-pyrrolo[3,4-c]-pyridin-3-one hydrochloride, compound 52, was prepared by hydrogenation of, compound 51 using platinum (IV) oxide as a catalyst and subsequence acidification with 4N HCL in dioxane. Compound D40 was synthesized according to scheme D where compound 12 was compound 52. NMR and mass spectrometry data consistent with the title product were as follows: $^1$H NMR(MeOD) δ 1.47(m, 12H), 1.61(s, 2H), 1.95(s, 2H), 2.33(s, 3H), 2.69(s, 2H), 3.09(dd, 1H, J=2.64, 2.27 Hz), 3.23(s, 2H), 3.53(s, 2H), 3.90(s, 6H), 4.09(s, 2H), 4.25(s, 2H), 4.65(dd, 1H, J=3.59, 3.02 Hz), 6.04(d, 1H, J=3.40 Hz), 6.98(s, 1H), 7.00(s, 1H), 7.06(d, 1H, J=3.40 Hz). M/z 589.69 (M+1).

Example D41
N-{2-[(6-Hydroxyhexyl)(methyl)amino]-4,6-dimethoxypyrimidin-5-yl}-5-[(1,1,3,3,6-pentamethyl-1,3-dihydro-2-benzofuran-5-yl)methyl]-2-furamide.

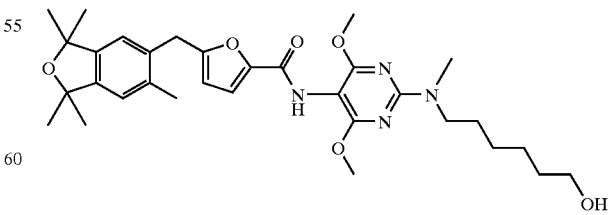

Compound D41 was synthesized according to scheme D where compound 12 was 6-methylaminohexanol. NMR and mass spectrometry data consistent with the title product were as follows: $^1$H NMR(MeOD) δ 1.37(m, 4H), 1.47(m, 12H), 1.53(m, 2H), 1.66(m, 2H), 2.33(s, 3H), 3.14(s, 3H), 3.53(t, 2H, J=6.61 Hz), 3.63(t, 2H, J=7.27 Hz), 3.87(s, 6H), 4.09(s, 2H), 6.04(d, 1H, J=3.40 Hz), 6.98(s, 1H), 7.00(s, 1H), 7.06(d, 1H, J=3.40 Hz). M/z 580.72 (M+1).

Example D42

N-[2-({2-[(2-Hydroxyethyl)thio]ethyl}amino)-4,6-dimethoxypyrimidin-5-yl]-5-[(1,1,3,3,6-pentamethyl-1,3-dihydro-2-benzofuran-5-yl)methyl]-2-furamide.

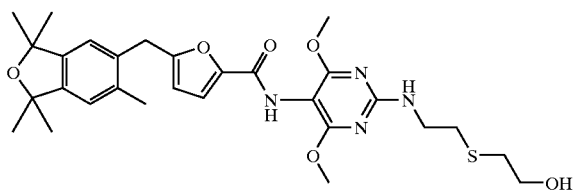

D42

Compound D42 was synthesized according to scheme D where compound 12 was 2 ((2-aminoethyl)-thio)-ethanol. NMR and mass spectrometry data consistent with the title product were as follows: $^1$H NMR (MeOD) δ 1.39(m, 12H), 2.20(s, 3H), 2.60(t, 2H, J=6.80 Hz), 2.69(m, 2H), 3.46(m, 2H), 3.59(t, 2H, J=6.80 Hz), 3.76(s, 6H), 4.00(s, 2H), 5.93(d, 1H, J=3.40 Hz), 6.89(m, 2H), 6.98(d, 1H, J=3.40 Hz). M/z 571.2(M+1).

Example D43

N-{2-[4-(2-Fluorophenyl)piperazin-1-yl]-4,6-dimethoxypyrimidin-5-yl}-5-[(1,1,3,3,6-pentamethyl-1,3-dihydro-2-benzofuran-5-yl)methyl]-2-furamide.

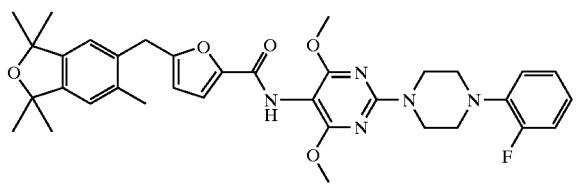

D43

Compound D43 was synthesized according to scheme D where compound 12 was 1-(2-fluorophenyl)piperazine. NMR and mass spectrometry data consistent with the title product were as follows: $^1$H NMR(MeOD) δ 1.48(m, 12H), 2.33(s, 3H), 3.11(t, 4H, J=4.91 Hz), 3.89(s, 6H), 3.99(t, 4H, J=5.00 Hz), 4.10(s, 2H), 6.06(d, 1H, J=3.40 Hz), 7.03(s, 7H). M/z 629.73 (M+1).

Example D44

N-{2-[(4-Aminobenzyl)amino]-4,6-dimethoxypyrimidin-5-yl}-5-[(1,1,3,3,6-pentamethyl-1,3-dihydro-2-benzofuran-5-yl)methyl]-2-furamide.

D44

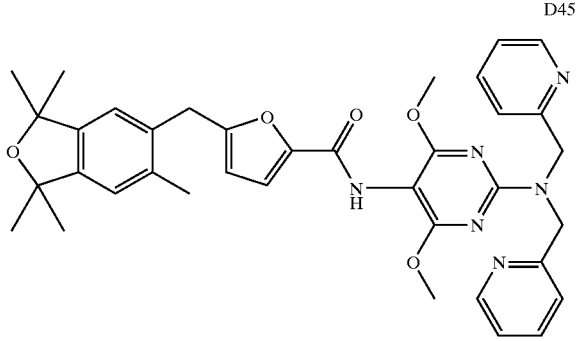

Compound D44 was synthesized according to scheme D where compound 12 was 4-aminobenzylamine. NMR and mass spectrometry data consistent with the title product were as follows: $^1$H NMR(MeOD) δ 1.47(m, 12H), 2.32(s, 3H), 3.85(s, 6H), 4.08(s, 2H), 4.42(s, 2H), 6.04(d, 1H, J=3.40 Hz), 6.67(d, 2H, J=8.31 Hz), 6.97(s, 1H), 7.00(s, 1H), 7.06(d, 1H, J=3.40 Hz), 7.11(d, 2H, J=8.31 Hz). M/z 571.67 (M+1).

Example D45

N-{2-[Bis(pyridin-2-ylmethyl)amino]-4,6-dimethoxypyrimidin-5-yl}-5-[(1,1,3,3,6-pentamethyl-1,3-dihydro-2-benzofuran-5-yl)methyl]-2-furamide.

D45

Compound D45 was synthesized according to scheme D where compound 12 was di-(2-picolyl)amine. NMR and mass spectrometry data consistent with the title product were as follows: $^1$H NMR(MeOD) δ 1.44(m, 12H), 2.29(s, 3H), 3.57(s, 6H), 4.05(s, 2H), 5.26(s, 4H), 6.03(d, 1H, J=3.40 Hz), 6.95(s, 2H), 7.02(d, 1H, J=3.40 Hz), 7.67(t, 2H, J=6.42 Hz), 7.87(d, 2H, J=7.93 Hz), 8.22(dd, 2H, J=7.93, 7.55 Hz), 8.87(d, 2H, J=4.91 Hz). M/z 648.76 (M+1).

Example D46

N-{4,6-Dimethoxy-2-(4-(2-morpholin-4-ylethyl)piperazin-1-yl]pyrimidin-5-yl}-5-[(1,1,3,3,6-pentamethyl-1,3-dihydro-2-benzofuran-5-yl)methyl]-2-furamide.

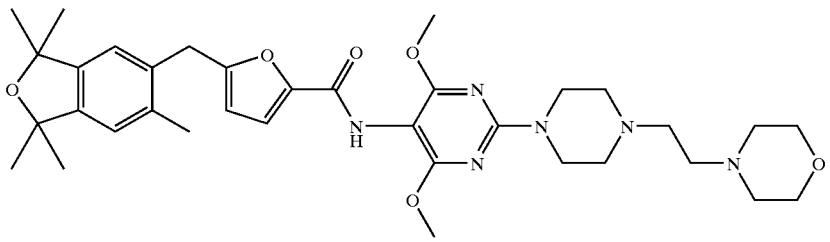

Compound D46 was synthesized according to scheme D where compound 12 was 1-(2-morpholinoethyl)-peperazine. NMR and mass spectrometry data consistent with the title product were as follows: $^1$H NMR(MeOD) δ 1.47(m, 12H), 2.32(s, 3H), 2.63(m, 12H), 3.71(t, 4H, J=4.53 Hz), 3.87(s, 10H), 4.09(s, 2H), 6.05(d, 1H, J=3.40 Hz), 6.97(s, 1H), 7.00(s, 1H), 7.07(d, 1H, J=3.40 Hz). M/z 648.80 (M+1).

Example D47

N-{2-[[2-(Dimethylamino)ethyl](4-fluorobenzyl)amino]-4,6-dimethoxypyrimidin-5-yl}-5-[(1,1,3,3,6-pentamethyl-1,3-dihydro-2-benzofuran-5-yl)methyl]-2-furamide.

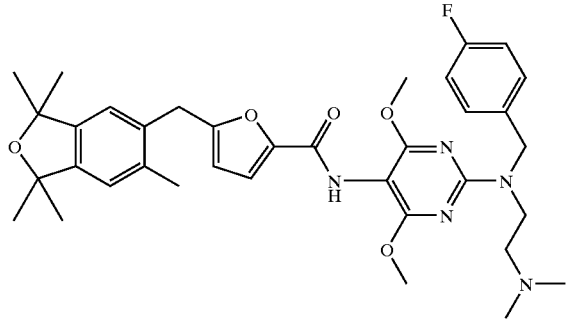

Compound D47 was synthesized according to scheme D where compound 12 was synthesized according to the procedure set forth in the *J. Chem. Soc.*, 1908–18 (1961). NMR and mass spectrometry data consistent with the title product were as follows: $^1$H NMR (MeOD) δ 1.42(m, 12H), 2.28(s, 3H), 2.45(s, 6H), 2.75(t, 2H, J=7.05 Hz), 3.75(m, 2H), 3.83(s, 6H), 4.05(s, 2H), 4.84(s, 2H), 6.00(d, 1H, J=3.40 Hz), 6.94(m, 2H), 6.99(m, 2H), 7.04(d, 1H, J=3.40 Hz), 7.30(m, 2H). M/z 646.3 (M+1).

Example D48

N-{2-[(4-Ethylbenzyl)(3-hydroxypropyl)amino]-4,6-dimethoxypyrimidin-5-yl}-5-[(1,1,3,3,6-pentamethyl-1,3-dihydro-2-benzofuran-5-yl)methyl]-2-furamide

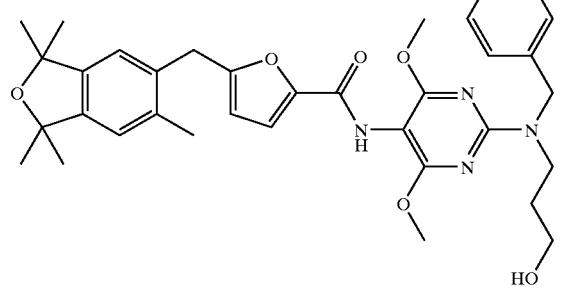

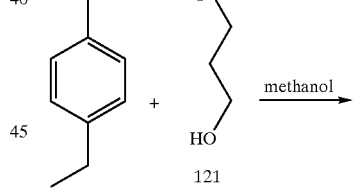

A solution of compound 120 in methanol (0.1M) was prepared. A solution of compound 121 in methanol (0.1M) was prepared and added to the solution of compound 120, 1 eq of each. Reaction was left to stir overnight. A 0.5M solution of NaBH$_4$ in ethanol was prepared. Two equivalents (eq) of NaBH₄ solution was added to reaction mixture and the reaction mixture was allow to stir for 2 hours. Once complete the mixture was quenched with water and the organic solvents were removed via Rotovap. A 6:3:1 ethyl acetate/methylene chloride/methanol mixture was used to extract the product from the water layer. The organic layer was then dried using a sodium sulfate plug, then concentrated to give compound 122. Compound D48 was synthesized according to scheme D where compound 12 was compound 122. NMR and mass spectrometry data consistent with the title product were as follows: ¹H NMR (MeOD) δ 1.15(t, 3H, J=7.75 Hz), δ 1.43(m, 12H), 1.82(m, 2H), 2.28(s, 3H), 2.54(q, 2H, J=7.55 Hz), 3.54(M 2H), 3.63(t, 2H, J=7.18 Hz), 3.81(s, 6H), 4.05(s, 2H), 4.81(s, 2H), 6.00(d, 1H, J=3.40 Hz), 6.94(m, 2H), 7.02(d, 1H, J=3.40 Hz), 7.08(d, 2H, J=7.93 Hz), 7.16(d, 2H, J=7.93 Hz). M/z 643.3 (M+1).

Example D49

N-{2-[Bis(2-ethoxyethyl)amino]-4,6-dimethoxypyrimidin-5-yl}-5-[(1,1,3,3,6-pentamethyl-1,3-dihydro-2-benzofuran-5-yl)methyl]-2-furamide.

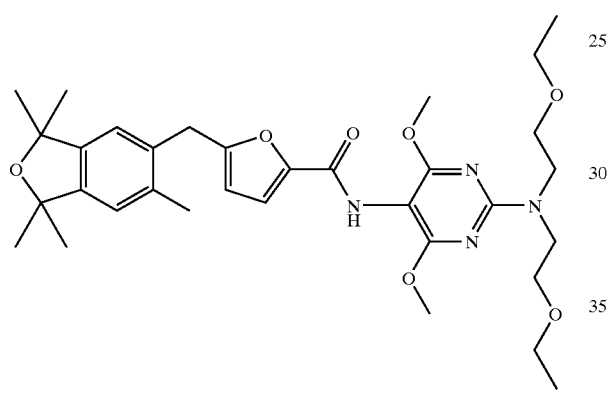

D49

Compound D49 was synthesized according to scheme D where compound 12 was bis(2-ethoxyethyl)amine. NMR and mass spectrometry data consistent with the title product were as follows: ¹H NMR (MeOD) δ 1.17(t, 3H, J=6.99 Hz), 61.47(m, 12H), 2.33(s, 3H), 3.51(q, 4H, J=7.05 Hz), 3.68(m, 4H), 3.81(m, 4H), 3.87(s, 6H), 4.09(s, 2H), 4.81(s, 2H), 6.04(d, 1H, J=3.40 Hz), 6.99(m, 2H), 7.07(d, 1H, J=3.40 Hz). M/z 611.3 (M+1).

Example D50

N-(2-{[(1S)-2-(Benzylthio)-1-(hydroxymethyl)ethyl]amino}-4,6-dimethoxypyrimidin-5-yl)-5-[(1,1,3,3,6-pentamethyl-1,3-dihydro-2-benzofuran-5-yl)methyl]-2-furamide.

Compound D50 was synthesized according to scheme D where compound 12 was S-benzyl-L-cysteinol. NMR and mass spectrometry data consistent with the title product were as follows: ¹H NMR (MeOD) δ 1.47(m, 12H), 2.33(s, 3H), 2.72(m, 2H), 3.69(m, 2H), 3.78(s, 2H), 3.84(s, 6H), 4.09(s, 2H), 4.19(s, 1H), 4.19(m, 1H), 6.05(d, 1H, J=3.40 Hz), 6.98(s, 1H), 7.00(s, 1H), 7.07(d, 1H, J=3.40 Hz), 7.24(m, 5H). M/z 647.2 (M+1).

Example D51

Ethyl N-benzyl-N-[4,6-dimethoxy-5-({5-[(1,1,3,3,6-pentamethyl-1,3-dihydro-2-benzofuran-5-yl)methyl]-2-furoyl}amino)pyrimidin-2-yl]glycinate.

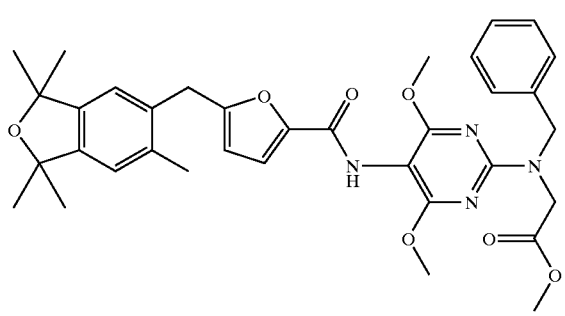

D51

Compound D51 was synthesized according to scheme D where compound 12 was N-benzyglycine ethyl ester. NMR and mass spectrometry data consistent with the title product were as follows: ¹H NMR(MeOD) δ 1.21 (t, 3H, J=7.18 Hz), 1.46(m, 12H), 2.32(s, 3H), 3.83(s, 6H), 4.08(s, 2H), 4.15(q, 2H, J=7.18, Hz), 4.23(s, 2H), 4.94(s, 2H), 6.05(d, 1H, J=3.02 Hz), 6.98(m, 2H), 7.07(d, 1H, J=3.40 Hz), 7.29(m, 5H). M/z 642.75 (M+1).

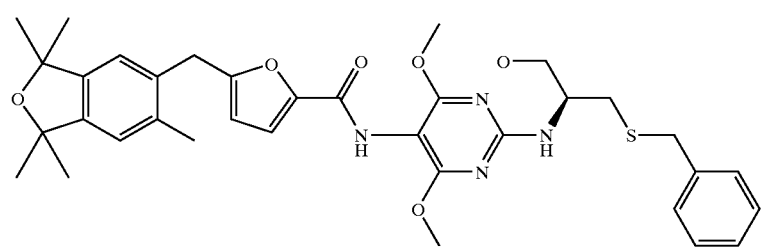

D50

Example D52

N-{4,6-Dimethoxy-2-[4-(2-methoxyphenyl)piperidin-1-yl]pyrimidin-5-yl}-5-[(1,1,3,3,6-pentamethyl-1,3-dihydro-2-benzofuran-5-yl)methyl]-2-furamide.

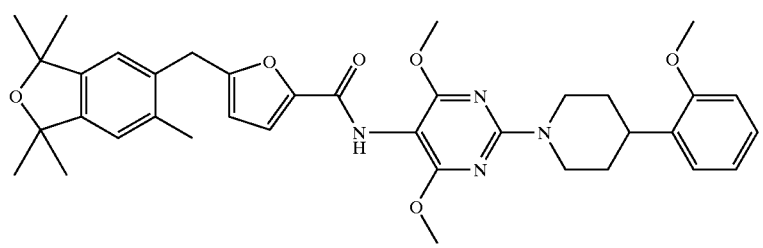

Compound D52 was synthesized according to scheme D where compound 12 was 4-(2-methoxyphenyl)piperidine. NMR and mass spectrometry data consistent with the title product were as follows: $^1$H NMR(MeOD) δ 1.47(m, 12H), 1.64(tt, 4H, J=3.78, 3.40 Hz), 1.83(d, 4H, J=12.09 Hz), 2.33(s, 3H), 2.96(dd, 4H, J=12.84, 11.71 Hz), 3.23(s, 1H), 3.82(s, 3H), 3.88(s, 6H), 4.09(s, 2H), 4.93(d, 4H, J=12.84 Hz), 6.04(d, 1H, J=3.02 Hz), 6.89(ddd, 2H, J=10.20, 7.93, 7.55 Hz), 6.98(s, 1H), 7.00(s, 1H), 7.07(d, 1H, J=3.40 Hz), 7.15(dd, 2H, J=8.69, 8.31 Hz). M/z 640.78 (M+1).

Example D53

N-{2-[Bis(2-hydroxypropyl)amino]-4,6-dimethoxypyrimidin-5-yl)-5-[(1,1,3,3,6-pentamethyl-1,3-dihydro-2-benzofuran-5-yl)methyl]-2-furamide.

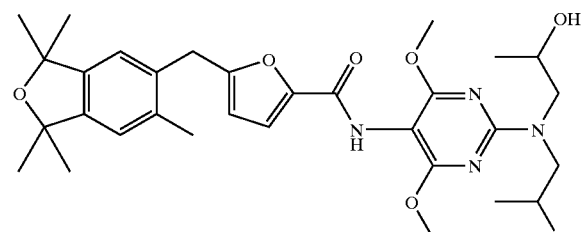

Compound D53 was synthesized according to scheme D where compound 12 was diisopropanolamine. NMR and mass spectrometry data consistent with the title product were as follows: $^1$H NMR (MeOD) δ 1.18(m, 6H), 1.47(m, 12H), 2.33(s, 3H), 3.51(m, 2H), 3.82(m, 2H), 3.86(s, 6H), 4.09(s, 2H), 4.22(m, 2H), 6.05(d, 1H, J=3.21 Hz), 6.98(s, 1H), 7.00(s, 1H), 7.07(d, 1H, J=3.21 Hz). M/z 583.2 (M+1).

Example D54

N-{4,6-Dimethoxy-2-[4-(pyridin-4-ylmethyl)piperazin-1-yl]pyrimidin-5-yl}-5-[(1,1,3,3,6-pentamethyl-1,3-dihydro-2-benzofuran-5-yl)methyl]-2-furamide.

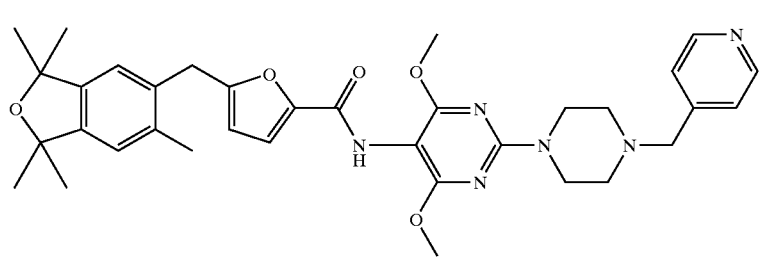

Compound D54 was synthesized according to scheme D where compound 12 was 1-(4-pyridylmethyl)-piperazine. NMR and mass spectrometry data consistent with the title product were as follows: $^1$H NMR(MeOD) δ 1.47(m, 12H), 2.33(s, 3H), 2.54(t, 4H, J=5.00 Hz), 3.64(s, 2H), 3.86(m, 10H), 4.09(s, 2H), 6.04(d, 1H, J=3.59 Hz), 6.98(s, 1H), 7.00(s, 1H), 7.07(d, 1H, J=3.59 Hz), 7.49(d, 2H, J=5.10 Hz), 8.50(s, 2H). M/z 626.75 (M+1).

Example D55

N-{2-[(1,1'-Biphenyl-4-ylmethyl)amino]-4,6-dimethoxypyrimidin-5-yl}-5-[(1,1,3,3,6-pentamethyl-1,3-dihydro-2-benzofuran-5-yl)methyl]-2-furamide.

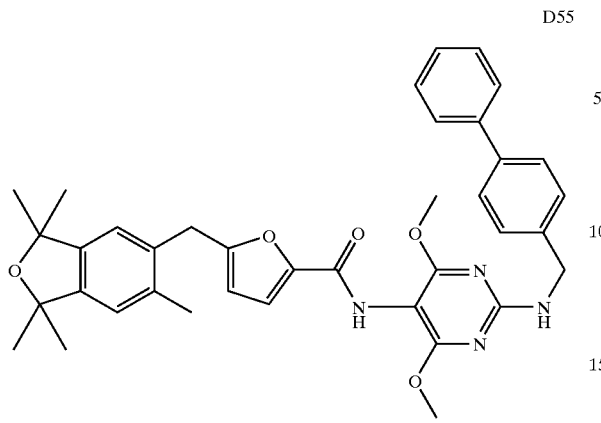

Compound D55 was synthesized according to scheme D where compound 12 was 4-phenylbenzylamine. NMR and mass spectrometry data consistent with the title product were as follows: $^1$H NMR (MeOD) δ 1.47(m, 12H), 2.32(s, 3H), 3.84(s, 6H), 4.08(s, 2H), 4.60(s, 2H), 6.03(d, 1H, J=3.40 Hz), 6.98(m, 2H), 7.06(d, 1H, J=3.40 Hz), 7.29(t, 1, J=7.37 Hz), 7.42(m, 4H), 7.57(m, 3H). M/z 633.3 (M+1).

Example D56
N-(2-{[(4-Hydroxy-1-methylpiperidin-4-yl)methyl]amino}-4,6-dimethoxypyrimidin-5-yl)-5-[(1,1,3,3,6-pentamethyl-1,3-dihydro-2-benzofuran-5-yl)methyl]-2-furamide Acetate.

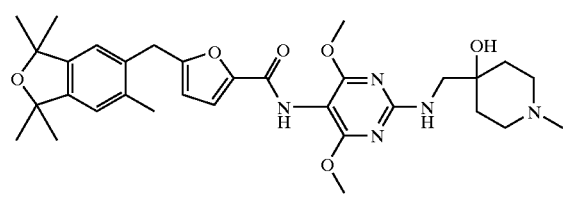

Compound D56 was synthesized according to scheme D where compound 12 was synthesized according to the procedure set forth in *J. Med. Chem* 13(2), 305–8 (1970). NMR and mass spectrometry data consistent with the title product were as follows: $^1$H NMR (MeOD) δ 1.44(m, 12H), 1.73(s, 4H), 2.28(s, 3H), 2.52(s, 3H), 2.86(s, 4H), 3.43(s, 2H), 3.82(s, 6H), 4.05(s, 2H), 6.01(d, 1H, J=3.40 Hz), 6.93(s, 1H), 6.95(s, 1H), 7.03(d, 1H, J=3.40 Hz). M/z 594.3 (M+1).

Example D57
N-(4,6-Dimethoxy-2-{[3,3,3-trifluoro-2-(1H-pyrrol-2-yl)propyl]amino}pyrimidin-5-yl)-5-[(1,1,3,3,6-pentamethyl-1,3-dihydro-2-benzofuran-5-yl)methyl]-2-furamide.

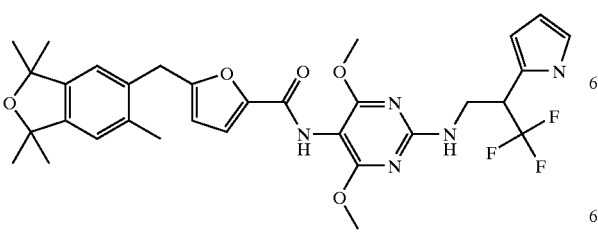

Compound D57 was synthesized according to scheme D where compound 12 was 3,3,3-trifluoro-2-(1H-pyrrol-2-yl)propylamine. NMR and mass spectrometry data consistent with the title product were as follows: $^1$H NMR (MeOD) δ 1.43(m, 12H), 2.28(s, 3H), 3.61(s, 1H), 3.80(s, 6H), 4.05(s, 2H), 5.99(d, 1H, J=3.40 Hz), 6.03(m, 1H), 6.07(m, 1H), 6.65(m, 1H), 6.94(m, 2H), 7.03(d, 1H, J=3.40 Hz). M/z 628.2 (M+1).

Example D58

N-[2-({2-[(5-Hydroxypentyl)(methyl)amino]ethyl}amino)-4,6-dimethoxypyrimidin-5-yl]-5-[(1,1,3,3,6-pentamethyl-1,3-dihydro-2-benzofuran-5-yl)methyl]-2-furamide.

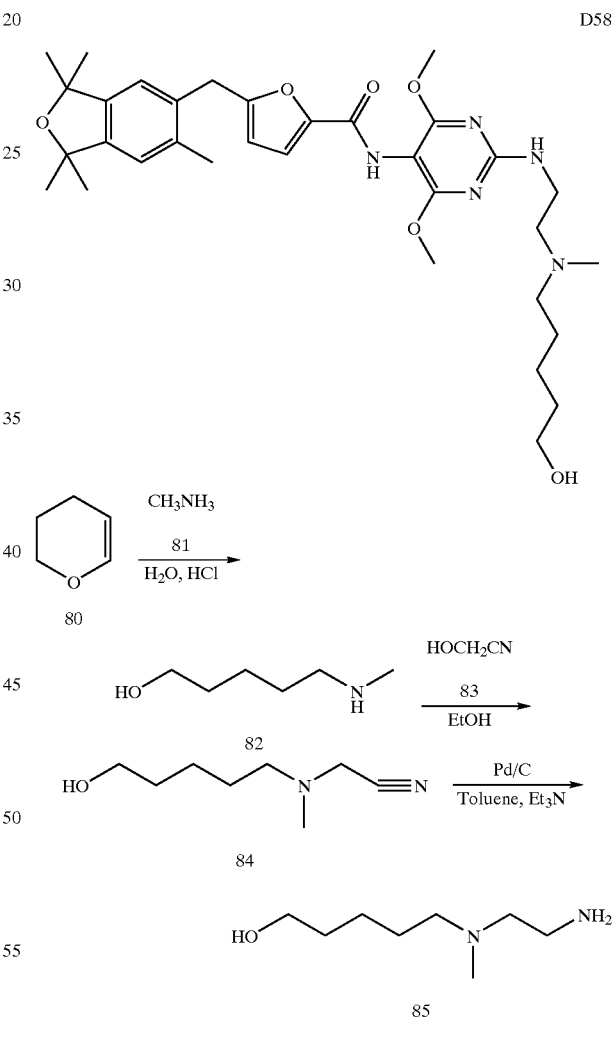

Compound 82 was made by combining compounds 80 and 81 according to the procedure set forth in *Bull. Soc. Chim. Fr.*, 14, 455 (1947). Compound 82 was dissolved in EtOH and heated to reflux with stirring. Compound 83 was then added dropwise and the resulting solution was refluxed for an additional hour. The reaction mixture was then cooled to filtered. The reaction mixture was washed with ether and the filtrated was concentrated and vacuum distilled. Boiling point: 163–165° C./13.8 mm. Compound 84 was combined with Pd/C, toluene and triethylamine. Hydrogen was added, and once the reaction was complete, the slurry was filtered and then concentrated. The product, compound 85, was purified by distillation. Boiling point: 161–163° C./13.5 mm. Compound D58 was synthesized according to scheme D where compound 12 was compound 85. NMR and mass spectrometry data consistent with the title product were as follows: $^1$H NMR (MeOD) δ 1.32(s, 1H), 1.42(m, 12H), 1.55(m, 4H), 2.29(s, 3H), 2.45(s, 3H), 2.62(m, 2H), 2.81(t, 2H, J=6.70 Hz), 3.51(m, 4H), 3.83(s, 6H), 4.06(s, 2H), 6.00(d, 1H, J=3.40 Hz), 6.95(m, 2H), 7.03(d, 1H, J=3.40 Hz). M/z 610.3 (M+1).

Example D59
N-{2-[2-(Dimethylamino)-7,8-dihydropyrido[4,3-d]pyrimidin-6(5H)-yl]-4,6-dimethoxypyrimidin-5-yl}-5-[(1,1,3,3,6-pentamethyl-1,3-dihydro-2-benzofuran-5-yl)methyl]-2-furamide.

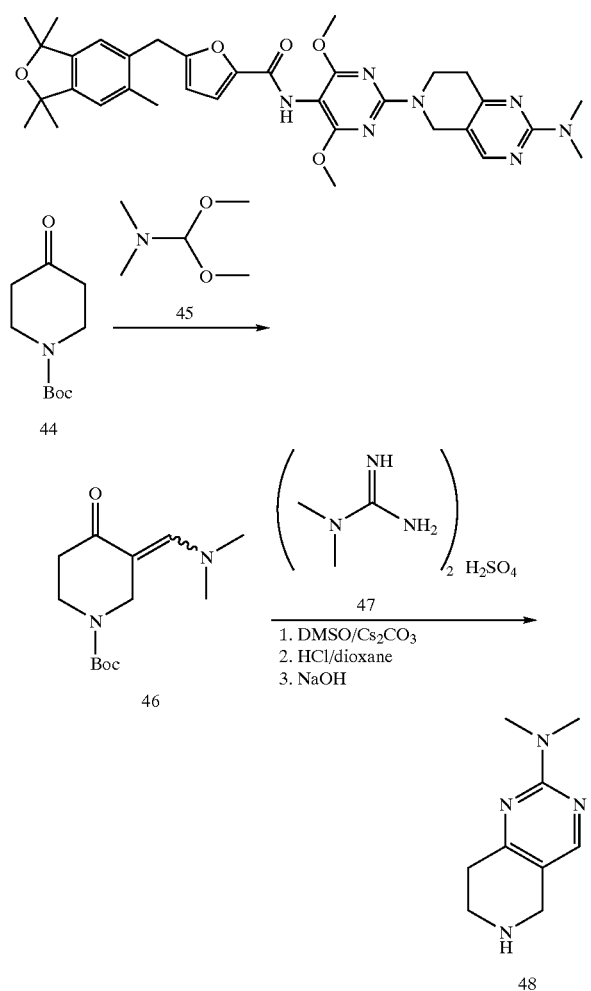

Tert-butyl 4-oxopiperidine-1-carboxylate, compound 44 (270.6 g, 1.36 mol), was added to a 2-L flask, which was equipped with a stir bar, thermometer and a condensor. N,N-Dimethylformamide dimethyl acetal, compound 45 (374.4 g, 1.88 mol. 1.3 mol eq); which was used a solvent and a reagent, was then added to the reaction flask. The reaction mixture was heated on an oil bath to reflux at 86° C. for 140 min. The volatile material was removed by rotary evaporation. A crude material (385.7 g) was obtained and purified by gradient column chromatography using hexane/ethylacetate (20–100%). The good fractions were collected, and the solvent was removed by rotary evaporation to give the desired product, compound 46 (58.8 g, 18% yield, 95% pure). TLC R$_f$=0.30 [ethylacetate:methanol (9:1)]; $^1$H NMR (300 MHz, CDCl$_3$) δ 7.50 (s, 1H, CH ethylene), 4.52 (s, 2H), 3.58 (t, J=6.0 Hz, 2H), 3.10 (s, 6H, N—(CH$_3$)$_2$), 2.44 (t, J=6.0 Hz, 2H), 1.45 (s, 9H, Boc-CH$_3$). GC-MS: 197 m/z [M-(t-butyl)$^+$]. A second fraction of the product was collected for use in the next step (79.0 g, 30% yield, 80% pure). 1,1-Dimethylguanidine sulfate, compound 47 (23.4 g, 0.086 mol, 0.55 mol eq), Cs$_2$CO$_3$ (56.0 g, 0.172 mol, 1.1 eq), compound 46 (40.0 g, 0.157 mol), and DMSO (80.0 mL) were added to a 500 mL-flask, which was equipped with a thermometer, stir bar and a condensor. The reaction mixture was heated on an oil bath at 80° C. for 32 h. After cooling to room temperature, water (500 mL) was added, and the organic material was extracted with CH$_2$Cl$_2$ (4×500 mL). The combined organic layer was washed with water (3×250 mL), dried over Na$_2$SO$_4$ and filtered. After removing the organic solvent by rotary evaporation, thick yellow oil was obtained and solidified. The product was identified by $^1$H NMR as the Boc-product 47 (41.3 g, 95% yield, 95% pure). The Boc-product, compound 47 (31.1 g, 0.112 mol), was added to HCl (4 M) in 1,4-dioxane and stirred at room temperature for 20 h. The volatile material was removed by rotary evaporation, and the residue was neutralized with 100 mL of water/NaOH (50% w/v). The free-base product was extracted with CH$_2$Cl$_2$ (4×200 mL), washed with brine (2×100 mL), dried over Na$_2$SO$_4$ and filtered. After removing the solvent by rotary evaporation, a white solid was obtained as compound 47 (18.5 g, 93% yield, 95% pure). Compound D59 was synthesized according to scheme D where compound 12 was compound 47. NMR and mass spectrometry data consistent with the title product were as follows: $^1$H NMR (MeOD) δ 1.46(m, 12H), 2.31(s, 3H), 2.89(m, 2H), 3.18(s, 6H), 3.92(s, 6H), 4.08(s, 2H), 4.14(m, 2H), 4.81(s, 2H), 6.06(d, 1H, J=3.40 Hz), 6.98(m 2H), 7.09(d, 1H, J=3.02 Hz), 8.20(s, 1H). M/z 628.3 (M+1).

Example D60
N-(4,6-Dimethoxy-2-{[3-(methylamino)propyl]amino}-5-pyrimidinyl)-5-[(1,1,3,3,6-pentamethyl-1,3-dihydro-2-benzofuran-5-yl)methyl]-2-furamide.

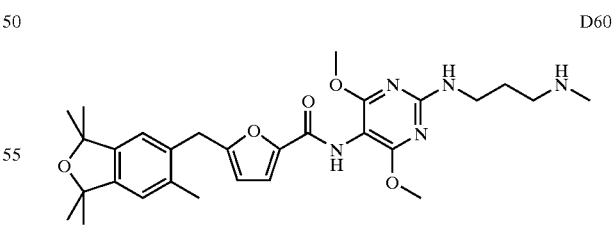

Compound D60 was synthesized according to scheme D where compound 12 was N-methyl-1,3-propanediamine. NMR and mass spectrometry data consistent with the title product were as follows: $^1$H NMR (MeOD) δ 1.47(m, 12H), 1.81(q, 4H, J=7.08 Hz), 2.33(s, 3H), 2.54(m, 12H), 2.98(t, 2H, J=7.18 Hz), 3.42(t, 2H, J=6.52 Hz), 3.86(s, 6H), 4.09(s, 2H), 6.05(d, 1H, J=3.40 Hz), 6.98(s, 1H), 7.00(s, 1H), 7.06(d, 1H, J=3.40 Hz). M/z 650.4 (M+1).

Example D61
N-(4,6-dimethoxy-2-{4-[2-(trinfluoromethyl)quinolin-4-yl]piperazin-1-yl}pyrimidin-5-yl)-5-[(1,1,3,3,6-pentamethyl-1,3-dihydro-2-benzofuran-5-yl)methyl]-2-furamide.

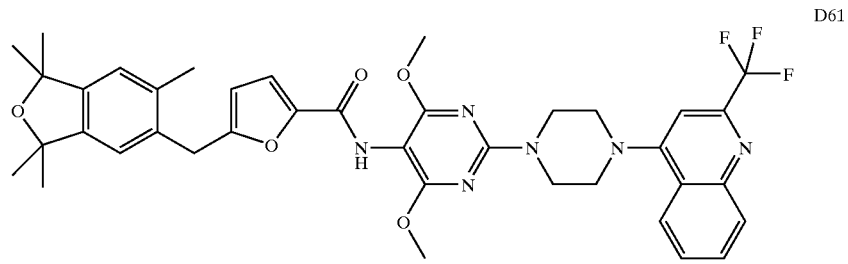

Compound D61 was synthesized according to scheme D where compound 12 was1-[2-(trifluoromethyl)quinol-4-yl] piperazine. NMR and mass spectrometry data consistent with the title product were as follows: $^1$H NMR(MeOD) δ 1.50(m, 12H), 2.36(s, 3H), 3.44(t, 4H, J=4.15 Hz), 3.91(s, 6H), 4.09(s, 2H), 4.18(t, 4H, J=4.91 Hz), 6.03(d, 1H, J=3.40 Hz), 6.98(m, 2H), 7.10(d, 1H, J=3.40 Hz), 7.34(s, 1H), 7.70(m, 1H), 7.85(m, 1H), 8.12(d, 2H, J=8.69 Hz), 8.27(d, 1H, J=8.31 Hz): M/z 731.3(M+1).

Example D62
N-{2-[4-(4-Chlorophenyl)piperazin-1-yl]-4,6-dimethoxypyrimidin-5-yl}-5-[(1,1,3,3,6-pentamethyl-1,3-dihydro-2-benzofuran-5-yl)methyl]-2-furamide.

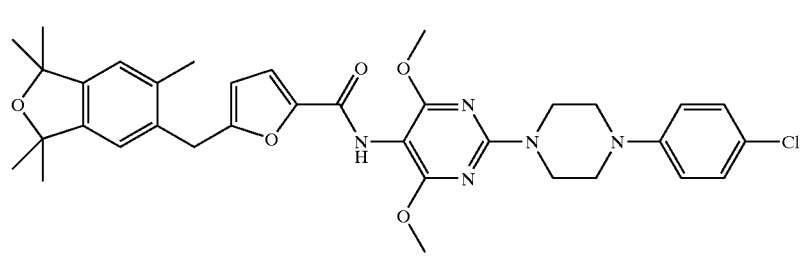

Compound D62 was synthesized according to scheme D where compound 12 was 1-(4-chlorophenyl)piperazine. NMR and mass spectrometry data consistent with the title product were as follows: $^1$H NMR(MeOD) δ 1.49(m, 12H), 2.34(s, 3H), 3.20(t, 4H, J=5.29 Hz), 3.89(s, 6H), 3.99(t, 4H, J=5.29 Hz), 4.10(s, 2H), 6.05(d, 1H, J×3.40 Hz). 6.99(m, 4H), 7.07(d, 1H, J=3.40 Hz), 7.22(d, 2H, J=9.07 Hz): M/z 646.2(M+1).

Example D63
N-(4,6-Dimethoxy-2-{[3-(4-methylpiperazin-1-yl)propyl]amino}pyrimidin-5-yl)-5-[(1,1,3,3,6-pentamethyl-1,3-dihydro-2-benzofuran-5-yl)methyl]-2-furamide.

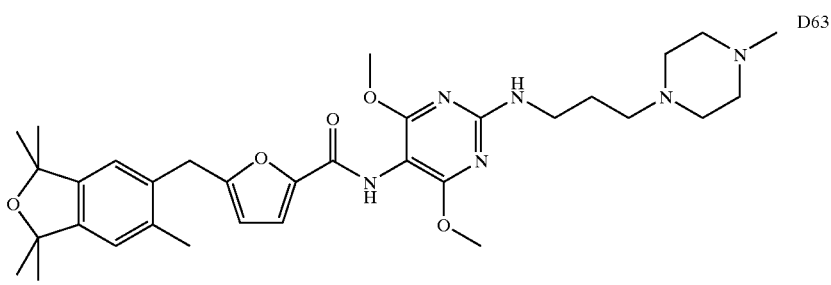

Compound D63 was synthesized according to scheme D where compound 12 was 1-(3-aminopropyl)-4-methylpiperazine. NMR and mass spectrometry data consistent with the title product were as follows: $^1$H NMR (CDCl$_3$) δ 1.47(m, 12H), 1.75(m, 2H), 2.29(m, 6H), 2.49(m, 10H), 3.45(m, 2H), 3.84(s, 6H), 3.99(s, 2H), 6.01(m, 1H), 6.83(s, 1H), 6.90(s, 1H), 7.06(m, 1H): M/z 607.3(M+1).

Example D64

N-(2-{[(1S)-2-Hydroxy-1-(1H-indol-3-ylmethyl)ethyl]amino}-4,6-dimethoxypyrimidin-5-yl)-5-[(1,1,3,3,6-pentamethyl-1,3-dihydro-2-benzofuran-5-yl)methyl]-2-furamide.

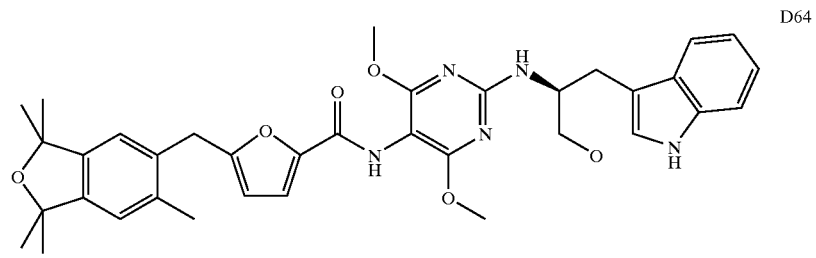

Compound D64 was synthesized according to scheme D where compound 12 was L-tryptophanol. NMR and mass spectrometry data consistent with the title product were as follows: $^1$H NMR(CDCl$_3$) δ 1.49(m, 12H), 2.33(s, 3H), 3.04(d, 2H, J=6.61 Hz), 3.65(m, 1H), 3.79(m, 7H), 4.01(s, 2H), 4.38(m, 1H), 6.03(m, 1H), 6.84(s, 1H), 6.91(s, 1H), 6.97(m, 1H), 7.12(m, 3H), 7.34(d, 1H, J=7.93 Hz), 7.64(d, 1H, J=7.74 Hz): M/z 640.1(M+1).

Example D65

N-{4,6-Dimethoxy-2-[(2-pyridin-2-ylethyl)amino]pyrimidin-5-yl}-5-[(1,1,3,3,6-pentamethyl-1,3-dihydro-2-benzofuran-5-yl)methyl]-2-furamide.

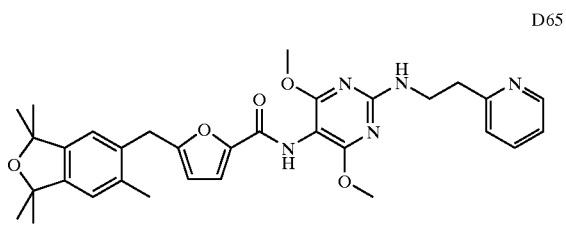

Compound D65 was synthesized according to scheme D where compound 12 was 2-(2-aminoethyl)pyridine. $^1$H NMR (CDCl$_3$) δ 1.46(m, 12H), 2.33(s, 3H), 3.08(m, 2H), 3.78(m, 2H), 3.87(s, 6H), 3.99(s, 2H), 5.34(s, 1H), 6.03(m, 1H), 6.84(s, 1H), 6.91(s, 1H), 7.03(s, 1H), 7.09(m, 1H), 7.16(m, 2H), 7.60(m, 1H), 8.55(m, 1H). APCI-MS m/z 572.2 (M+1). HRMS: 572.2866 (C32 H37 N5 O5)

Example D66

N-{4,6-Dimethoxy-2-[(2-pyridin-4-ylethyl)amino]pyrimidin-5-yl}-5-[(1,1,3,3,6-pentamethyl-1,3-dihydro-2-benzofuran-5-yl)methyl]-2-furamide.

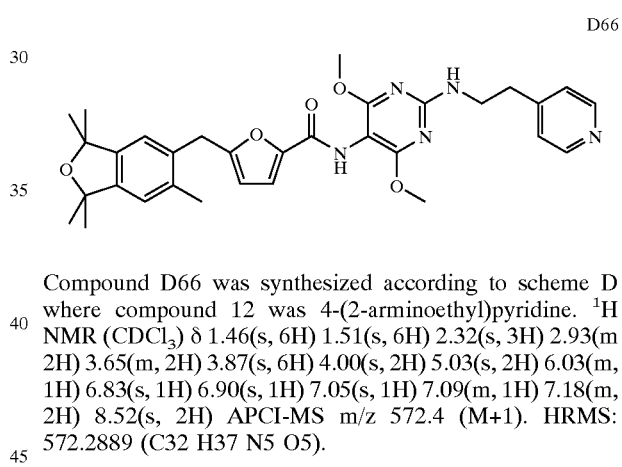

Compound D66 was synthesized according to scheme D where compound 12 was 4-(2-arminoethyl)pyridine. $^1$H NMR (CDCl$_3$) δ 1.46(s, 6H) 1.51(s, 6H) 2.32(s, 3H) 2.93(m 2H) 3.65(m, 2H) 3.87(s, 6H) 4.00(s, 2H) 5.03(s, 2H) 6.03(m, 1H) 6.83(s, 1H) 6.90(s, 1H) 7.05(s, 1H) 7.09(m, 1H) 7.18(m, 2H) 8.52(s, 2H) APCI-MS m/z 572.4 (M+1). HRMS: 572.2889 (C32 H37 N5 O5).

Example D67

N-{4,6-Dimethoxy-2-[(2-pyridin-3-ylethyl)amino]pyrimidin-5-yl}-5-[(1,1,3,3,6-pentamethyl-1,3-dihydro-2-benzofuran-5-yl)methyl]-2-furamide.

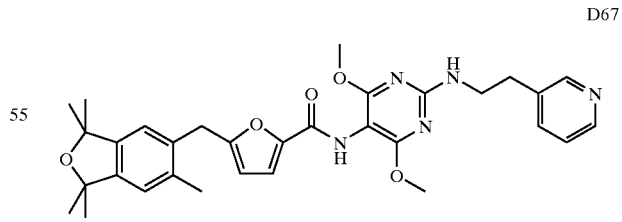

Compound D67 was synthesized according to scheme D where compound 12 was 3-(2-aminoethyl)pyridine. $^1$H NMR (CDCl$_3$) δ 1.49(m, 12H) 2.32(s, 3H) 2.92(m, 2H) 3.63(m, 2H) 3.86(s, 6H) 4.01(s, 2H) 5.07(s, 1H) 6.04(m, 1H) 6.86(s, 1H) 6.92(s, 1H) 7.08(m, 2H) 7.26(m, 2H) 7.56(s, 1H) 8.50(m, 2H),) APCI-MS m/z 572.2 (M+1). HRMS: 572.2869 (C32 H37 N5 O5).

Example D68

N-(4,6-Dimethoxy-2-{[2-(1-methylpyrrolidin-2-yl)ethyl]amino}pyrimidin-5-yl)-5-[(1,1,3,3,6-pentamethyl-1,3-dihydro-2-benzofuran-5-yl)methyl]-2-furamide.

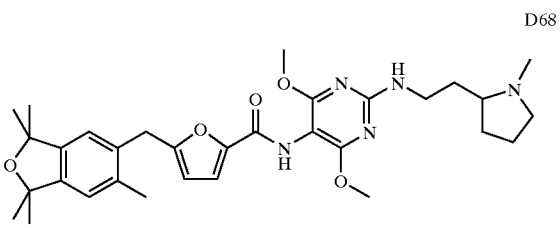

D68

Compound D68 was synthesized according to scheme D where compound 12 was 2-(2-aminoethyl)-1-methylpyrrolidine. ¹H NMR (CDCl₃) δ 1.44(m, 12H), 1.64 (s, 4H), 0.97(s, 2H), 2.16(s, 2H), 2.31(m, 6H), 3.09(s, 1H), 3.43(s, 2H), 3.85(s, 6H), 3.99(s, 2H), 5.20(s, 1H), 6.03(s, 1H), 6.83(s, 1H), 6.91(s, 1H), 7.01(s, 1H, 7.08(s, 1H). APCI-MS m/z 578.3 (M+1).

Example D69

N-(4,6-Dimethoxy-2-{[3-(2-methylpiperidin-1-yl)propyl]amino}pyrimidin-5-yl)-5-[(1,1,3,3,6-pentamethyl-1,3-dihydro-2-benzofuran-5-yl)methyl]-2-furamide.

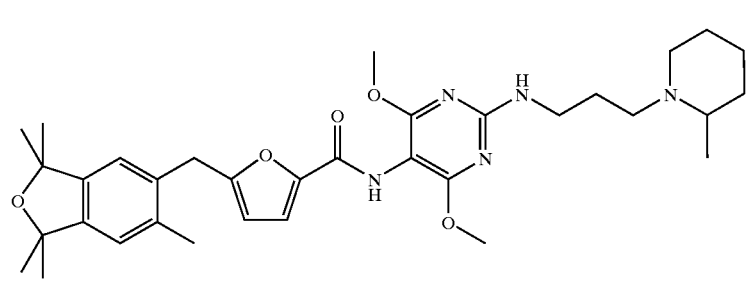

D69

Compound D69 was synthesized according to scheme D where compound 12 was 1-(3-aminopropyl)-2-popecoline. ¹H NMR (CDCl₃) δ 1.08(m, 33H) 1.30(s, 2H) 1.49(s, 6H) 1.51 (s, 6H) 1.67(m, 4H) 1.84(m, 2H) 2.32(s, 3H) 2.52(m, 2H) 2.71(m, 2H) 2.94(m, 2H) 3.42(s, 2H) 3.83(s, 6H) 3.99(s, 2H) 5.79(s, 1H) 6.00(m, 1H) 6.81(s, 1H) 7.05(m, 2H). APCI-MS m/z 606.3 (M+1).

Example D70

N-(2-{[3-(Dimethylamino)-2,2-dimethylpropyl]amino}-4,6-dimethoxypyrimidin-5-yl)-5-[(1,1,3,3,6-pentamethyl-1,3-dihydro-2-benzofuran-5-yl)methyl]-2-furamide.

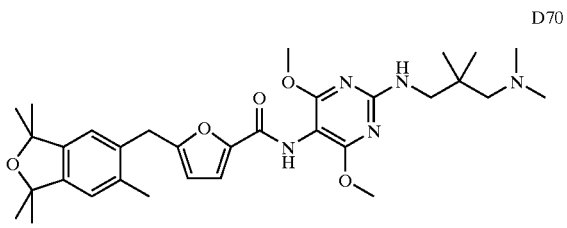

D70

Compound D70 was synthesized according to scheme D where compound 12 was N,N,2,2-tetramethyl-1,3-propanediamine. ¹H NMR (CDCl₃) δ 0.94(s, 6H), 1.49(m, 12H), 2.23(s, 2H), 2.33(s, 9H), 3.30(s, 2H), 3.87(s, 3H), 4.01(s, 2H), 6.01(s 1H), 6.14(s, 1H), 6.84(s, 1H), 6.91(s, 1H), 7.03(s, 1H), 7.10(s, 1H). APCI-MS m/z 580.3 (M+1).

Example D71

N-{4,6-Dimethoxy-2-[(3-methoxypropyl)amino]pyrimidin-5-yl}-5-[(1,1,3,3,6-pentamethyl-1,3-dihydro-2-benzofuran-5-yl)methyl]-2-furamide.

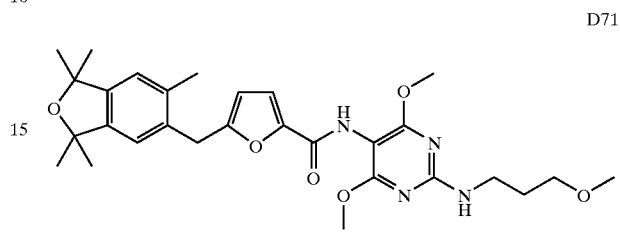

D71

Compound D71 was synthesized according to scheme D where compound 12 was 3-methoxypropylamine. The product was recovered at 21.8 mg (20%) from 97.2 mg corresponding chloropyrimidinylamide. Its NMR and mass spectrometry were as follows: ¹HNMR (DMSO-d₆) δ 1.38(d, 12H, J=3.2 Hz), 1.76(m, 2H), 2.29(s, 3H), 3.22(s, 3H), 3.26–3.39(m, 4H), 3.75(s, 6H), 4.00(s, 2H), 6.18(d, 1H, J=3.4 Hz), 7.01(s, 1H), 7.06(s, 1H), 7.09(d, 1H, J=3.4 Hz), 7.14(t, 1H, J=5.7 Hz), 8.88(s, 1H). M/Z 539(M+1).

Example D72

N-(4,6-Dimethoxy-2-{methyl[2-(methylsulfonyl)ethyl]amino}-pyrimidin-5-yl)-5-[(1,1,3,3,6-pentamethyl-1,3-dihydro-2-benzofuran-5-yl)methyl]-2-furamide.

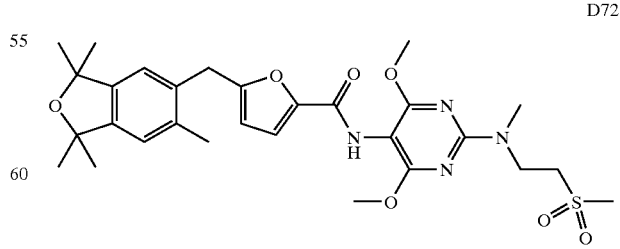

D72

Compound D72 was synthesized according to scheme D where the last step was performed as follows:

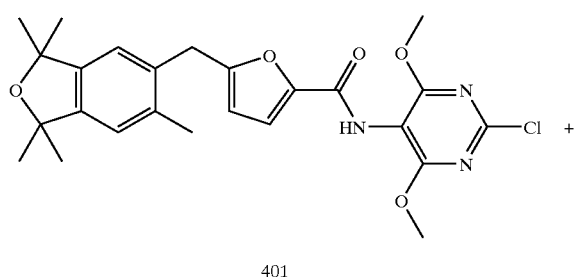

401

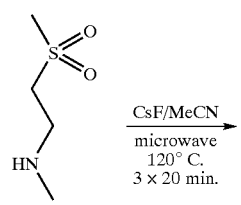

402

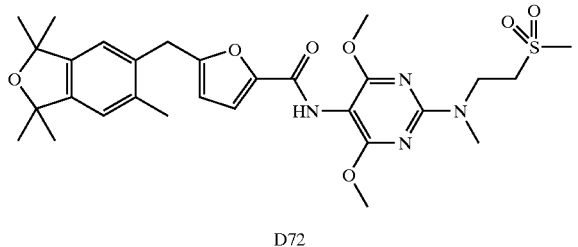

D72

A mixture of compounds 401 (100 mg, 0.21 mmol) and 402 (29 mg, 0.21 mmol) and CsF (32 mg, 0.21 mmol) in 4 mL of anhydrous MeCN was heated up to 120° C. for 20 mm three times by using Smith Synthesizer. The resulting product was diluted with water, extracted with EtOAc and dried over MgSO$_4$. After removing solvent, the residue was purified by Dionex (25–70% MeCN/H$_2$O). Forty mg of compound D72 was obtained (yield 30%): $^1$H NMR (δ, DMSO-d$_6$): 1.32(d, 12H), 2.23(s, 3H), 2.97(s, 3H), 3.08(s, 3H), 3.41(dd, 2H, J=7.54, 6.78 Hz), 3.74(s, 6H), 3.92(m, 4H), 6.13(d, 1H, J=3.39 Hz), 6.95(s, 1H), 7.00(s, 1H), 7.05(d, 1H, J=3.39 Hz), 8.91(s, 1H). MS (APCI, M+H): 587.

Example D73

N-{2-[(2,6-difluorobenzyl)amino]-4,6-dimethoxypyrimidin-5-yl}-5-[(1,1,3,3,6-pentamethyl-1,3-dihydro-2-benzofuran-5-yl)methyl]-2-furamide.

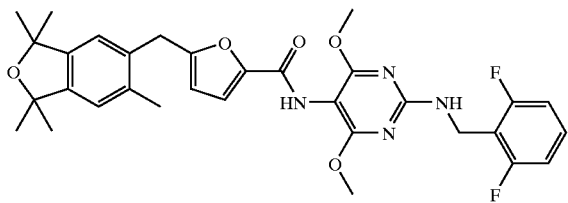

D73

Compound D73 was synthesized according to Scheme D where compound 12 was

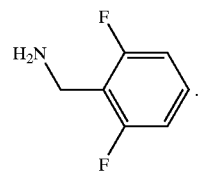

The NMR and mass spectrometry data for Compound D73 were as follows: $^1$H NMR (300 MHz, CHLOROFORM-D) δ ppm 1.48 (d, J=6.97 Hz, 12H) 2.32 (s, 3H) 3.87 (s, 6H) 4.68 (d, J=6.22 Hz, 2H) 5.40 (s, 1H) 6.01 (d, J=3.20 Hz, 1H) 6.87 (m, 4H) 7.06 (m, 2H) 7.21 (s, 1H); APCI-MS m/z 593 (M+H)$^+$.

Example D74

N-{4,6-dimethoxy-2-[(2-methylethyl)amino]-pyrimidin-5-yl}-5-[(1,1,3,3,6-pentamethyl-1,3-dihydro-2-benzofuran-5-yl)methyl]-2-furamide.

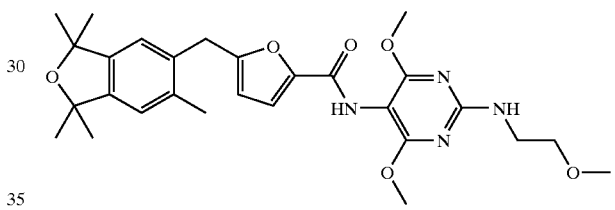

D74

Compound D74 was synthesized according to Scheme D where Compound 12 was

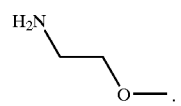

The NMR and mass spectrometry data for Compound D74 were as follows: $^1$H NMR (300 MHz, CHLOROFORM-D) δ ppm 1.48 (d, J=6.78 Hz, 12H) 2.32 (s, 3H) 3.38 (s, 3H) 3.57 (m, 4H) 3.86 (s, 6H) 4.00 (s, 2H) 5.26 (s, 1H) 6.02 (d, J=3.20 Hz, 1H) 6.84 (s, 1H) 6.90 (s, 1H) 7.07 (m, 2H); APCI-MS m/z 525 (M+H)$^+$.

The following compound was prepared according to Scheme E set forth below:

Compound 22

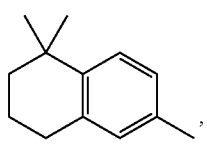

was synthesized according to the procedure in the *Indian J. Chem. Sect.* B(1984), 23B(1), 87–8.

Example E1

5-(3,8,8-Trimethyl-5,6,7,8-tetrahydro-naphthalen-2-ylmethyl)-furan-2-carboxylic acid [4,6-dimethoxy-2-(2-methoxy-ethoxy)-pyrimidin-5-yl]-amide.

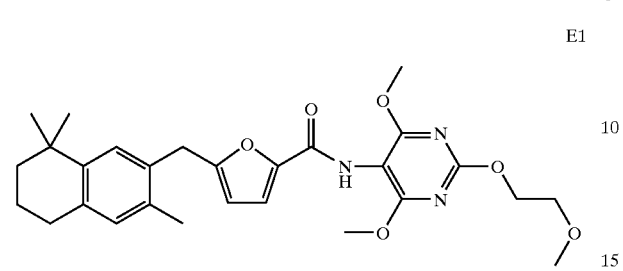

Compound E1 was synthesized in a manner analogous to compound A4 except compound 5 in scheme A was replaced with compound 22. NMR and mass spectrometry data consistent with the title product were as follows: $^1$H-NMR (CDCl$_3$) δ 1.24(s, 2H), 1.58(m, 1H), 1.85(m, 1H), 2.23(s, 1H), 2.70(t, 1H, J=6.42 Hz), 3.42(s, 1H), 3.75(t, 1H, J=4.91 Hz), 3.95(s, 2H), 3.97(s, 1H), 4.49(t, 1H, J=4.91 Hz), 6.01(d, 1H, J=3.40 Hz), 6.87(s, 1H), 7.08(m, 2H). M/z 510.2 (M+1)

The following examples were prepared according to Scheme F set forth below:

Scheme F

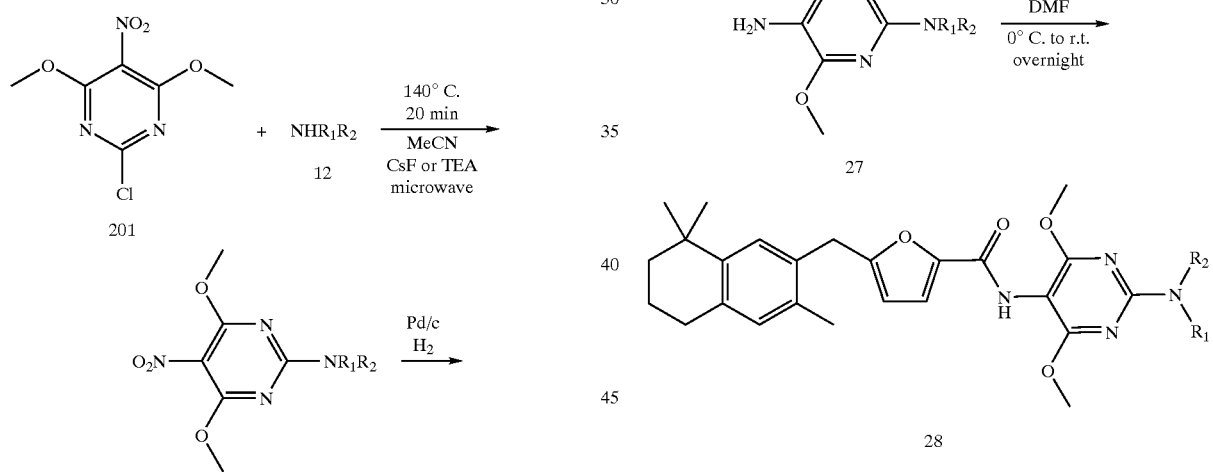

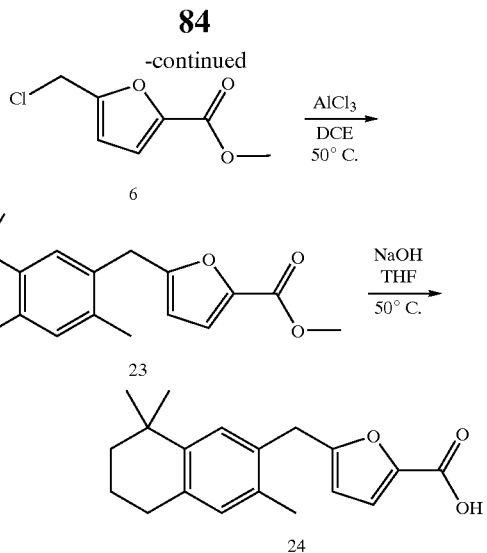

Compounds 22 and 6 were added to dichloroethane, 0.5M. AlCl$_3$ was added slowly over 30 minutes. Once the addition was complete, the reaction mixture was heated to 50° C. overnight. The reaction was then cooled, quenched with H$_2$O, concentrated, and purified by column chromatography using 5% ethyl acetate/hexane, to give compound 23. Compound 23 was dissolved in THF, 1 M, and 10 eq of NaOH in minimal H$_2$O was added. The reaction mixture was refluxed overnight, cooled and quenched with 1 M HCl to afford an acetic pH. The reaction was then extracted with dichloromethane and concentrated to give compound 24. Compound 24 was taken up in dichloromethane, 1 M, and SOCl$_2$ was slowly added. The reaction was allowed to stir overnight at room temperature. The mixture was then refluxed 4 hours, cooled back to room temperature, concentrated and purified by column chromatography using hexanes to give pure compound 24.

Example F1

5-(3,8,8-Trimethyl-5,6,7,8-tetrahydro-naphthalen-2-ylmethyl)-furan-2-carboxylic acid [4,6-dimethoxy-2-(3-morpholin-4-yl-propylamino)-pyrimidin-5-yl]-amide.

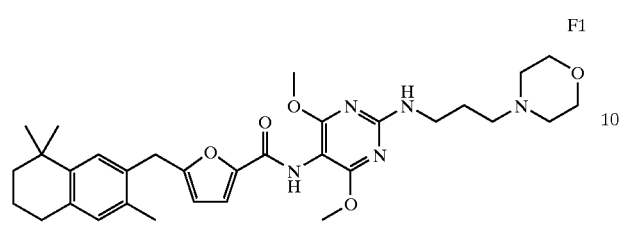

F1

To a solution of 2-chloro-4,6-dimethoxy-5-nitropyrimidine, compound 201 (17.5 mg, 0.08 mmol), and 3-morpholin-4-ylpropan-1-amine, compound 12 (12.1 mg, 0.08 mmol), in N,N-dimethylacetamide (0.3M), was added cesium fluoride (50 mg, 0.40 mmol) and heated at 80° C. The resulting product, 4,6-dimethoxy-N-(3-morpholin-4-ylpropyl)-5-nitropyrimidin-2-amine, was hydrogenated using palladium on carbon to give compound 27, followed by HATU coupling with compound 24, 5-[(3,8,8-trimethyl-5,6,7,8-tetrahydronaphthalen-2-yl)methyl]-2-furoic acid, to produce the title product. NMR and mass spectrometry data consistent with the title product were as follows: $^1$H NMR (300 MHz, CD$_3$OD) δ 7.15 (s, 1H), 7.08 (d, J=-3.40 Hz, 1H), 6.86 (s, 1H), 6.01(d, J=3.40 Hz, 1H), 4.03 (s, 2H), 3.89 (s, 6H), 3.82 (m, 4H), 3.49 (m, 2H), 2.92 (m, 6H), 2.72(m, 2H), 2.22 (s, 3H), 1.98 (m, 2H), 1.80 (m, 4H), 1.67 (m, 4H), 1.25 (s, 6H). MS (FAB) M/z 578 (M+1).

Example F2

5-(3,8,8-Trimethyl-5,6,7,8-tetrahydro-naphthalen-2-ylmethyl)-furan-2-carboxylic acid [2-(2-cyano-ethylamino)-4,6-dimethoxy-pyrimidin-5-yl]-amide.

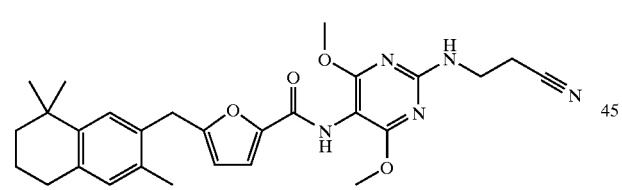

F2

To a solution of 2-chloro-4,6-dimethoxy-5-nitropyrimidine, compound 201 (17.5 mg, 0.08 mmol) and 3-aminopropanenitrile, compound 12 (5.9 mg, 0.08 mmol), in N,N-dimethylacetamide (0.3M), was added cesium fluoride (50 mg, 0.40 mmol) and heated at 80° C. until the reaction was complete. The resulting product, 3-[(4,6-dimethoxy-5-nitropyrimidin-2-yl)amino]propanenitrile, was hydrogenated using palladium on carbon to give compound 27, followed by HATU coupling with compound 24, 5-[(3, 8,8-trimethyl-5,6,7,8-tetrahydronaphthalen-2-yl)methyl]-2-furoic acid, to produce the title product. NMR and mass spectrometry data consistent with the title product were as follows: $^1$H NMR (300 MHz, CD$_3$OD) δ 7.15 (s, 1H), 7.09(d, J=3.40 Hz, 1H), 6.86 (s, 1H), 6.01 (d, J=3.40 Hz, 1H), 4.03 (s, 2H), 3.91 (s, 6H), 3.67 (m, 2H), 2.81 (m, 2H), 2.71 (m, 2H), 2.23 (s, 3H), 1.82 (m, 2H), 1.66 (m, 2H), 1.25 (s, 6H). MS (FAB) M/z 5.04 (M+1).

The following example was prepared according to Scheme G set forth below:

Scheme G

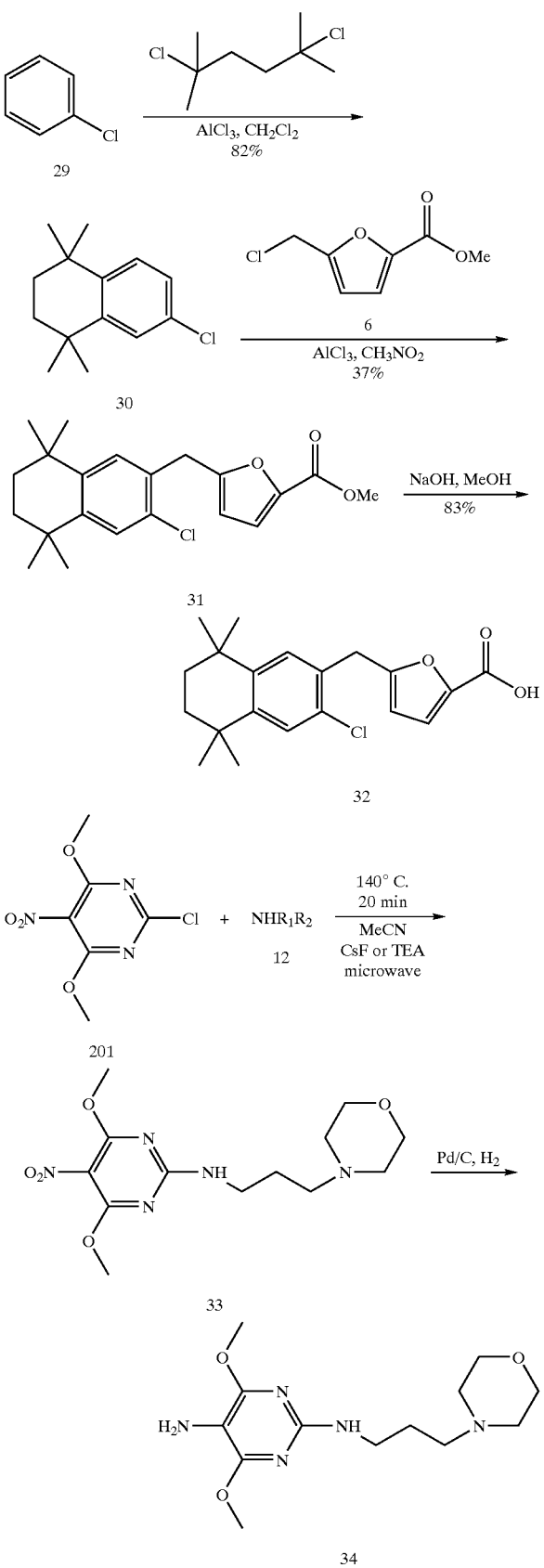

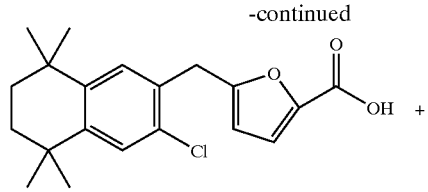

32

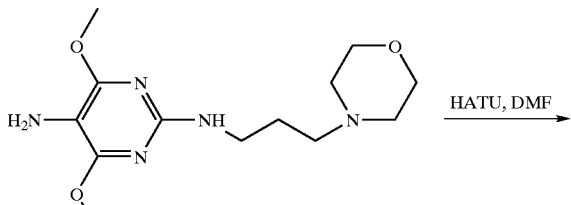

34

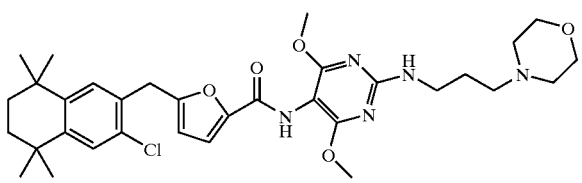

Compound G1

Example G1

5-(3-Chloro-5,5,8,8-tetramethyl-5,6,7,8-tetrahydro-naphthalen-2-ylmethyl)-furan-2-carboxylic acid[4,6-dimethoxy-2-(3-morpholin-4-yl-propylamino)-pyrimidin-5-yl]-amide.

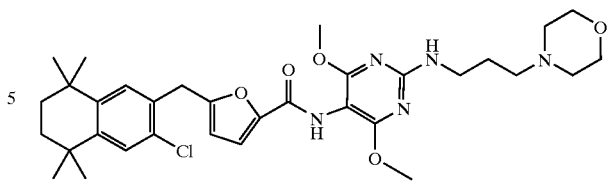

To a solution of mixture of chlorobenzene, compound 29 (5 g, 44.6 mmol) and: 2,5-dichloro-2,5-dimethylhexane (8.2 g, 44.6 mmol.) in CH$_2$Cl$_2$ (150 mL) was added AlCl$_3$ (2 g, 13.4 mmol.). The solution was stirred at room temperature for one hour. The reaction mixture was slowly poured into ice water, extracted with EtOAc, washed with H$_2$O, dried (MgSO$_4$) and concentrated to give 6-chloro-1,1,4,4-tetramethyl-1,2,3,4-tetrahydronaphathlene, compound 30 (8.2 g), as an oil. Compounds 30 and 6 were added to dichloroethane, 0.5M. AlCl$_3$ was added slowly over 30 minutes. Once the addition was complete, the reaction mixture was heated to 50° C. overnight. The reaction was then cooled, quenched with H$_2$O, concentrated, and purified by column chromatography using 5% ethyl acetate/hexane, to give compound 31. Compound 31 was dissolved in THF, 1 M, and 10 eq of NaOH in minimal H$_2$O was added. The reaction mixture was refluxed overnight, cooled and quenched with 1 M HCl to afford an acetic pH. The reaction was then extracted with dichloromethane and concentrated to give compound 32. To a solution of 2-chloro-4,6-dimethoxy-5-nitropyrimidine, compound 201 (17.5 mg, 0.08 mmol) and 3-morpholin-4-ylpropan-1-amine, compound 12 (12.1 mg, 0.08 mmol), in N,N-dimethylacetamide (0.3M), was added cesium fluoride (50 mg, 0.40 mmol) and heated at 80° C. The resulting product, compound 33, was hydrogenated using palladium on carbon to give compound 34, followed by HATU coupling with compound 32, to give compound G1. NMR and mass spectrometry data consistent with the title product were as follows: $^1$H NMR (300 MHz, DMSO-d$_6$) delta 1.18 (s, 6H), 1.20 (s, 6H), 1.59 (s, 4H), 1.93 (m, 2H), 3.06–3.14 (m, 4H), 3.32 (m, 4H), 3.59 (t, 2H), 3.93 (s, 6H), 3.97 (m, 2H), 4.11 (s, 2H), 6.20 (d, 1H), 7.08 (d, 1H), 7.16(t, 1H), 7.42(s, 2H), 8.90(s, 1H), 6.95 (s, 1H). APCI-MS M/z 626.3 (M+1).

The following compounds were prepared according to scheme H set forth below:

Scheme H

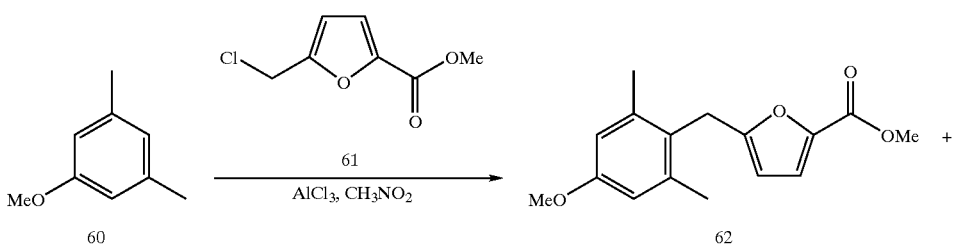

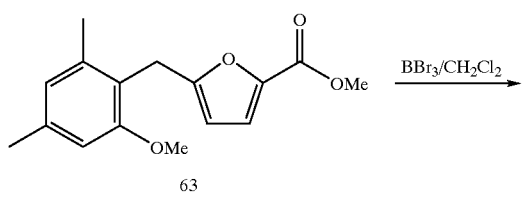

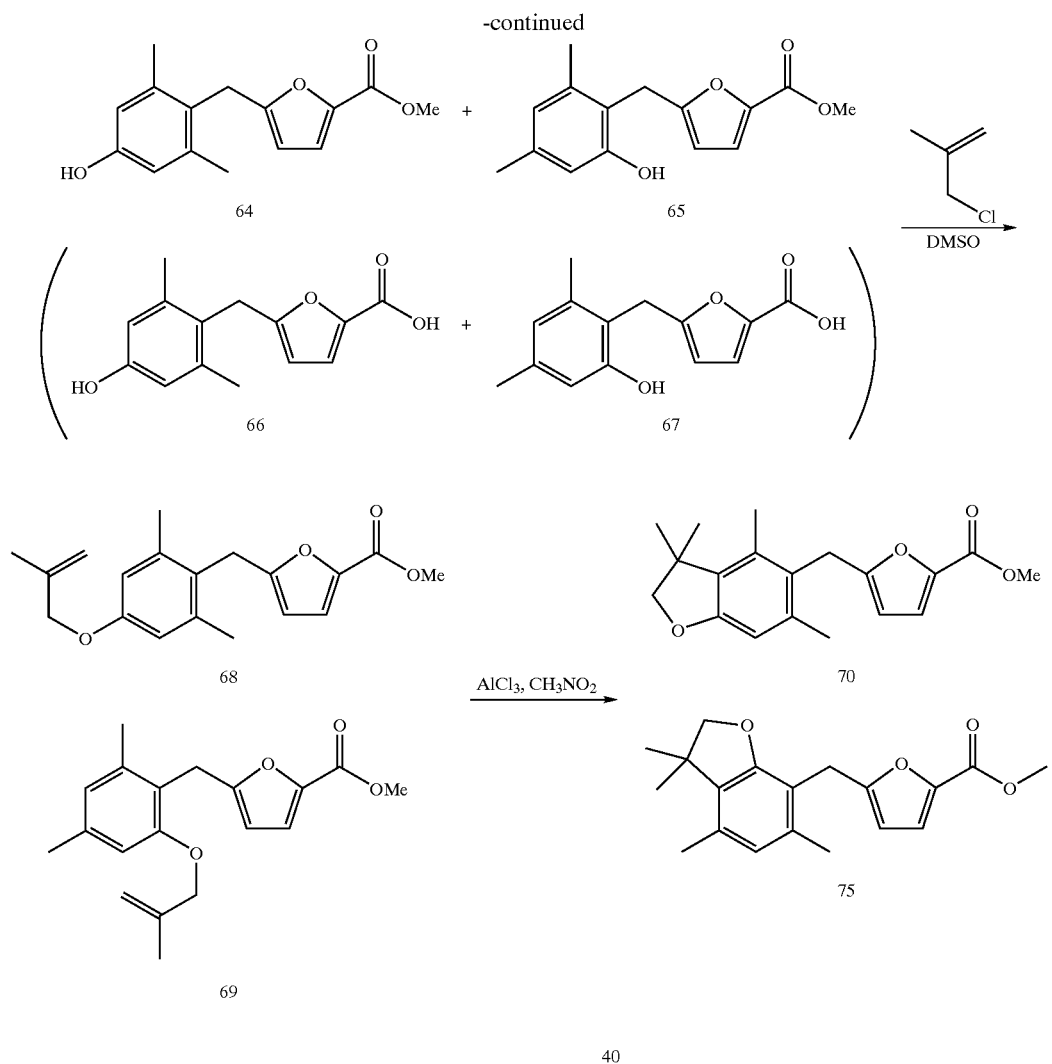

To a solution of compounds 60 (10 g) and 61 (12.8 g) in 150 mL of $CH_3NO_2$ was added a solution of $AlCl_3$ (14.9 g) in $CH_3NO_2$ (50 mL) at room temperature. The solution was then heated to 60° C. overnight. The mixture was poured into ice water slowly. Column chromatography (hexane/ethyl acetate) gave a mixture of compounds 62 and 63 (16.3 g). The mixture was dissolved in $CH_2Cl_2$ (50 mL) and a solution of $BBr_3$ (1 M, 60 mL) was added at −78° C. The solution was stirred overnight. The reaction was quenched by addition of MeOH at 0° C. Column chromatography (hexane/ethyl acetate: 8/1 to 4/1) gave compound 65 (20.3 g), a mixture of compounds 64 and 65 (5.2 g), and a mixture of compounds 66 and 67 (4.2 g). The mixture of compounds 64 and 65 (5 g) was dissolved in DMSO (100 mL). To this solution was added potassium tert-butoxide (2.5 g) followed by addition of 3-chloro-2-methylpropene (2 g). After being stirred at rt. for 4 hours the reaction mixture was extracted with EtOAc, washed with water, dried ($MgSO_4$) and concentrated to give a mixture of compounds 68 and 69. The mixture was dissolved in $CH_2Cl_2$ (200 ml) and $AlCl_3$ (3 g) was added. The solution was stirred at room temperature (rt.) for 20 minutes, quenched with ice water, and extracted with EtOAc. Column chromatography (hexane/ethyl acetate: 9/1) gave a mixture of compounds 70 and 75 (2.3 g).

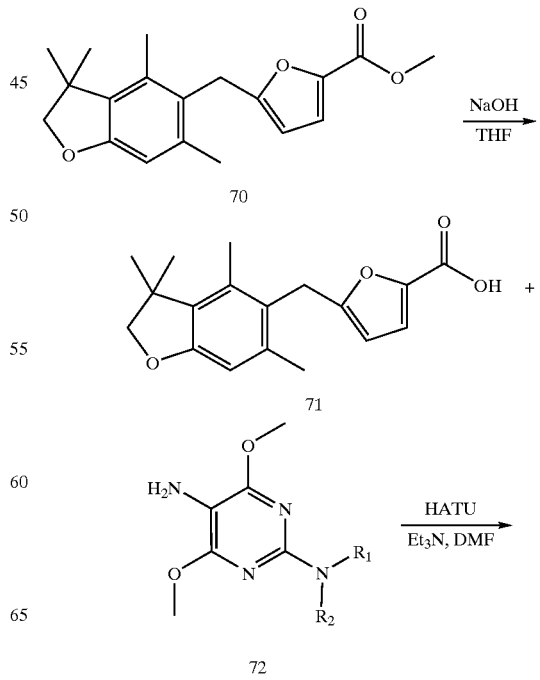

-continued

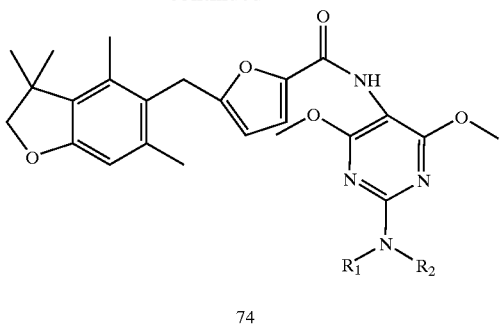

74

Compound 70 was dissolved in THF, 1 M, and 10 eq of NaOH in minimal H₂O was added. The reaction mixture was refluxed overnight, cooled and quenched with 1 M HCl to afford an acetic pH. The reaction was then extracted with dichloromethane and concentrated to give compound 71. To a solution of compound 71 in DMF was added Et₃N (1.0 eq.) and HATU (1.1 eq.). After being stirred at rt. for 15 minutes, to the solution was added a solution of compound 72 in DMF, followed by stirring for 1 hour. The resulting crude mixture was purified by HPLC (CH₃CN/H₂O 30% to 90% in 30 minutes) to give compound 74.

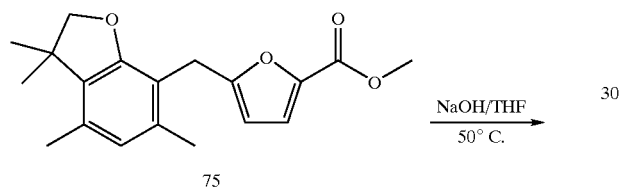

75

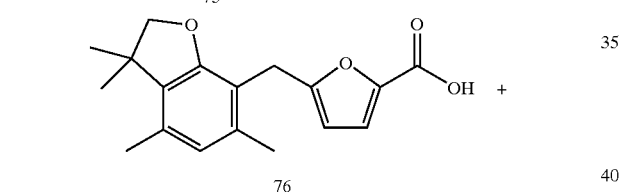

76

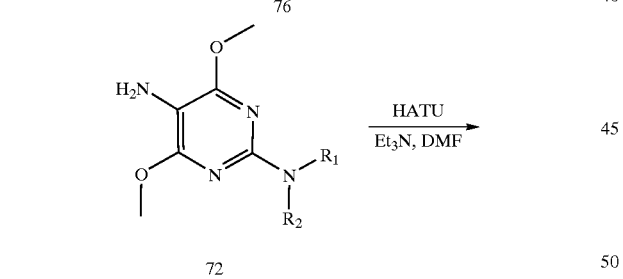

72

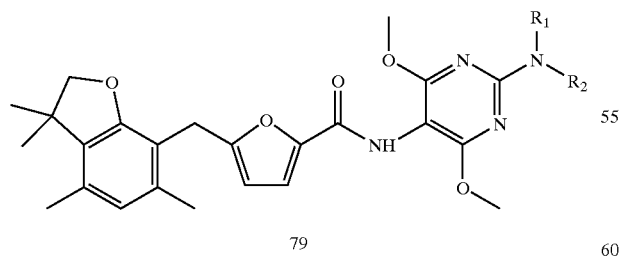

79

Compound 75 was dissolved in THF, 1 M, and 10 eq of NaOH in minimal H₂O was added. The reaction mixture was refluxed overnight, cooled and quenched with 1 M HCl to afford an acetic pH. The reaction was then extracted with dichloromethane and concentrated to give compound 76. To a solution of compound 76 in DMF was added Et₃N (1.0 eq.)

and HATU (1.1 eq.). After being stirred at rt. for 15 minutes, to the solution was added a solution of compound 72 in DMF, followed by stirring for 1 hour. The crude mixture was purified by HPLC (CH₃CN/H₂O 30% to 90% in 30 minutes) to give the compound of formula 79.

The compound of the formula 72 was synthesized according to the following scheme:

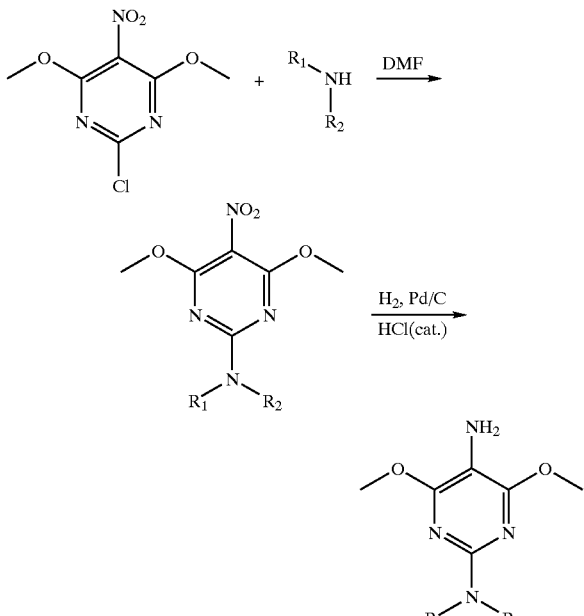

Example H1

N-{4,6-Dimethoxy-2-[(3-morpholin-4-ylpropyl)amino]-pyrimidin-5-yl}-5-[(3,3,4,6-tetramethyl-2,3-dihydro-1-benzofuran-5-yl)methyl]-2-furamide.

H1

Compound H1 was synthesized according to scheme H where compound 70 was the ester and compound 72 was synthesized according to the following procedure:

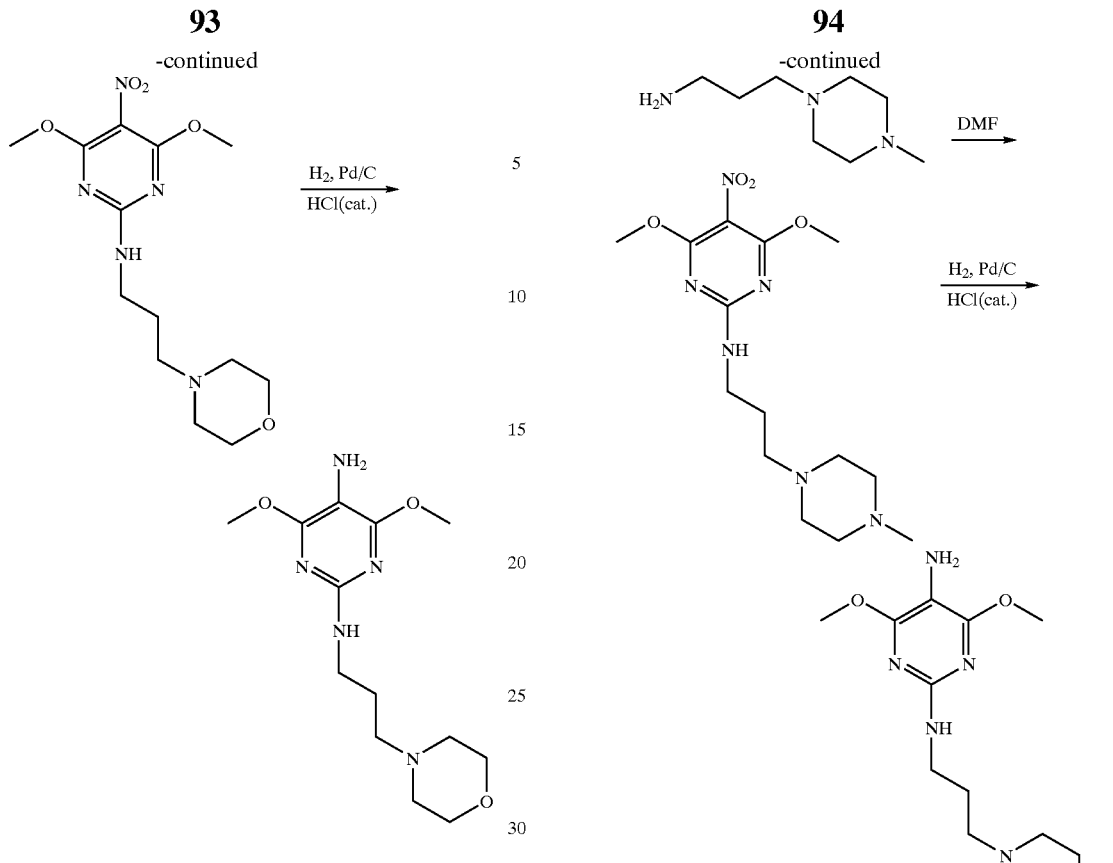

NMR and mass spectrometry data consistent with the title product were as follows:

$^1$HNMR (DMSO-$d_6$) 1.37(s, 6H), 1.68(m, 2H), 2.10(s, 3H), 2.21(s, 3H), 2.34(s, 6H), 2.89(s, 2H), 3.55(m, 2H), 3.73(s, 6H), 3.90(s, 2H), 5.94(s, 1H), 6.39(s, 1H), 7.05(m, 1H), 7.19(s, 1H), 8.84(s, 1H). M/z 580.3 (M+1).

Example H2
N-(4,6-Dimethoxy-2-{[3-(4-methylpiperazin-1-yl)propyl]amino}pyrimidin-5-yl)-5-[(3,3,4,6-tetramethyl-2,3-dihydro-1-benzofuran-5-yl)methyl]-2-furamide, NMR and mass spectrometry data consistent with the title product were as follows:

$^1$HNMR (DMSO-$d_6$) 1.38(s, 6H), 1.67(s, 2H), 2.11(m, 6H), 2.21(s, 3H), 2.33(m, 1H), 2.89(s, 2H), 3.26(s, 2H), 3.76(s, 6H), 3.90(s, 2H), 5.96(m, 1H), 6.39(s, 1H), 7.04(m, 1H), 7.19(s, 1H), 8.85(s, 1H). M/z 593.3 (M+1).

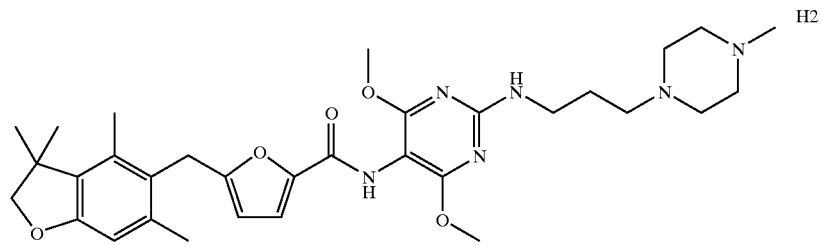

Compound H2 was synthesized according to scheme H where compound 70 was the ester and compound 72 was synthesized according to the following procedure:

Example H3
N-(2-{[3-(Dimethylamino)propyl]amino}-4,6-dimethoxypyrimidin-5-yl)-5-[(3,3,4,6-tetramethyl-2,3-dihydro-1-benzofuran-5-yl)methyl]-2-furamide.

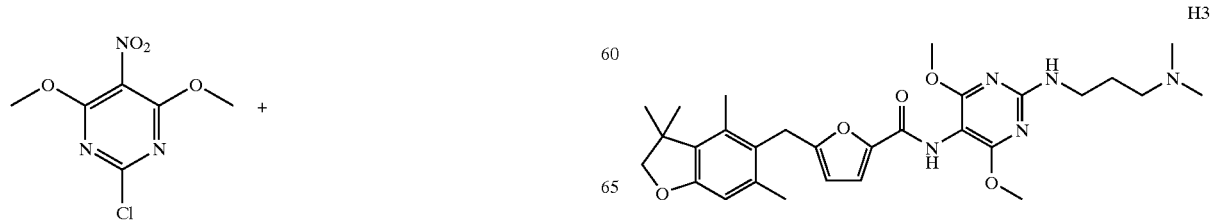

Compound H3 was synthesized according to scheme H where compound 70 was the ester and compound 12 was synthesized according to the following procedure:

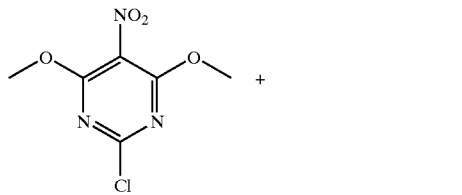

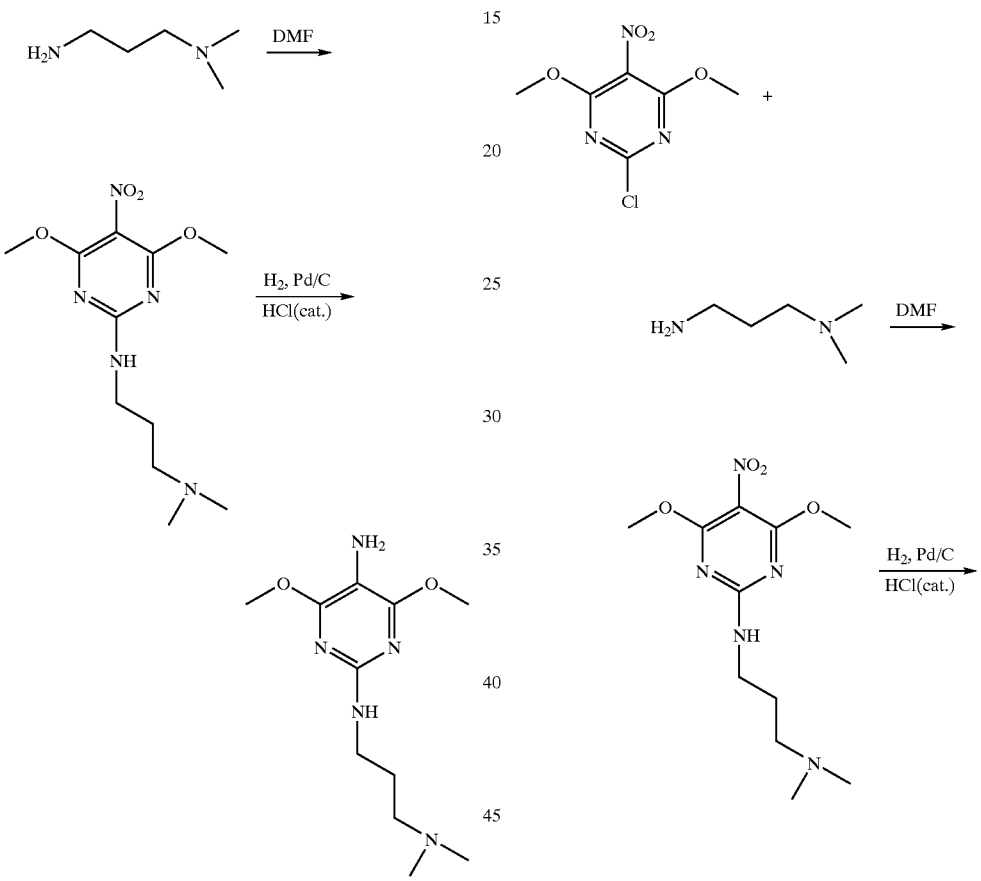

NMR and mass spectrometry data consistent with the title product were as follows:

$^1$HNMR (DMSO-$d_6$) 1.32(s, 6H), 1.72(s, 2H), 2.13(s, 3H), 2.21(s, 3H), 2.30(s, 6H), 2.88(s, 2H), 3.26(s, 4H), 3.76(s, 6H), 3.93(s, 2H), 5.94(m, 1H), 6.40(s, 1H, 7.05(m, 1H), 7.19(s, 1H), 8.86(s, 1H). M/z 538.3 (M+1).

Example H4

N-(2-{[3-(Dimethylamino)propyl]amino}-4,6-dimethoxypyrimidin-5-yl)-5-[(3,3,4,6-tetramethyl-2,3-dihydro-1-benzofuran-7-yl)methyl]-2-furamide.

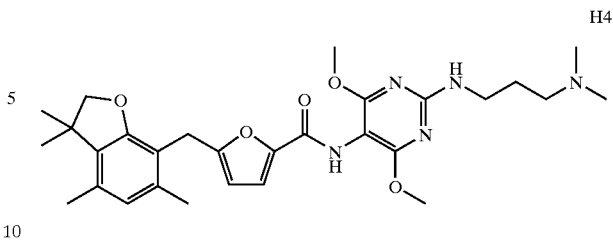

Compound H4 was synthesized according to scheme H where compound 75 was the ester and compound 12 was synthesized according to the following procedure:

NMR and mass spectrometry data consistent with the title product were as follows:
$^1$HNMR (DMSO-$d_6$) 1.35(s, 6H), 1.87(s, 2H), 2.10(s, 3H), 2.18(s, 3H), 2.76(s, 6H), 2.88(s, 2H), 3.08(s, 2H), 3.74(s, 6H), 3.84(s, 2H), 5.86(s, 1H), 6.47(s, 1H), 7.04(s, 1H), 7.26(s, 1H), 8.84(s, 1H). M/z 538.3 (M+1).

Example H5

N-(4,6-Dimethoxy-2-{[3-(4-methylpiperazin-1-yl)propylamino}pyrimidin-5-yl)-5-[(3,3,4,6-tetramethyl-2,3-dihydro-1-benzofuran-7-yl)methyl]-2-furamide.

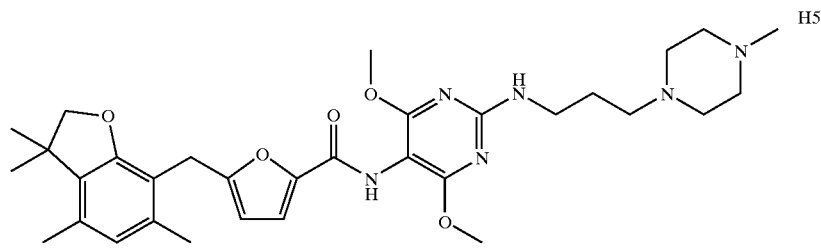

Compound H5 was synthesized according to scheme H where compound 75 was the ester and compound 72 was synthesized according to the following procedure:

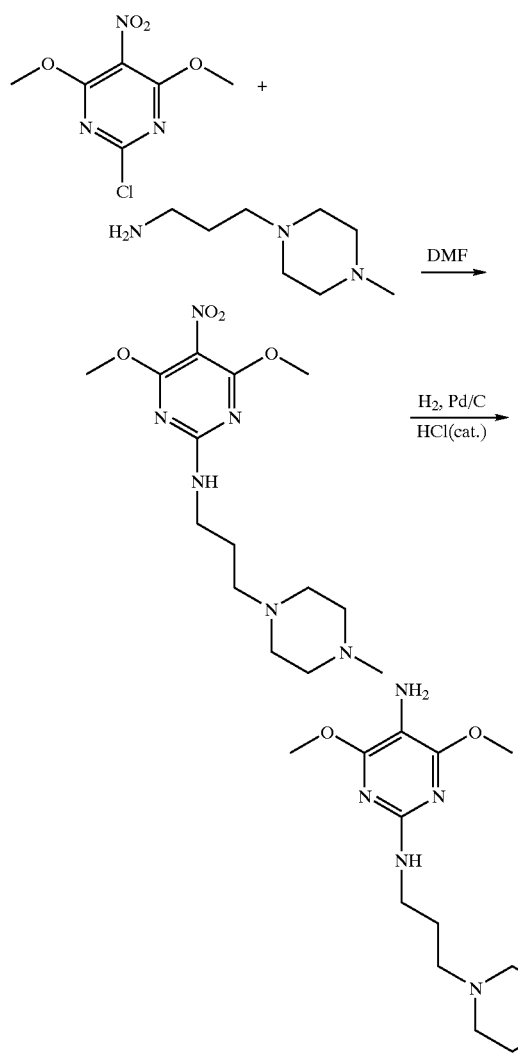

NMR and mass spectrometry data consistent with the title product were as follows:

$^1$HNMR (DMSO-$d_6$) 1.36(s, 6H), 1.65(s, 2H), 1.88(s, 1H), 2.08(m, 6H), 2.18(s, 3H), 2.30(s, 8H), 2.88(s, 2H), 3.33(s, 2H), 3.74(s, 6H), 3.85(s, 2H), 5.88(s, 1H), 6.46(s, 1H), 7.03(s, 1H), 7.22(s, 1H), 8.80(s, 1H). M/z 593.3 (M+1).

Example H6

N-{4,6-Dimethoxy-2-[(3-morpholin-4-ylpropyl)amino]-pyrimidin-5-yl}-5-[(3,3,4,6-tetramethyl-2,3-dihydro-1-benzofuran-7-yl)methyl]-2-furamide.

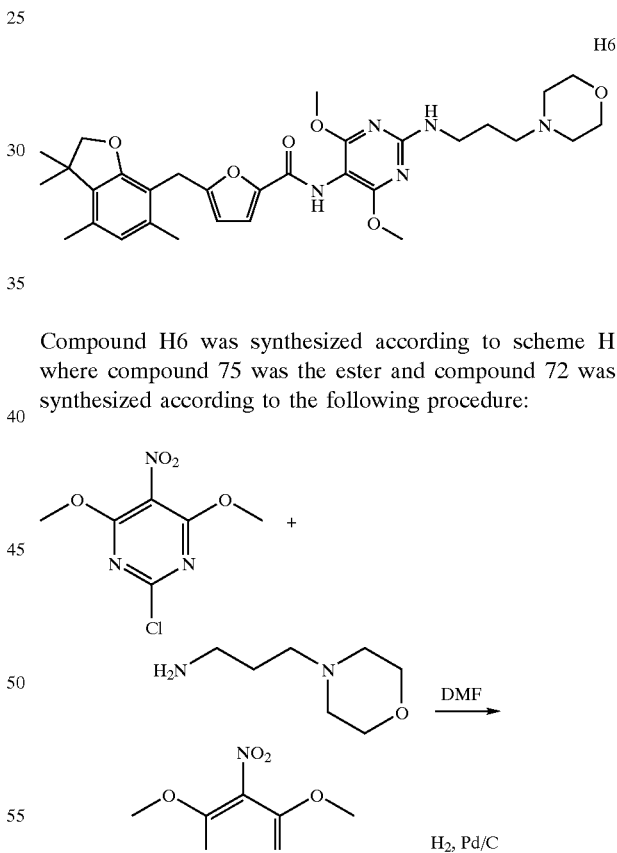

Compound H6 was synthesized according to scheme H where compound 75 was the ester and compound 72 was synthesized according to the following procedure:

-continued
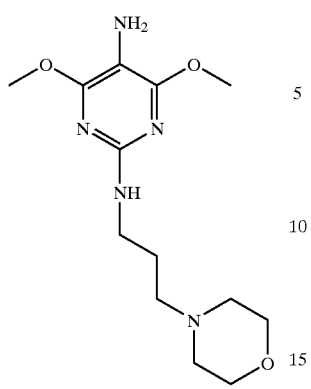
NMR and mass spectrometry data consistent with the title product were as follows:
$^1$HNMR (DMSO-$d_6$) 1.36(s, 6H), 1.71(s, 2H), 2.09(s, 3H), 2.17(s, 3H), 2.32(s, 4H), 2.90(s, 2H), 3.57(s, 4H), 3.73(s, 6H), 3.84(s, 2H), 5.91(s, 1H), 6.48(s, 1H), 7.04(s, 1H), 7.18(s, 1H), 8.81(s, 1H). M/z 580.3 (M+1).
The following set of examples were prepared according to Scheme I.
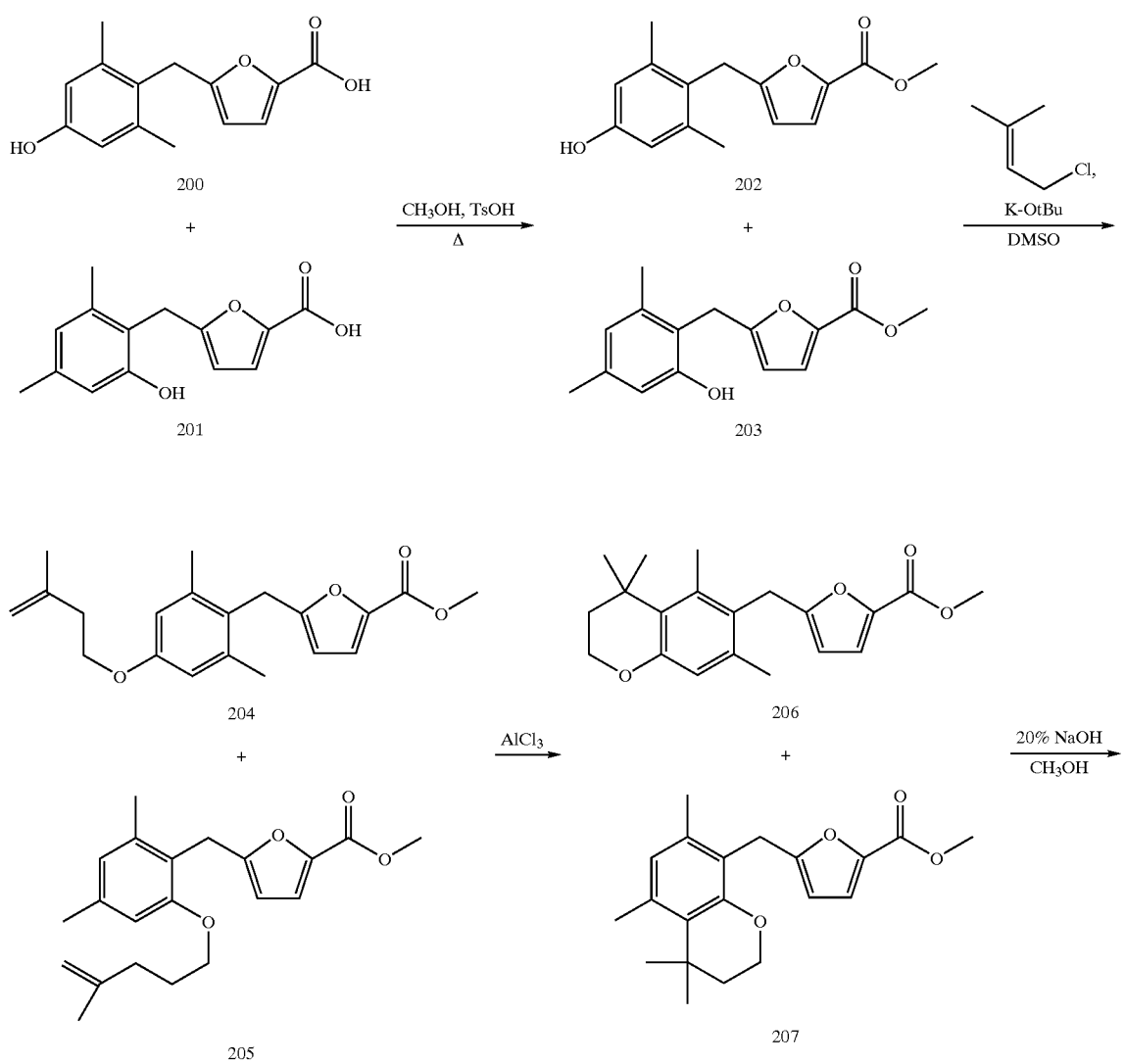

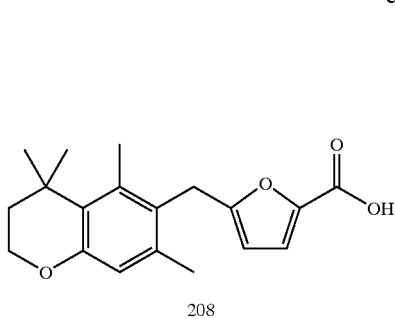 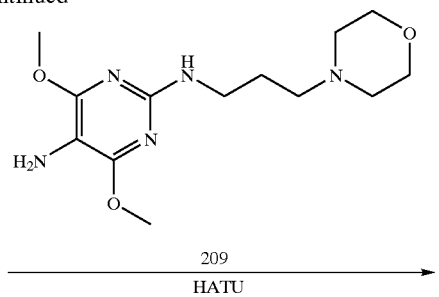

Example I1
N-{4,6-Dimethoxy-2-[(3-morpholin-4-ylpropyl)amino]pyrimidin-5-yl}-5-[(4,4,5,7-tetramethyl-3,4-dihydro-2H-chromen-6-yl)methyl]-2-furamide.

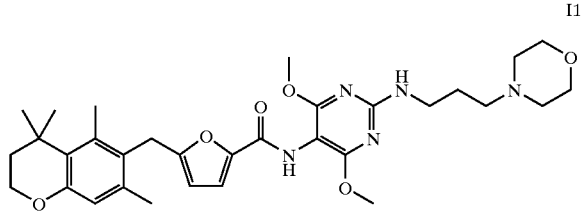

In a 500-mL round-bottom flask, a mixture of 5-(4-hydroxy-2,6-dimethylbenzyl)-2-furoic acid (200) and 5-(2-hydroxy-4,6-dimethylbenzyl)-2-furoic acid (201) (4.28 g, 17.38 mmol) and toluene (40 mL) were placed. To this solution p-toluenesulfonic acid monohydrate (3.31 g, 17.38 mmol) and methanol (10 mL, 246.87 mmol) were added. The reaction mixture was heated to 100° C. overnight. The reaction mixture was poured into water and extracted with ethyl acetate. The separated organic layer was washed with brine, dried over MgSO₄, and concentrated to yield methyl 5-(4-methoxy-2,6-dimethylbenzyl)-2-furoate (202) and methyl 5-(2-methoxy-4,6-dimethylbenzyl)-2-furoate (203) (4.52 g, 100% yield).

In a 500-mL round-bottom flask, a mixture of methyl 5-(4-methoxy-2,6-dimethylbenzyl)-2-furoate (202) and methyl 5-(2-methoxy-4,6-dimethylbenzyl)-2-furoate (203) (4.52 g, 17.38 mmol) and anhydrous DMSO (50 mL) were placed. To this solution, 1-chloro-3-methylbut-2-ene (1.91 g, 18.25 mmol) and potassium tert-butoxide (2.25 g, 20.07 mmol) were added. The reaction mixture was placed under nitrogen and stirred at room temperature for 3 hours. The reaction mixture was poured into, water and extracted with ethyl acetate. The separated organic layer-was washed with water (2×) and brine and dried over MgSO₄ then concentrated to yield a mixture of methyl 5-{2,6-dimethyl-4-[(3-methylbut-3-enyl)oxy]benzyl}-2-furoate (204) and methyl 5-{2,4-dimethyl-6-[(4-methylpent-4-enyl)oxy]benzyl}-2-furoate (205) (3.64 g, 64% yield).

In a 500-mL round-bottom flask, the mixture of methyl 5-{2,6-dimethyl-4-[(3-methylbut-3-enyl)oxy]benzyl}-2-furoate and methyl 5-{2,4-dimethyl-6-[(4-methylpent-4-enyl)oxy]beozyl}-2-furoate (3.64 g, 11.08 mmol) and dichloromethane (40 mL) were placed. To this solution AlCl₃ (2.96 g, 22.17 mmol) was added. The reaction mixture was stirred at room temperature for 2 hours. The solution poured into ice water to quench and extracted with dichloromethane. The separated organic layer was washed with brine and dried over MgSO₄. The crude mixture was purified by silica gel chromatography, eluted with hexane/ethyl acetate (19:1 v/v) to yield methyl 5-[(4,4,5,7-tetramethyl-3,4-dihydro-2H-chromen-6-yl)methyl]-2-furoate (206) (532 mg, 14.6% yield) and methyl 5-[(4,4,5,7-tetramethyl-3,4-dihydro-2H-chromen-8-yl)methyl]-2-furoate (207) (842 mg, 23% yield). Compound 206: ¹HNMR(CDCl₃) δ 1.31(s, 6H), 1.81 (m, 2H) 2.12(s, 3H), 2.21 (s, 3H), 2.62(t, 2H), 3.87 (s, 3H), 3.99 (s, 2H), 5.77(d, 1H), 6.55(s, 1H), 7.03 (d, 1H). Compound 207: ¹HNMR (CDCl₃) δ 1.24(s, 6H), 1.81 (m, 2H), 2.16(s, 3H), 2.23 (s, 3H), 2.59 (t, 2H), 3.85 (s, 3H), 3.99 (s, 2H), 5.85(d, 1H), 6.57 (s, 1H), 7.03 (d, 1H).

In a 100-mL round-bottom flask, methyl 5-[(4,4,5,7-tetramethyl-3,4-dihydro-2H-chromen-6-yl)methyl]-2-furoate (532 mg, 1.62 mmol) and methanol (5 mL) were placed. The reaction was stirred at room temperature overnight, and then the mixture was poured in water, acidified with HCl (6N) and extracted with ethyl acetate. The separated organic layer was washed with brine, dried over MgSO₄, and concentrated to yield 5-[(4,4,5,7-tetramethyl-3,4-dihydro-2H-chromen-6-yl)methyl]-2-furoic acid (208) (343.6 mg, 67.5% yield). ¹HNMR (CDCl₃) δ 1.31 (s, 6H), 1.82 (m, 2H), 2.13 (s, 3H), 2.21 (s, 3H), 2.62 (t, 2H), 4.01 (s, 2H), 5.82 (d, 1H), 6.55 (s, 1H), 7.16 (d, 1H). APCI-MS m/z 315 (M+1).

In a 50-mL round-bottom flask, 5-[(4,4,5,7-tetramethyl-3,4-dihydro-2H-chromen-6-yl)methyl]-2-furoic acid (114.53 mg, 0.364 mmol) and HATU (152.36 mg, 0.400 mmol) were dissolved in DMF (2 mL). To this solution 4,6-dimethoxy-N²-(3-morpholin-4-ylpropyl)pyrimidine-2,5-diamine (209) (108.32 364 mmol) and triethylamine, (91.98 mg, 0.911 mmol) were added. The reaction mixture was stirred at room temperature overnight. The solution was filtered through a PTFE (polytetrafluoroethylene) membrane micro filter. The crude mixture was purified by HPLC C18 column, eluted with aceonitrile/water/0.1% ACOH (30%

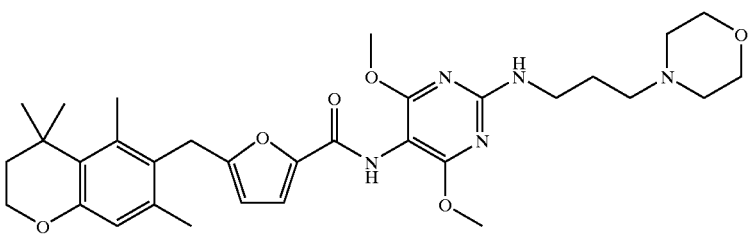

ACN-70% CAN over 30 min) to yield N-{4,6-dimethoxy-2-[(3-morpholin-4-ylpropyl)amino]pyrimidin-5-yl}-5-[(4,4,5,7-tetramethyl-3,4-dihydro-2H-chromen-6-yl)methyl]-2-furamide (I1) (15.9 mg, 7% yield). $^1$H NMR (CDCl$_3$) δ 1.31(s, 6H), 1.80(m, 4H, J=6.80, 6.42, 6.04 Hz), 2.15(s, 3H), 2.23(s, 3H), 2.49(m, 6H), 2.63(t, 2H, J=6.80 Hz), 3.49(q, 2H, J=6.04, 5.67 Hz), 3.75(t, 4H, J=4.53 Hz), 3.87(s, 6H), 3.98(s, 2H), 5.74(s, 1H), 5.80(d, 1H, J=3.02 Hz), 6.56(s, 1H), 7.01 (d, 1H, J=3.02 Hz), 7.05(s, 1H). (M+1) 594.2.

Example I2

N-(4,6-Dimethoxy-2-{[3-(4-methylpiperazin-1-yl)propyl]amino}pyrimidin-5-yl)-5-[(4,4,5,7-tetramethyl-3,4-dihydro-2H-chromen-6-yl)methyl]-2-furamide.

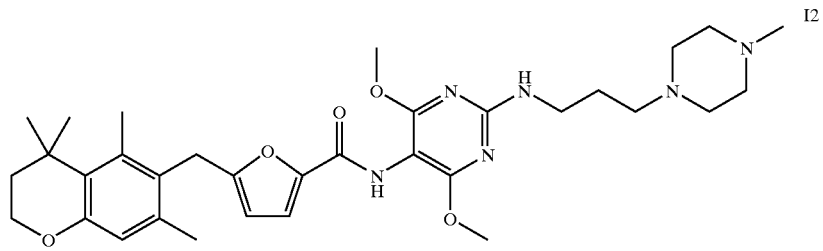

Compound I2 was synthesized in a manner analogous to compound I1 according to scheme I: $^1$H NMR (CDCl$_3$) δ 1.31(s, 6H), 1.77(m, 4H), 2.16(s, 2H), 2.24(s, 3H), 2.30(s, 3H), 2.48(t, 6H, J=7.18, 6.42 Hz), 2.64(t, 4H, J=6.80, 6.42 Hz), 3.45(q, 2H, J=6.04, 5.67 Hz), 3.89(s, 6H), 3.99(s, 2H), 5.81(m, 2H, J=3.02 Hz), 6.58(s, 1H), 7.00(d, 1H, J=3.02 Hz), 7.08(s, 1H). (M+1) 607.3.

Example I3

N-(2-{[3-(Dimethylamino)propyl]amino}-4,6-dimethoxypyrimidin-5-yl)-5-[(4,4,5,7-tetramethyl-3,4-dihydro-2H-chromen-6-yl)methyl]-2-furamide.

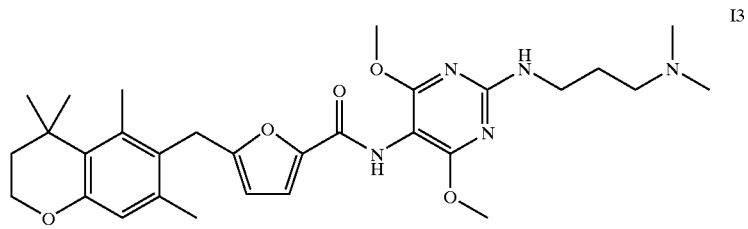

Compound I3 was synthesized according to scheme I. $^1$H NMR (CDCl$_3$) δ 1.32(s, 6H), 1.87(m, 4H), 2.15(s, 3H), 2.23(s, 3H), 2.46(s, 6H), 2.66(m, 2H), 3.47(q, 2H, J=6.04, 5.67 Hz), 3.88(s, 6H), 3.97(s, 2H), 5.37(s, 1H), 5.78(d, 2H, J=3.02 Hz), 6.55(s, 1H), 7.01(d, 1H, J=3.02 Hz), 7.07(s, 1H). (M+1) 552.3.

Example J1

N-(2-{[3-(dimethylamino)propyl]amino}-4,6-dimethoxypyrimidin-5-yl)-5-[(1,1,3,3,6-pentamethyl-2,3-dihydro-1H-inden-5-yl)methyl]-2-furamide.

The title compound was prepared according to the following scheme:

Scheme J

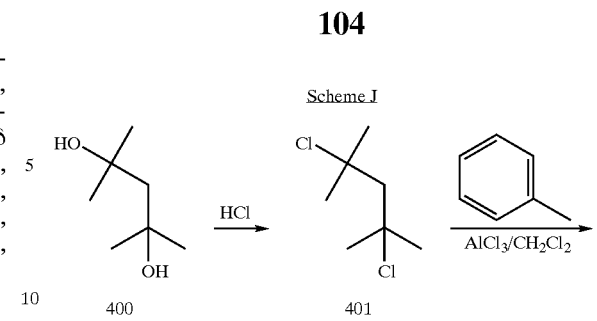

-continued

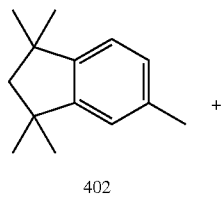

+

-continued

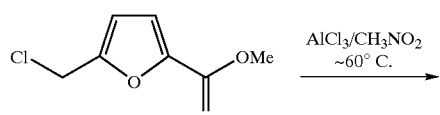

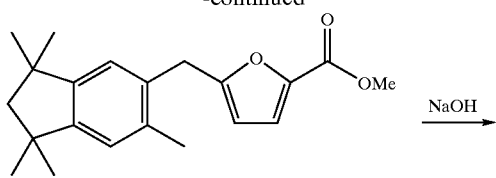

404

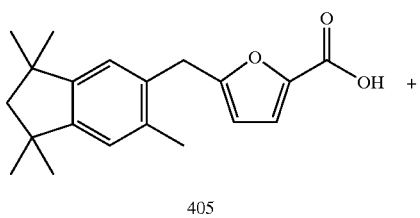

405

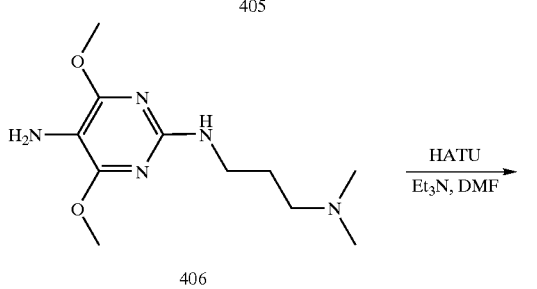

406

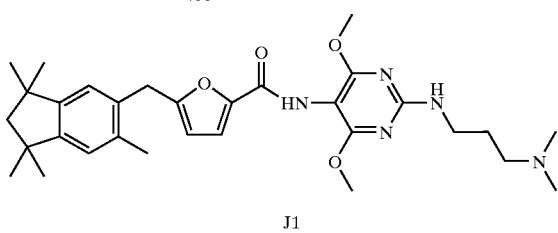

J1

Concentrate HCl (excess) was added to diol 400 (neat) and allowed to stir for 30 minutes. The crude dichloride compound 401 was extracted with hexane. The extraction was passed through a silica gel column to give a purified product 401. Compound 401 was dissolved in CH$_2$Cl$_2$ and to this solution was added toluene (10 eq.), followed by addition of AlCl$_3$ (0.5 eq.) at room temperature slowly. The solution was stirred for 1 hour (h) and poured into ice water. The organic layer was extracted with EtOAc and concentrated. The crude product was purified on a silica gel column (Hexane/EtOAc, 10:1) to give compound 402. To solution of compounds 402 and 403 in CH$_3$NO$_2$ was added AlCl$_3$ (1.0 eq.). The solution was heated to 60° C. for 5 hour and quenched with ice water, extracted and concentrated. The crude material was purified by a silica gel column to give compound 404, which was then treated with 20% NaOH in MeOH for 2 hours to give compound 405. Compound 405 was dissolved in DMF and to the solution was added Et$_3$N and HATU. After being stirred at rt. for 15 minutes, to the solution was added a solution of compound 406 in DMF and allowed to stir for 1 hour. Crude mixture was purified by HPLC (CH$_3$CN/H$_2$O 30% to 90% in 30 minutes) to give J1:

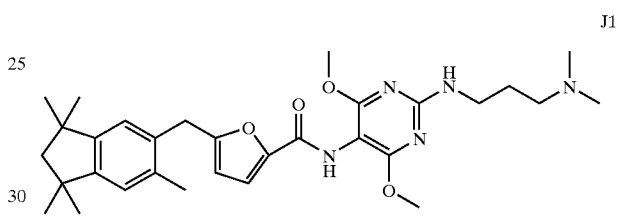

J1

1.27(s, 6H), 1.30(s, 6H), 1.75(q, 2H, J=6.88 Hz), 1.88(s, 2H), 2.24(s, 6H), 2.29(s, 3H), 2.36(t, 2H, J=7.06 Hz), 3.45(dd, 2H, J=6.59, 6.22 Hz), 3.85(s, 6H), 3.97(s, 2H), 5.38(dd, 1H, J=5.84, 5.27 Hz), 6.00(d, 1H, J=3.20 Hz), 6.87(s, 1H), 6.94(s, 1H), 7.08(d, 2H, J=2.83 Hz).

Examples K1 and K2 were prepared according to the following scheme:

Scheme K

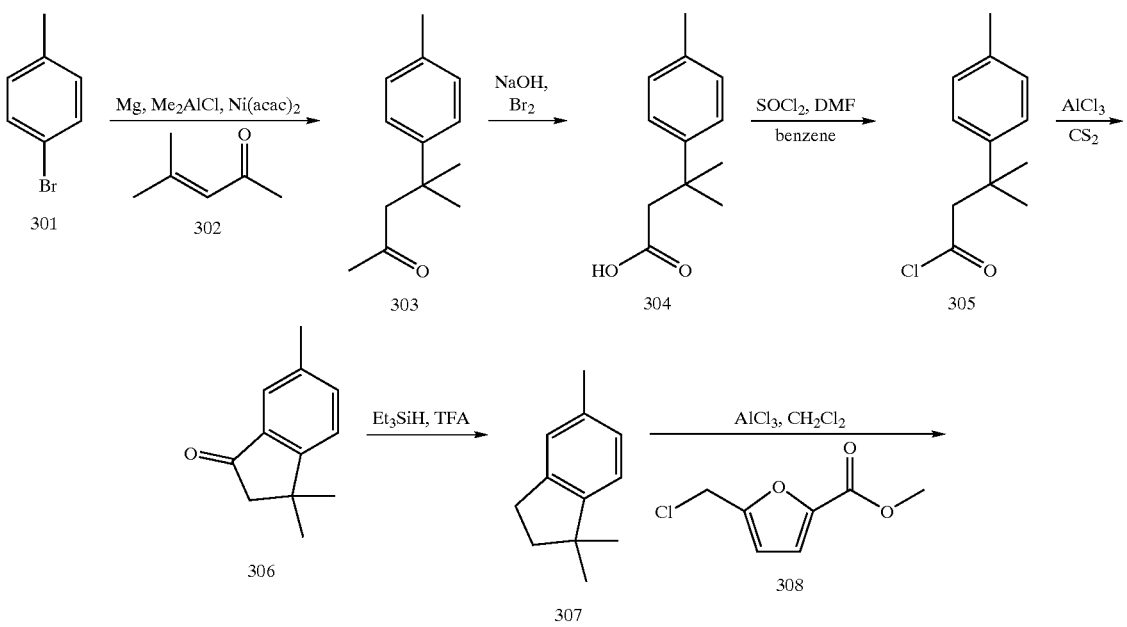

-continued

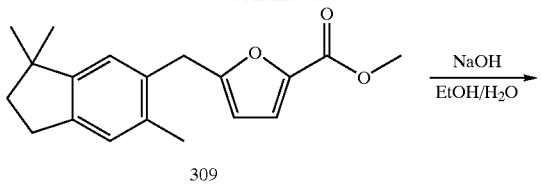

309

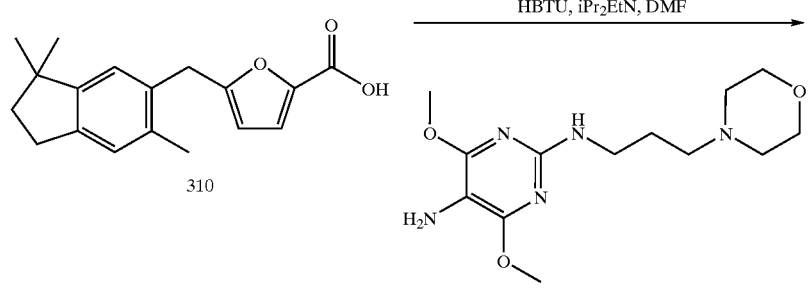

310 311

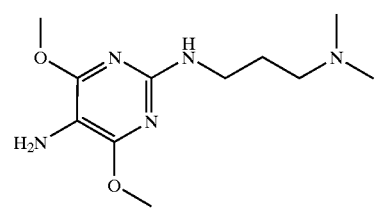

312

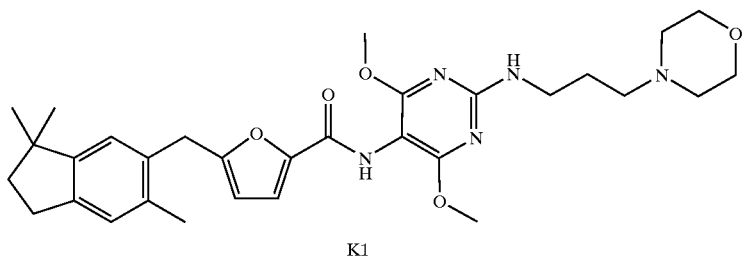

K1

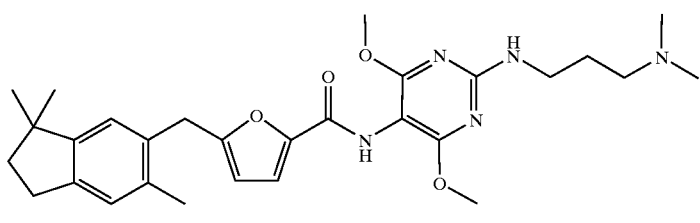

K2

A suspension of Mg (8.03 g, 330 mmol) in anhydrous THF (100 mL) was treated with 4-bromotoluene (50 g, 300 mmol) at reflux under nitrogen overnight. After cooling to room temperature, the resulting Grignard solution was cannula transferred into a solution of dimethylaluminum chloride in hexane (1.0 M, 277 mL, 277 mmol) at −20° C. The mixture was further stirred at −20° C. for 0.5 h. Then enone (25.2 g, 231 mmol) in anhydrous THF (350 mL) was added dropwise at −20° C., followed by nickel(II) acetylacetonate [Ni(acac)$_2$] (2.97 g, 11.6 mmol). The reaction mixture was stirred at 0° C. for an additional 4 h before allowing it to warm to room temperature. Then it was quenched with aqueous ammonium chloride solution, stirred for 0.5 h, and extracted with ethyl acetate. The combined organic layers were dried over anhydrous sodium sulfate and concentrated, to give about 29 g of crude material, which was subjected to fractional distillation to afford 4-methyl-4-(4-methylphenyl)pentan-2-one (303) as a colorless liquid (24 g, 55%). Boiling pt 94–97° C. at 2 mm Hg. $^1$H NMR (CDCl$_3$) δ 1.41 (s, 6H), 1.79 (s, 3H), 2.32 (s, 3H), 2.72 (s, 2H), 7.12 (d, 2H), 7.25 (d, 2H).

Bromine (73.4 g, 460 mmol) was added dropwise into dioxane (350 mL) with stirring at 0° C. The resulting solution was added dropwise into sodium hydroxide (71 g, 1.77 mol) in water (725 mL) with mechanical stirring, keeping the temperature below 0° C. The hypobromite solution this prepared was added dropwise into a solution of 4-methyl-4-(4-methylphenyl)pentan-2-one (24 g, 126 mmol) in dioxane/water (1:1 v/v, total 700 mL) at 0° C. with stirring. The reaction mixture was further stirred at 0° C. for 3 h after complete addition of hypobromite solution. The temperature of the reaction mixture was allowed to warm to room temperature before adding sodium hydrogensulfite (9.5 g). The resulting solution was poured into ice-water (2 L) and extracted with dichloromethane (5×150 mL). The combined dichloromethane layers were dried over anhydrous sodium sulfate and concentrated to give a viscous oil. The oil thus obtained was dissolved in dichloromethane (100 mL) and washed with saturated sodium bicarbonate (100 mL). The aqueous layer was-acidified with 10% hydrochloric acid to give a pale brownish solid, which was filtered and dried at 50° C. under high vacuum overnight to afford 3-methyl-3-(4-methylphenyl)butyric acid (304) (8.9 g, 37%). Melting pt. 76–78° C.; $^1$H NMR (CDCl$_3$) δ 1.44 (s, 6H), 2.32 (s, 3H), 2.63 (s, 2H), 7.12 d, J=9.0 Hz, 2H), 7.25 (d, J=6.0 Hz, 2H).

A solution containing 3-methyl-3-(4-methylphenyl) butyric acid (8.5 g, 44.2 mmol) and anhydrous DMF (5 drops) in anhydrous benzene (110 mL) was refluxed under nitrogen as thionyl chloride (8.1 mL, 110 mmol)was added dropwise under nitrogen. The solution was refluxed an additional 15 h after complete addition of thionyl chloride. The dark brownish reaction mixture was allowed to cool to room temperature and concentrated under vacuum. TLC analysis of the crude material showed complete disappearance of the starting material. Presence of DMF was evident from the proton NMR. The crude material, 3-methyl-3-(4-methylphenyl)butyric acid chloride (305) (about 10 g), thus obtained was used in the next step without further purification.

A suspension of aluminum chloride (8.8 g, 65.4 mmol) in carbon disulfide was cooled to 0° C. as acid chloride (10 g, 44.2 mmol where previous step was quantitative) in carbon disulfide (5 mL) was added dropwise under nitrogen with stirring. The suspension was allowed to warm to room temperature and further stirred for 15 h. The reaction mixture was poured into ice-water. The aqueous layer was extracted with dichloromethane. The combined dichloromethane layers were washed with saturated sodium bicarbonate, brine and dried over anhydrous sodium sulfate. The resulting brown oil was distilled using Kugelrohr apparatus to give 3,3,6-trimethylindan-1-one (306) (4.72 g, 61%) as a colorless liquid. Boiling pt 100–110° C. at 0.1 mmHg; $^1$H NMR (CDCl$_3$) δ 1.40 (s, 6H), 2.39 (s, 3H), 2.58 (s, 2H), 7.37-7.49 (m, 2H), 7.51 (s, 1H).

A solution of 3,3,6-trimethylindan-1-one (2.62 g, 15 mmol) in trifluoroacetic acid (12 mL, 150 mmol) was stirred at room temperature under nitrogen as triethylsilane (5.3 mL, 33 mmol) was added dropwise. The solution was stirred overnight. The reaction mixture was treated with saturated sodium bicarbonate, followed by extraction with ether. The combined ether layers were dried over anhydrous sodium sulfate and concentrated. MS analysis of the crude material showed the presence of triethylsilanol and hexaethyldisiloxane as the major by-products. The crude material was subjected to fractional distillation to afford 1,1,5-trimethylindane (307) (2.19 g, 92%) as a colorless liquid. Boiling pt 86–88° C. at 0.8 mmHg; $^1$H NMR (CDCl$_3$) δ 1.24 (s, 6H), 1.90 (t, 2H), 2.31 (s, 3H), 2.85 (t, 2H), 7.02 (m, 3H).

A solution of 1,1,5-trimethylindane (2.60 g, 16.2 mmol) and methyl 5-chloromethyl-2-furoate (2.84 g, 16.2 mmol) in dichloromethane (90 mL) was stirred at reflux under nitrogen as aluminum chloride (2.70 g, 20.3 mmol) was added in small portions. The suspension was refluxed for an additional 2 h. The reaction mixture was cooled to room temperature and any excess aluminum chloride was quenched with ice-water. The aqueous layer was extracted with dichloromethane. The combined dichloromethane layers were dried over anhydrous sodium sulfate and concentrated. The crude material thus obtained was purified by silica gel chromatography using hexane/ethyl acetate (95:5) as the eluant, to afford methyl 5-[3,3-dimethyl-2,3-dihydro-1H-inden-5-yl)methyl]-2-furoate (309) (1.55 g, 32%) as a pale brown solid. $^1$H NMR (CDCl$_3$) δ 1.24 (s, 6H), 1.91 (t, 2H), 2.27 (s, 2H), 2.84 (t, 2H), 3.87 (s, 3H), 3.99 (s, 2H), 5.85 (d, 1H), 6.94 (s, 1H), 7.00–7.14 (m, 2H); APCI-MS m/z 299.1 (M+1).

A solution containing methyl 5-[3,3-dimethyl-2,3-dihydro-1H-inden-5-yl)methyl]-2-furoate (1.4 g, 4.7 mmol) and sodium hydroxide (245 mg, 6.2 mmol) in ethanol/water (2.5:1 v/v, total 65 mL) was stirred at room temperature for 3 h. After work-up, 5-[3,3-dimethyl-2,3-dihydro-1H-inden-5-yl)methyl]-2-furoic acid (310) (1.20 g, 90%) was obtained as a yellowish-white solid. $^1$H NMR (CDCl$_3$) δ 1.14 (s, 6H), 1.80 (t, (s, 1H); APCI-MS m/z 285.1 (M+1).

Example K1

N-{4,6-Dimethoxy-2-[3-morpholin-4-ylpropyl)amino]-pyrimidin-5-yl}-5-[(3,3,6-trimethyl-2,3-dihydro-1H-inden-5-yl)methyl]-2-furamide

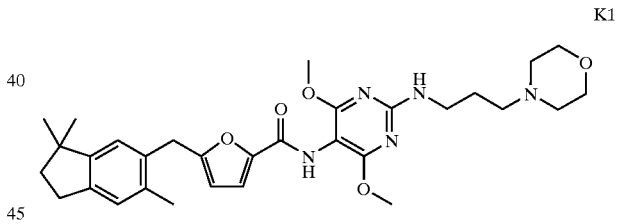

K1

A solution of furoic acid 310 (285 mg, 1 mmol), HBTU (380 mg, 1 mmol), diisopropylethylamine (170 ML, 1 mmol) and pyrimidinylamine 311 (298 mg, 1 mmol) in anhydrous DMF (7.5 mL) was stirred under nitrogen for 15 h. The reaction mixture was concentrated under vacuum before dissolving in chloroform. The resulting solution was washed with saturated sodium bicarbonate, brine before drying over anhydrous sodium sulfate. The chloroform layer was concentrated and the resulting crude material was purified by silica gel column chromatography using 8N ammonia in methanol/chloroform (6:94) as the eluant to give N-{4,6-dimethoxy-2-[3-morpholin-4-ylpropyl)amino] pyrimidin-5-yl}-5-[(3,3,6-trimethyl-2,3-dihydro-1H-inden-5-yl)methyl]-2-furamide (K1) (338 mg, 62%) as a pale yellow solid. $^1$H NMR (CDCl$_3$) δ 1.24 (s, 6H), 1.59 (m, 2H), 1.78 (t, 2H), 1.92 (t, 2H), 2.27 (s, 2H), 2.48 (m, 6H), 3.47 (m, 2H), 3.74 (t, 4H), 3.87 (s, 6H), 3.99 (s, 2H), 5.60 (bt, 1H), 5.95 (d, 1H), 6.92 (s, 1H), 6.95–7.05 (m, 3H); APCI-MS m/z 564.2 (M+1).

Compound K2
N-(2-{[3-9Dimethylamino)propylamino}-4,6-dimethoxypyrimidin-5-yl}-5-[(3,3,6-trimethyl-2,3-dihydro-1H-inden-5-yl)methyl]-2-furamide

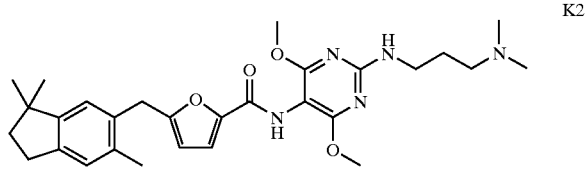

A solution of furoic acid 310 (285 mg, 1 mmol), HBTU (380 mg, 1 mmol), diisopropylethylamine (170 mL, 1 mmol) and pyrimidinylamine 312 (256 mg, 1 mmol) in anhydrous DMF (7.5 mL) was stirred under nitrogen for 15 h. The reaction mixture was concentrated under vacuum before dissolving in chloroform. The resulting solution was washed with saturated sodium bicarbonate, brine before drying over anhydrous sodium sulfate. The chloroform layer was concentrated and the resulting crude material was purified by silica gel column chromatography using 8N ammonia in methanol/chloroform (18:82) as the eluant to give N-(2-{[3-9dimethylamino)propylamino}-4,6-dimethoxypyrimidin-5-yl}-5-[(3,3,6-trimethyl-2,3-dihydro-1H-inden-5-yl)methyl]-2-furamide, K2 (297 mg, 57%) as a pale yellow solid.

$^1$H NMR (CDCl$_3$) δ 1.24 (s, 6H), 1.82 (quintet, 2H), 1.95 (t, 2H), 2.25 (s, 6H), 2.26 (s, 3H), 2.48 (t, 2H), 2.88 (t, 2H), 3.44 (m, 2H), 3.88 (s, 6H), 3.99 (s, 2H), 5.30 (d, 2H), 6.90–7.10 (m, 3H); APCI-MS m/z 522.2 (M+1).

Biological Testing and Enzyme Assays
In Vitro Assays:

Assessment of GnRH Receptor Activation Using Microphysiometry

By performing exemplary assays described below, the functionality of the compounds of the invention as GnRH antagonists may be confirmed.

Materials and Methods

GnRH, Ac-D-2-Nal-p-chloro-D-Phe-β-(3-pyridyl)-D-Ala-Ser-Lys(nicotinoyl)-D-Lys(nicotinoyl)-Leu-Lys(isopropyl)-Pro-D-Ala-NH$_2$ (Antide), the superagonist peptide [D-Ala$^6$, des-Gly$^{10}$]proethylamide$^9$-LHRH (GnRH-A), and TRH may be purchased from Bachem (Torrance, Calif.). Cell Culture media and forskolin may be purchased from Sigma (St. Louis, Mo.). Fetal bovine serum (FBS) and penicillin/streptomycin are available from Omega Scientific, Inc. (Tarzana, Calif.). G418 may be obtained from Gemini (Calabasas, Calif.). Staurosporine, Rp-adenosine 3',5'-cyclic monophosphothioate triethylamine (Rp-cAMPS), PMA, and 5-(N-methyl-N-isobutyl)-amiloride (MIA) are available from RBI (Natick, Mass.). 2-[1-(3-Dimethylaminopropyl)indol-3-yl]-3-(indol-3-yl)maleimide (GF 109203X) may be purchased from Tocris (Ballwin, Mo.).

Cell Culture. GGH$_3$ cells (Dr. William Chin, Harvard Medical School, Boston, Mass.) are grown in low glucose Dulbecco's modified Eagle's medium (DMEM) containing 100 U/mL penicillin/streptomycin, 0.6 g/L G418 and 10% heat-inactivated FBS.

Total Inositol Phosphates Measurement

The activity of various GnRH agents is initially assessed utilizing an assay that measures accumulation of total inositol phosphates. Approximately 200,000 GGH$_3$ cells/well are plated onto 24-well tissue culture plates using DMEM media. The following day, cells are loaded with [$^3$H] myoinositol (0.5 Ci/ml) for 16–18 hours in inositol-free medium. The medium is aspirated and the cells rinsed with serum-free DMEM. Cells are stimulated with GnRH (0.1 nM–1 µM) or the superagonist, GnRH-A (0.01 nM–100 nM) dissolved in DMEM media in a total volume of 1 mL containing 10 mM LiCl at 37° C. for 45 minutes. The media is replaced with 1 mL ice-cold 10 mM formic acid, which stops the reaction and also serves to extract cellular lipids. Inositol phosphates are separated by ion-exchange chromatography on Dowex columns, which are washed with 2.5 mL of 10 mM myoinositol and 10 mM formic acid. The columns are then-washed with 5 mL of 60 mM sodium formate and 5 mM borax, and total inositol phosphates are eluted with 5 mL 1M ammonium formate, 0.1 M formic acid. The column eluates are added to liquid scintillation vials containing 15 ml of scintillation cocktail and are counted by liquid scintillation counting.

Preparation of $^{125}$I-GnRH-A radioligand

The radioiodinated agonist analog of GnRH, $^{125}$I-GnRH-A, is used as the radioligand. One µg of GnRH-A diluted in 0.1M acetic acid is added to an Ioogen®-coated borosilicate glass tube (Pierce) containing 35 µl of 0.05 M phosphate buffer (pH 7.4–7.6) and 1 mCi of Na[$^{125}$I]. The reaction mixture is vortexed and incubated for 1 min at room temperature. Two; ml of 0.5 M acetic acid is added to the reaction tube and the mixture is added to a C18 Sep-Pak cartridge: The cartridge is washed with subsequent washes of 5 ml H$_2$O and 5 ml 0.5M acetic acid and then eluted with 5×1 ml of 60% CH$_3$CN/40% 0.5M acetic acid. The eluate is diluted with 3× volume of HPLC buffer A (0.1% TFA in H$_2$O) and loaded onto a C18 column. The iodinated product is eluted over 20–25 min with a gradient of 25–100% CH$_3$CN containing 0.1% TFA. The radioactive fractions (750 µl/fraction) are collected into clean polypropylene tubes containing 100 µl of 10% BSA. Fractions are assessed for biological activity by radioligand binding.

Competition Radioligand Binding

Approximately two million GGH$_3$ cells/tube are utilized for radioligand binding. $^{125}$I-GnRH-A (approximately 0.1–0.3 nM) is incubated with cells in the presence or absence of competing agents in a final volume of 300 µl binding assay buffer [50 mM HEPES (pH 7.4), 1 mM EDTA, 2.5 mM MgCl$_2$, and 0.1% BSA] to test the ability of compounds to displace agonist binding. Reactions are performed on ice for 2 hr and stopped by the addition of 2 ml of ice-cold PBS wash buffer (50 mM NaPO$_4$, 0.9% NaCl, 2 mM MgCl$_2$, and 0.02% NaN$_3$, pH 7.4) and rapid filtration onto GF/C filters presoaked with 0.05% polyethylenimine utilizing a Brandel cell harvester. Filters are counted on a gamma counter.

Microphysiometry

The Cytosensor® Microphysiometer (Molecular Devices, Sunnyvale, Calif.) is a real-time, noninvasive, nonradioactive semiconductor-based system for monitoring the cellular responses to various stimuli. It is based on a pH-sensitive silicon sensor, the light-addressable potentiometric sensor which forms part of a microvolume flow chamber in which cultured cells are immobilized (14, 15, 17). GGH$_3$ cells are seeded in low-buffered minimal essential media (MEM, Sigma) containing 25 mM NaCl and 0.1% BSA at a density of 500,000 cells/capsule onto the polycarbonate membrane (3 μm porosity) of cell capsule cups (Molecular Devices, Sunnyvale, Calif.). Capsule cups are transferred to sensor chambers where cells are held in close apposition to a silicon sensor within a sensor chamber, which measures small changes in pH in the microvolume of the sensor chamber. Low-buffered medium is pumped continuously across the cells at a rate of approximately 100 μl/min from one of two fluid reservoirs. A selection valve determines which reservoir from which fluid is perfused onto the cells.

The Cytosensor®Microphysiometer generates a voltage signal, which is a linear function of pH, every second. In order to measure acidification rates, flow to the sensor chamber containing the cells is periodically interrupted, allowing excreted acidic metabolites to build up in the extracellular fluid of the cells. Cells are maintained at 37° C. on a two-minute flow cycle with cells being perfused with media for 80 seconds followed by 40 seconds in which the flow of media is stopped. During this 40-second interval, acidification rates are measured for a 30 sec interval. In this fashion, a single acidification rate is calculated every two minutes. The Cytosensor® Microphysiometer device contains eight such sensor units, allowing for eight simultaneous experiments to be performed. Each unit is individually programmed utilizing a computer linked to the system.

$GGH_3$ cells are initially equilibrated in the low-buffered MEM media for a period of 30–60 min in which basal acidification rates (measured as $\mu V/sec$), in the absence of any stimuli, are monitored. When the basal rate of acidification changes by less than ten percent over a period of twenty minutes, experiments are initiated. Time course experiments are performed to determine the optimal time for agent exposure prior to acidification rate measurement and the duration of exposure needed to obtain peak acidification responses to various agents. From these time course experiments, it has been determined that cells should be exposed to GnRH agents at least one minute prior to collection of acidification rate data. Peak acidification rates usually occur in the first two-min exposure cycle. When the effects of various agents are measured, cells are pretreated for 20 min with test compound diluted in low-buffered MEM containing 1% DMSO final concentration prior to exposure of the cells for 4 min to a solution; containing GnRH or PMA at appropriate concentration in the presence of inhibitor.

Cyclic AMP Measurement

The ability of various compounds to increase basal cAMP formation in $GGH_3$ cells is assessed utilizing 96-well adenylyl cyclase flashplates purchased from New England Nuclear (NEN, Boston, Mass.). Cells (approximately 50,000 cells/well) are incubated with either forskolin (10 nM 10 μM), GnRH (1 nM–1 μM) or GnRH-A (0.1 nM–100 nM) in a total volume of 100 μl on flashplates for 20 minutes at room temperature to assess for agonist activity. 100 μl of detection mix containing $^{125}I$-cAMP is added to quench reactions according to the manufacturer's instructions. Plates are counted on a Packard TopCount after approximately two hours. Cyclic AMP levels are determined from standard curves generated to non-radioactive cAMP standards (10 nM–1 μM).

Data Analysis

Cytosensor® Microphysiometer data are normalized utilizing Cytosoft® software (Molecular Devices, Sunnyvale, Calif.). $EC_{50}$ values for agonists and $IC_{50}$ values for inhibitors are generated utilizing Prism™ (version 2.01, GraphPad Stare, San Diego, Calif.), a computer graphics and statistics program. Values for multiple experiments are presented as means±SE of at least three replicate experiments.

Effect of Compounds on $^{125}I$-GnRH-A Binding to $GGH_3$ Cells

In order to assess the specific functionality, compounds were assessed for their ability to inhibit $^{125}I$-GnRH-A binding to $GGH_3$ cells. The peptide ligands GnRH, GnRH-A, and Antide, but none of the tested compounds of the invention, blocked $^{125}I$-GnRH-A binding to these cells. Thus, the compounds of the invention are GnRH antagonists.

Determination of Binding Inhibition Constants

Using the assay described below, $K_i$ values for compounds of the invention were determined.

Chemicals and Reagents

GnRH (pGlu-His-Trp-Ser-Tyr-Gly-Leu-Arg-Pro-Gly-$NH_2$) was purchased from Bachem (Torrance, Calif.). Cell Culture media was purchased from Sigma (St. Louis, Mo.). Fetal bovine serum (FBS) was from Omega Scientific, Inc. (Tarzana, Calif.). G418 and penicillin/streptomycin were from Gemini (Calabasas, Calif.). Newborn calf serum was from Summit Biotech (Fort Collins, Colo.). All other reagents were of the highest quality from standard sources.

Cell Culture

HEK 293 cells stably transfected with mouse or human GnRH receptors as described above were grown in Dulbecco's high-glucose, modified Eagle's medium (DMEM) supplemented with 0.2% G418, 10% fetal bovine serum (FBS) and 100 U/mL penicillin/streptomycin. $GH_3$ cells stably transfected with the rat GnRH receptor ($GGH_3$) were provided by Dr. William Chin (Harvard Medical School, Boston, Mass.). These cells have been extensively characterized previously (Kaiser et al., 1997). The cells were grown in low glucose DMEM containing: 100U/mL penicillin/streptomycin, 0.6% G418 and 10% heat-inactivated FBS.

Cell Membrane Preparation

HEK 293 cells containing mouse or human receptors, or rat pituitaries (Pel Freez Biologicals, Rogers, Ark.) were homogenized in buffer A containing: 50 mM Tris (pH 7.4), 0.32 M sucrose, 2 mM EGTA, 1 mM PMSF, 5 μg/ml aprotinen, 5 μg/ml Pepstatin A, and 1 μg/ml leupeptin. Homogenized cells were centrifuged at 4° C. at 20,000×g for 25 minutes, re-suspended in buffer A and re-centrifuged at 4° C. at 20,000×g for an additional 25 minutes. Total membrane protein was determined with a BCA kit (Pierce, Rockford, Ill.). Membranes were stored at −70° C. at a final membrane protein concentration of approximately 5 mg/ml.

Pharmacokinetics

Rats (male or female, 200–225 g) were prepared with indwelling jugular vein cannula as described by Harms et al., *Applied Physiol.* 36:391–398 (1974), and allowed to recover overnight with free access to the standard vivarium chow and water. The compounds were administered to female rats at 5 mg/kg i.v. and 10 mg/kg p.o. as solutions in 10% DMSO+10% cremophor+80% saline or 10% cremophor+90% saline. The male rats were dosed orally at 50 mg/kg in the vehicles specified in Table 3. The blood samples were withdrawn at specific times, plasma was immediately separated and compound extracted with ethyl acetate. The samples were analyzed by LC-MS using 30–90% gradient of ACN in 50 mM ammonium acetate.

The pharmacokinetic parameters were calculated using WinNonlin software (Scientific Consulting Inc.). The bioavailability was calculated as AUCp.o./AUCi.v., where AUCp.o. and AUC i.v. are areas under the plasma concentration-time curve after oral and i.v. administration, respectively.

Radioligand Preparation

The radioiodinated agonist analog of GnRH, [des-Gly$^{10}$, D-Ala$^6$]GnRH ethylamide ($^{125}$I-GnRH-A), was used as the radioligand. One µg of GnRH-A diluted in 0.5 M phosphate buffer (pH 7.4) was added to an Iodogen®-coated borosilicate glass tube (Pierce, Rockford, Ill.) containing 35 µl of 0.05 M phosphate buffer (pH 7.4–7.6) and 1 mCi of Na[$^{125}$I]. The reaction mixture was vortexed and incubated for 1 minute at room temperature. After one minute, the mixture was vortexed and allowed to incubate for an additional minute. 2 ml of 0.5 M acetic acid/1% BSA was added to the reaction tube and the mixture was added to a C18 Sep-Pak cartridge. The cartridge was washed with subsequent washes of 5 ml H$_2$O and 5 ml 0.5 M acetic acid and then eluted with 5×1 ml of 60% CH$_3$CN/40% 0.5 M acetic acid. The eluate was diluted with 3× volume of HPLC buffer A (0.1% TFA in H$_2$O) and loaded onto a C18 column. The iodinated product was eluted over 20–25 min with a gradient of 25–100% CH$_3$CN containing 0.1% TFA. The radioactive fractions (750 µl/fraction) were collected into clean polypropylene tubes containing 100 µl of 10% BSA. Fractions were assessed for biological activity by radioligand binding. Specific activity of the radioligand was approximately 2200 Ci/mmol.

Radioligand Binding Assays

Membranes were diluted to 0.01–0.5 mg/ml (depending upon the species of receptor) with assay buffer containing 50 mM HEPES (pH 7.4), 1 mM EDTA, 2.5 mM MgCl$_2$, and 0.1% BSA. Membranes (diluted to utilize similar receptor numbers between assays) were incubated with approximately 0.04–0.06 nM $^{125}$I-GnRH-A in the presence or absence of competing agents (0.1–10,000 nM) in a total volume of 200 µl in 96-well polypropylene plates for 1 hour at room temperature. Assays were stopped by rapid filtration onto 96-well GF/C filters soaked in 0.1% polyethylenimine (PEI) utilizing a Packard 96-well cell harvester. Filters were washed three times with ice-cold PBS (50 mM NaPO$_4$, 0.9% NaCl, 2 mM MgCl$_2$, and 0.02% NaN$_3$, pH 7.4). 35 µl of scintillation cocktail was added to each filter well and filters were counted on a Packard Topcount. Control dose-response curves were generated to GnRH (0.1 nM–100 nM) in each competition binding experiment. Binding inhibition constants (K$_i$) for the GnRH agents were calculated and are provided in Table 2 below. K$_i$ values were calculated from IC$_{50}$ values according to Cheng et al., *Biochemical Pharmacol.* 22: 3099–3108, 1973.

$$K_i = \frac{IC_{50}}{1 + \frac{[\text{ligand}]}{K_d \text{ of ligand}}}$$

TABLE 1

K$_i$ for GnRH Agents:
Inhibition Binding of $^{125}$I-GnRH-A to
GnRH Receptors of Various Species

| Example No. | GnRH Receptor | K$_i$ (nM) |
|---|---|---|
| A1 | Human | 4.6 |
|  | Mouse | 4.2 |
|  | Rat | 3.8 |
| A2 | Human | 7.6 |
|  | Mouse | ND |
|  | Rat | 9.0 |
| A3 | Human | 7.7 |
|  | Mouse | ND |
|  | Rat | 5.4 |
| A4 | Human | 18 |
|  | Mouse | ND |
|  | Rat | 9.5 |
| B1 | Human | 1.0 |
|  | Mouse | 0.75 |
|  | Rat | 0.79 |
| B2 | Human | 1.8 |
|  | Mouse | 3.4 |
|  | Rat | 11 |
| B3 | Human | 4.7 |
|  | Mouse | 5.3 |
|  | Rat | 14 |
| B4 | Human | 0.5 |
|  | Mouse | ND |
|  | Rat | 0.4 |
| C1 | Human | 0.55 |
|  | Mouse | 0.42 |
|  | Rat | 0.7 |
| D1 | Human | 1.6 |
|  | Mouse | ND |
|  | Rat | 2.1 |
| D2 | Human | 14 |
|  | Mouse | ND |
|  | Rat | 11 |
| D3 | Human | 24.5 |
|  | Mouse | ND |
|  | Rat | 0.4 |
| D4 | Human | 6.0 |
|  | Mouse | ND |
|  | Rat | 4.1 |
| D5 | Human | 1.5 |
|  | Mouse | 1.7 |
|  | Rat | 0.84 |
| D6 | Human | 1.2 |
|  | Mouse | ND |
|  | Rat | 0.86 |
| D7 | Human | 6.0 |
|  | Mouse | ND |
|  | Rat | 2.2 |
| D8 | Human | 6.0 |
|  | Mouse | ND |
|  | Rat | 31 |
| D9 | Human | 3.0 |
|  | Mouse | ND |
|  | Rat | 0.54 |
| D10 | Human | 7.3 |
|  | Mouse | ND |
|  | Rat | 2.6 |
| D11 | Human | 1.1 |
|  | Mouse | ND |
|  | Rat | 0.5 |
| D12 | Human | 1.2 |
|  | Mouse | ND |
|  | Rat | 0.8 |
| D13 | Human | 38 |
|  | Mouse | ND |
|  | Rat | 16 |

TABLE 1-continued

K$_i$ for GnRH Agents: Inhibition Binding of $^{125}$I-GnRH-A to GnRH Receptors of Various Species

| Example No. | GnRH Receptor | K$_i$ (nM) |
|---|---|---|
| D14 | Human | 3.5 |
|  | Mouse | ND |
|  | Rat | 0.4 |
| D15 | Human | 3.5 |
|  | Mouse | ND |
|  | Rat | 2.4 |
| D16 | Human | 6.5 |
|  | Mouse | ND |
|  | Rat | 1.1 |
| D17 | Human | 0.65 |
|  | Mouse | ND |
|  | Rat | 0.2 |
| D18 | Human | 0.97 |
|  | Mouse | ND |
|  | Rat | 0.3 |
| D19 | Human | 8.7 |
|  | Mouse | ND |
|  | Rat | 1.9 |
| D20 | Human | 1.0 |
|  | Mouse | ND |
|  | Rat | 0.5 |
| D21 | Human | 3.3 |
|  | Mouse | ND |
|  | Rat | 1.3 |
| D22 | Human | 0.96 |
|  | Mouse | ND |
|  | Rat | 0.3 |
| D23 | Human | 1.6 |
|  | Mouse | 1.7 |
|  | Rat | 0.92 |
| D24 | Human | 360 |
|  | Mouse | ND |
|  | Rat | ND |
| D25 | Human | 460 |
|  | Mouse | ND |
|  | Rat | ND |
| D26 | Human | 84 |
|  | Mouse | ND |
|  | Rat | ND |
| D27 | Human | 250 |
|  | Mouse | ND |
|  | Rat | ND |
| D28 | Human | 30 |
|  | Mouse | ND |
|  | Rat | ND |
| D29 | Human | 54 |
|  | Mouse | ND |
|  | Rat | ND |
| D30 | Human | 46 |
|  | Mouse | ND |
|  | Rat | ND |
| D31 | Human | 6705 |
|  | Mouse | ND |
|  | Rat | ND |
| D32 | Human | 22 |
|  | Mouse | ND |
|  | Rat | ND |
| D33 | Human | 46 |
|  | Mouse | ND |
|  | Rat | ND |
| D34 | Human | 14 |
|  | Mouse | ND |
|  | Rat | ND |
| D35 | Human | 2.6 |
|  | Mouse | ND |
|  | Rat | ND |
| D36 | Human | 87 |
|  | Mouse | ND |
|  | Rat | ND |
| D37 | Human | 41 |
|  | Mouse | ND |
|  | Rat | ND |
| D38 | Human | 22 |
|  | Mouse | ND |
|  | Rat | 15 |
| D39 | Human | 19 |
|  | Mouse | ND |
|  | Rat | 5.4 |
| D40 | Human | 27 |
|  | Mouse | ND |
|  | Rat | 30 |
| D41 | Human | 12 |
|  | Mouse | ND |
|  | Rat | 15 |
| D42 | Human | 1.6 |
|  | Mouse | ND |
|  | Rat | 0.64 |
| D43 | Human | 160 |
|  | Mouse | ND |
|  | Rat | ND |
| D44 | Human | 8.6 |
|  | Mouse | ND |
|  | Rat | 3.4 |
| D45 | Human | 200 |
|  | Mouse | ND |
|  | Rat | ND |
| D46 | Human | 19 |
|  | Mouse | ND |
|  | Rat | ND |
| D47 | Human | 79 |
|  | Mouse | ND |
|  | Rat | ND |
| D48 | Human | 240 |
|  | Mouse | ND |
|  | Rat | ND |
| D49 | Human | 36 |
|  | Mouse | ND |
|  | Rat | 45 |
| D50 | Human | 24 |
|  | Mouse | ND |
|  | Rat | 19 |
| D51 | Human | 202 |
|  | Mouse | ND |
|  | Rat | ND |
| D52 | Human | 260 |
|  | Mouse | ND |
|  | Rat | ND |
| D53 | Human | 4.8 |
|  | Mouse | ND |
|  | Rat | 2.6 |
| D54 | Human | 150 |
|  | Mouse | ND |
|  | Rat | ND |
| D55 | Human | 160 |
|  | Mouse | ND |
|  | Rat | ND |
| D56 | Human | 30 |
|  | Mouse | ND |
|  | Rat | 14 |
| D57 | Human | 36 |
|  | Mouse | ND |
|  | Rat | 4.4 |
| D58 | Human | 4.8 |
|  | Mouse | ND |
|  | Rat | 3.1 |
| D59 | Human | 42 |
|  | Mouse | ND |
|  | Rat | 14 |
| D60 | Human | 1.0 |
|  | Mouse | ND |
|  | Rat | 0.32 |
| D61 | Human | 500 |
|  | Mouse | ND |
|  | Rat | ND |

TABLE 1-continued

$K_i$ for GnRH Agents: Inhibition Binding of $^{125}$I-GnRH-A to GnRH Receptors of Various Species

| Example No. | GnRH Receptor | $K_i$ (nM) |
|---|---|---|
| D62 | Human | 120 |
| | Mouse | ND |
| | Rat | ND |
| D63 | Human | 1.8 |
| | Mouse | ND |
| | Rat | ND |
| D64 | Human | 21 |
| | Mouse | ND |
| | Rat | ND |
| D65 | Human | 6.7 |
| | Mouse | ND |
| | Rat | ND |
| D66 | Human | 5.1 |
| | Mouse | ND |
| | Rat | ND |
| D67 | Human | ND |
| | Mouse | ND |
| | Rat | ND |
| D68 | Human | ND |
| | Mouse | ND |
| | Rat | ND |
| D69 | Human | ND |
| | Mouse | ND |
| | Rat | ND |
| D70 | Human | ND |
| | Mouse | ND |
| | Rat | ND |
| D71 | Human | ND |
| | Mouse | ND |
| | Rat | ND |
| D72 | Human | ND |
| | Mouse | ND |
| | Rat | ND |
| D73 | Human | 4.0 |
| | Mouse | ND |
| | Rat | 2.6 |
| D74 | Human | 3.0 |
| | Mouse | ND |
| | Rat | 1.1 |
| E1 | Human | 3.4 |
| | Mouse | ND |
| | Rat | 7.0 |
| F1 | Human | 0.91 |
| | Mouse | ND |
| | Rat | 0.35 |
| F2 | Human | 1.3 |
| | Mouse | ND |
| | Rat | 1.7 |
| G1 | Human | 1.7 |
| | Mouse | ND |
| | Rat | 0.9 |
| H1 | Human | 50 |
| | Mouse | ND |
| | Rat | ND |
| H2 | Human | 47 |
| | Mouse | ND |
| | Rat | ND |
| H3 | Human | 46 |
| | Mouse | ND |
| | Rat | ND |
| H4 | Human | 13 |
| | Mouse | ND |
| | Rat | 16 |
| H5 | Human | 11 |
| | Mouse | ND |
| | Rat | 8.2 |
| H6 | Human | 12 |
| | Mouse | ND |
| | Rat | 12 |
| I1 | Human | 27 |
| | Mouse | ND |
| | Rat | 26 |
| I2 | Human | 24 |
| | Mouse | ND |
| | Rat | 16 |
| I3 | Human | 36 |
| | Mouse | ND |
| | Rat | 22 |
| J1 | Human | 0.2 |
| | Mouse | ND |
| | Rat | ND |
| K1 | Human | ND |
| | Mouse | ND |
| | Rat | ND |
| K2 | Human | ND |
| | Mouse | ND |
| | Rat | ND |

ND = not determined

In Vitro Metabolism:

Human, rat, dog, and monkey liver microsomes were isolated by differential centrifugation. Specimens of human liver were obtained from the International Institute for the Advancement of Medicine (Scranton, Pa.). The disappearance of the parent compound was studied in a mixture containing 5 uM compound, 0.5 mg/ml microsomal protein, and 2 mM NADPH in 50 mM K phosphate buffer, pH 7.4. Samples were incubated for 30 minutes at 37° C. The reaction was terminated by the addition of acetonitrile and compounds analyzed by LC-MS as described above. Results are shown in Table 2 below.

TABLE 2

| Ex. No. | Human % rem. 30' | Male Rat (MR) % rem. 30' | MR $T_{1/2}$ hr | MR $C_{max}$ $\mu M$ | MR $T_{max}$ hr | MR $F_{p.o.}$ | Fem. Rat (FR) % rem. 30' | FR $T_{1/2}$ hr | FR $C_{max}$ $\mu M$ | FR $T_{max}$ hr | FR $F_{p.o.}$ | Rat plasma % remain | Dog % rem. 30' | Monkey % rem. 30' | HSA column $\alpha$ | Solubility $\mu g/ml$ pH2 | Solubility $\mu g/ml$ pH6 |
|---|---|---|---|---|---|---|---|---|---|---|---|---|---|---|---|---|---|
| A1 | 60 | 11 | 1.5 | 0.1 | 1 | 6%[1] | 74 | 5.1 | 1.4 | 1 | 37%[4] | 100 | 22 | 0 | 1 | >12 | >12 |
| B1 | 54 | 1 | ND | ND | ND | ND | 94 | ND | ND | ND | ND | 100 | 2 | 0 | ND | 1.2 | 0.4 |
| C1 | 35 | 1 | ND | ND | ND | ND | 72 | 2 | 0.8 | 2 | 56%[5] | 100 | 0 | 0 | 13 | ND | 1 |
| B2 | 40 | 11 | ND | ND | ND | ND | 35 | 5.7 | 0.9 | 1 | 10%[6] | 83 | 4 | 12 | >30 | ND | 0.4 |
| D3 | 52 | 22 | ND | ND | ND | ND | 84 | 1.6 | 0.4 | 0.5 | 5%[5] | ND | 13 | 1 | 30 | ND | 2.5 |
| D1 | 82 | 20 | ND | ND | ND | ND | 81 | 1.2 | 0.1 | 1 | 2%[5] | 100 | 52 | 22 | 8 | ND | >15 |
| D2 | 76 | 19 | ND | ND | ND | ND | 84 | ND | ND | ND | ND | ND | 35 | 19 | 4 | ND | 0.3 |

TABLE 2-continued

| Ex. No. | Human % rem. 30' | Male Rat (MR) % rem. 30' | MR $T_{1/2}$ hr | MR $C_{max}$ $\mu M$ | MR $T_{max}$ hr | MR $F_{p.o.}$ | Fem. Rat (FR) % rem. 30' | FR $T_{1/2}$ hr | FR $C_{max}$ $\mu M$ | FR $T_{max}$ hr | FR $F_{p.o.}$ | Rat plasma % remain | Dog % rem. 30' | Monkey % rem. | H S A column $\alpha$ | Solubility $\mu g/ml$ pH2 | pH6 |
|---|---|---|---|---|---|---|---|---|---|---|---|---|---|---|---|---|---|
| A3 | 83 | 44 | ND | 3.2 | 1 | **2 | 75 | 2.2 | 4 | 1 | 60%5 | 100 | 49 | 7 | 0.4 | ND | >15 |
| D2 | 83 | 53 | ND | ND | ND | ND | 82 | ND | ND | ND | ND | ND | 9 | 6 | >10 | ND | 0.1 |
| E1 | 48 | 12 | ND | ND | ND | ND | 76 | ND | ND | ND | ND | ND | 28 | 0 | ND | ND | 2 |
| B4 | 38 | 38 | ND | ND | ND | ND | 100 | ND | ND | ND | ND | ND | 26 | 0 | ND | ND | 2.5 |
| D3 | 89 | 22 | ND | ND | ND | ND | 63 | 2.3 | 0.2 | 2 | 28%5 | 100 | 25 | 0 | 2 | ND | >15 |
| F1 | 39 | 36 | ND | ND | ND | ND | 81 | ND | ND | ND | ND | ND | 31 | 0 | ND | ND | 12 |
| F2 | 70 | 74 | ND | ND | ND | ND | 100 | ND | ND | ND | ND | 100 | 85 | 2 | ND | ND | ND |
| G1 | 79 | 80 | ND | ND | ND | ND | 92 | 4.1 | 0.2 | 2 | 10%5 | 92 | 70 | 0 | >30 | ND | ND |
| D4 | 83 | 38 | ND | ND | ND | ND | 76 | ND | ND | ND | ND | ND | 34 | 2 | ND | ND | ND |
| D5 | 80 | 79 | 7 | 0.7 | 4 | 34% | 95 | ND | ND | ND | ND | ND | 98 | 30 | 2 | >30 | >30 |
| D6 | 77 | 74 | ND | ND | ND | ND | 90 | ND | ND | ND | ND | ND | 77 | 8 | ND | ND | ND |
| D7 | 91 | 91 | ND | ND | ND | ND | 95 | 4.1 | 0.5 | 2 | 30%5 | 100 | 91 | 16 | 2 | ND | ND |
| D8 | 73 | 58 | ND | ND | ND | ND | 84 | ND | ND | ND | ND | 100 | 49 | 4 | 3 | ND | ND |
| D9 | 89 | 80 | ND | ND | ND | ND | 100 | 4.3 | 0.8 | 2 | 57%5 | 100 | 100 | 44 | 2 | ND | ND |
| D10 | 77 | 66 | ND | ND | ND | ND | 79 | ND | ND | ND | ND | ND | 66 | 28 | ND | ND | ND |
| D12 | 81 | 54 | ND | ND | ND | ND | 80 | ND | ND | ND | ND | ND | 59 | 37 | ND | >30 | >30 |
| D11 | 62 | 42 | ND | ND | ND | ND | 56 | ND | ND | ND | ND | ND | 56 | 20 | ND | ND | ND |
| D14 | 86 | 78 | ND | ND | ND | ND | 90 | ND | ND | ND | ND | ND | 98 | 63 | ND | ND | ND |
| D16 | 76 | 34 | ND | ND | ND | ND | 95 | ND | ND | ND | ND | ND | 97 | 66 | ND | ND | ND |
| D17 | 45 | 23 | ND | ND | ND | ND | 24 | ND | ND | ND | ND | ND | 29 | 42 | 10 | ND | ND |
| D18 | 82 | 74 | ND | ND | ND | ND | 97 | ND | ND | ND | ND | ND | 84 | 80 | ND | ND | ND |
| D21 | 89 | 87 | ND | ND | ND | ND | 89 | ND | ND | ND | ND | ND | 67 | 85 | ND | ND | ND |
| D22 | 66 | 69 | ND | ND | ND | ND | 94 | ND | ND | ND | ND | ND | 87 | 5 | ND | ND | ND |
| D23 | 80 | 79 | 7 | 0.7 | 4 | 34% | 95 | ND | ND | ND | ND | ND | 98 | 30 | 2 | >30 | >30 |

Notes:
[1] 10 mg/kg as 5 mg/ml solution in 10% DMSO, 20% Labrasol, 70% saline
[2] 20 mg/kg as 10 mg/ml in Labrasol/H2O 1/1 (Cmax ~3.7 $\mu M$, Tmax ~0.5 hr as 50 mg/kg in 50 mg/ml PG;
[3] 20 mg/kg as 20 mg/ml suspension in 0.5% CMC
[4] 10 mg/kg as 5 mg/ml solution in 10% DMSO 20% Labrasol, 70% saline (Fpo 87% in 10% DMSO, 20% cremophor, 70% saline)
[5] 10 mg/kg as 5 mg/ml solution in 10% DMSO, 10% cremophor, 80% saline
[6] 6 mg/kg as 3 mg/ml solution in 6% DMSO, 6% cremophor, 88% saline In Vivo Tests Animal Models to Assess Activities of GnRH Antagonists;

Model# 1: Castrated Male Rat Model.

The castrated male rat is a sensitive and specific model for evaluating GnRH antagonists (Heber, 1982; Puente, 1986)). Removal of the testes produces a model with GnRH-mediated elevations of circulating LH. This mechanism of action of the hypothalamic-pituitary-gonadal axis is well-defined (Ellis and Desjardins, 1984). Suppression of LH in this model following administration of a GnRH antagonist reflects blockade of the GnRH receptor.

Vehicle or test compound D23 was administered at 5.0, 25, 50 and 75 mg/kg by oral gavage. Test compound was formulated as a 0.5% carboxymethylcellulose suspension. Blood samples (400 $\mu L$) were drawn into heparin-containing tubes at multiple time points post treatment. Blood was centrifuged immediately, and plasma collected and stored in −20° freezer until assayed.

Model # 2: Intact Male Rat Model.

Testosterone is a hormone regulated by the hypothalamic-pituitary-gonadal axis. GnRH is secreted in pulses from the hypothalamus and stimulates the anterior pituitary gland to release the gonadotropic hormones luteinizing hormone (LH) and follicle stimulating hormone (FSH). Testosterone is produced when the testes are stimulated by LH. A GnRH antagonist is expected to reduce testosterone levels by inhibiting GnRH stimulation of LH release.

Vehicle or test compound D23 was administered at 5.0, 25, 50 and 75 mg/kg by oral gavage. Test compound was formulated as a 0.5% carboxymethylcellulose suspension. Blood samples (400 $\mu L$) were drawn into heparin-containing tubes at multiple time points post treatment. Blood was centrifuged immediately, and plasma collected and stored in −20° freezer until assayed.

Pharmaceutical Compositions

The exemplary compounds described above may be formulated into pharmaceutical compositions according to the following general examples.

Parenteral Composition:

To prepare a parenteral pharmaceutical composition suitable for administration by injection, 100 mg of a water-soluble salt of a compound of the Formula I or II is dissolved in DMSO and then mixed with 10 mL of 0.9% sterile saline. The mixture is incorporated into a dosage unit form suitable for administration by injection.

Oral Composition:

To prepare a pharmaceutical composition for oral delivery, 100 mg of a compound of Formula I or II is mixed with 750 mg of lactose. The mixture is incorporated into an oral dosage unit for, such as a hard gelatin capsule, which is suitable for oral administration.

Intraocular Composition:

To prepare a sustained-release pharmaceutical composition for intraocular delivery, a compound of Formula I or II is suspended in a neutral, isotonic solution of hyaluronic acid (1.5% conc.) in a phosphate buffer (pH 7.4) to form a 1% suspension, which is suitable for intraocular administration.

It is to be understood that the foregoing description is exemplary and explanatory in nature, and is intended to illustrate the invention and its preferred embodiments. Thus, the scope of the invention should be understood to be defined not by the foregoing description, but by the following claims and their equivalents.

What is claimed is:

1. A compound of Formula I:

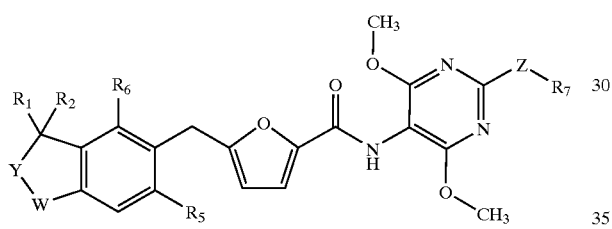

(I)

wherein:

Y is O or $(CH_2)_n$ where n is 1 or 2;

$R_1$ and $R_2$ are each independently: hydrogen; =O; or a halogen; or an alkyl, alkenyl, heteroalkyl, haloalkyl, alkynyl, aryl, cycloalkyl, heterocycloalkyl, or heteroaryl group unsubstituted or substituted with one or more substituents independently selected from the group consisting of halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents independently selected from the group consisting of halogens, =O, —NO$_2$, —CN, —(CH$_2$)$_z$—CN where z is an integer from 0 to 4, —OR$_c$, —NR$_c$OR$_c$, —NR$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyls, unsubstituted alkenyls, unsubstituted alkynyls, unsubstituted aryls, unsubstituted cycloalkyls, unsubstituted heterocycloalkyls, and unsubstituted heteroaryls, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

W is O or C(R$_3$)(R$_4$), where R$_3$ and R$_4$ are each independently selected from the group consisting of hydrogen; =O; and halogens; and alkyl, alkenyl, heteroalkyl, haloalkyl, alkynyl, aryl, cycloalkyl, heterocycloalkyl, and heteroaryl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —C(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

$R_5$ is hydrogen, halogen, unsubstituted $C_1$–$C_3$ alkyl, or unsubstituted $C_1$–$C_3$ heteroalkyl;

$R_6$ is hydrogen, halogen, unsubstituted $C_1$–$C_3$ alkyl, or unsubstituted $C_1$–$C_3$ heteroalkyl;

Z is O or $NR_x$, where $R_x$ is hydrogen, unsubstituted alkyl, or unsubstituted heteroalkyl; and $R_7$ is hydrogen; a halogen; or an alkyl, alkenyl, heteroalkyl, haloalkyl, alkynyl, aryl, cycloalkyl, heterocycloalkyl, or heteroaryl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —HR$_c$R$_c$, —C(O)NR$_c$, —C(O)OR$_c$, —C(O)R$_c$, —NR$_c$C(O)NR$_c$R, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

or $R_7$ and $R_x$ cyclize to form a heterocycloalkyl or heteroaryl group unsubstituted or substituted with one or more substituents independently selected from the group consisting of =O; and halogens; and alkyl, alkenyl, heteroalkyl, haloalkyl, alkynyl, aryl, cycloalkyl, heterocycloalkyl, and heteroaryl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group; or a pharmaceutically acceptable salt of said compound.

2. A compound according to claim 1 wherein $R_1$ and $R_2$ are each independently hydrogen; or an alkyl or heteroalkyl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group, and where at least one of $R_1$ or $R_2$ is not hydrogen.

3. A compound according to claim 1 wherein: W is C($R_3$)($R_4$), where $R_3$ and $R_4$ are each independently selected from the group consisting of hydrogen; and alkyl and heteroalkyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

4. A compound according to claim 2 wherein W is C(R$_3$)(R$_4$), where R$_3$ and R$_4$ are each independently selected from the group consisting of hydrogen; and alkyl and heteroalkyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O)H, —NH$_2$, —C(O)NH$_2$, —OC(O)NH$_2$, —NHC(O)H, —NHC(O)OH, —C(O)NHC(O)H, —OS(O)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

5. A compound according to claim 1 wherein: Z is NR$_x$, where R$_x$ is hydrogen, unsubstituted alkyl, or unsubstituted heteroalkyl; or R$_7$ and R$_x$ cyclize to form a heterocycloalkyl unsubstituted or substituted with one or more substituents independently selected from the group consisting of hydrogen; =O; and halogens; alkyl, alkenyl, heteroalkyl, haloalkyl, alkynyl, aryl, cycloalkyl, heterocycloalkyl, heteroaryl unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —S$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, NR$_c$OR$_c$, NR$_c$R$_c$, C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

6. A compound according to claim 1 wherein R$_7$ is an alkyl, alkenyl, heteroalkyl, or an alkynyl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

7. A compound represented by Formula II:

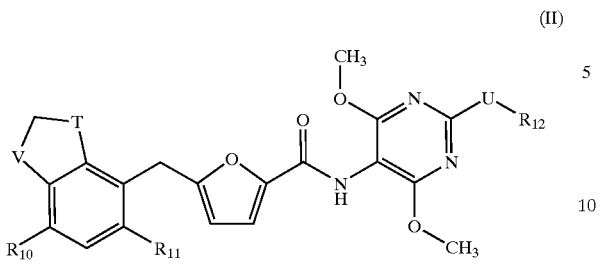

(II)

wherein:

T is O or (CH$_2$)$_n$, where n is 1 or 2;

V is O or C(R$_8$)(R$_9$), where R$_8$ and R$_9$ are each independently selected from the group consisting of hydrogen; =O; and halogens; and alkyl, alkenyl, heteroalkyl, haloalkyl, alkynyl, aryl, cycloalkyl, heterocycloalkyl, and heteroaryl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

R$_{10}$ is hydrogen, halogen, unsubstituted C$_1$–C$_3$ alkyl, or unsubstituted C$_1$–C$_3$ heteroalkyl;

R$_{11}$ is hydrogen, halogen, unsubstituted C$_1$–C$_3$ alkyl, or unsubstituted C$_1$–C$_3$ heteroalkyl;

R$_{12}$ is hydrogen or a halogen, or an alkyl, alkenyl, heteroalkyl, haloalkyl, alkynyl, aryl, cycloalkyl, heterocycloalkyl, or heteroaryl group unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group; and U is O or NR$_x$, where R$_x$ is hydrogen, alkyl, or heteroalkyl;

or R$_{12}$ and R$_x$ cyclize to form a heterocycloalkyl unsubstituted or substituted with one or more substituents independently selected from the group consisting of halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

or a pharmaceutically acceptable salt of said compound.

8. A compound according to claim 7 wherein V is C(R$_8$)(R$_9$), and R$_8$ and R$_9$ are each independently selected from the group consisting of hydrogen and alkyl, alkenyl, heteroalkyl, and alkynyl groups unsubstituted or substituted with one or more substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

9. A compound according to claim 7 wherein: U is NR$_x$, where R$_x$ is hydrogen, unsubstituted alkyl, or unsubstituted heteroalkyl; or R$_{12}$ and R$_x$ cyclize to form a heterocycloalkyl unsubstituted or substituted with one or more substituents independently selected from the group consisting of hydrogen; =O; and halogens; and alkyl, alkenyl, heteroalkyl, haloalkyl, alkynyl, aryl, cycloalkyl, heterocycloalkyl, heteroaryl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$R$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, C(O)R$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

10. A compound according to claim 8 wherein R$_{12}$ is an alkyl, alkenyl, heteroalkyl, or alkynyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S$_2$)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

11. A compound according to claim 10 wherein: U is NH; T is O; V is C(R$_8$)(R$_9$), and R$_8$ and R$_9$ are each independently selected from the group consisting of hydrogen; and alkyl, alkenyl, heteroalkyl, and alkynyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O)NH$_2$, —S(O)NH$_2$, —SNH$_2$, —NHCS(O$_2$)H$_2$, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, NR$_c$R$_c$, C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group.

12. A compound according to claim 10 wherein: U is O; T is O; V is C($R_8$)($R_9$), and $R_8$ and $R_9$ are each independently selected from the group consisting of hydrogen; and alkyl, alkenyl, heteroalkyl, and alkynyl groups unsubstituted or substituted with one or more substituents selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group.

13. A compound according to claim 1 and selected from the group consisting of:

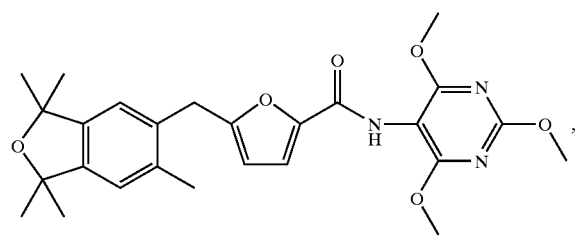

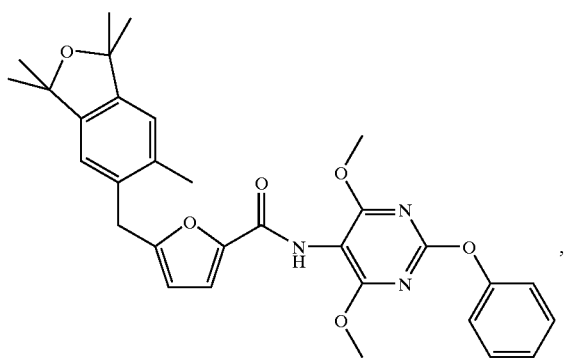

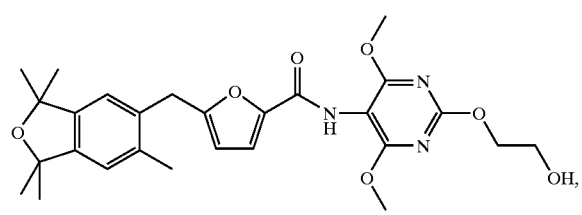

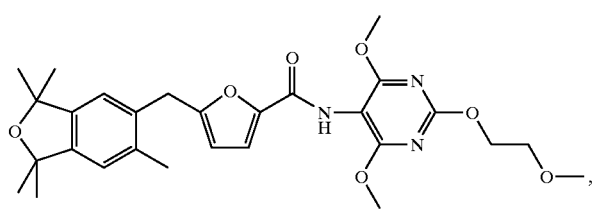

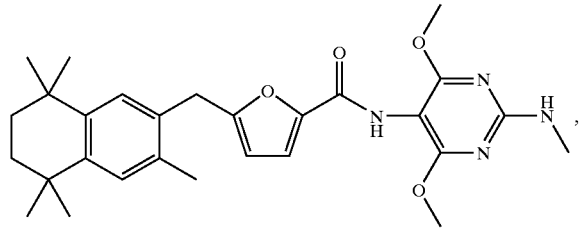

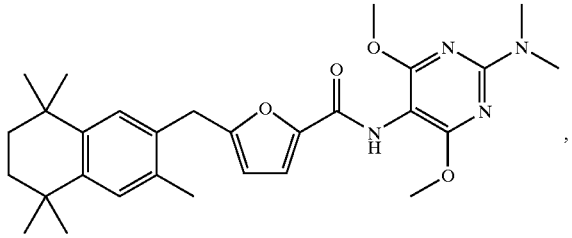

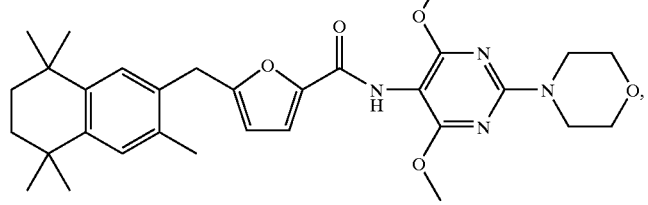

-continued
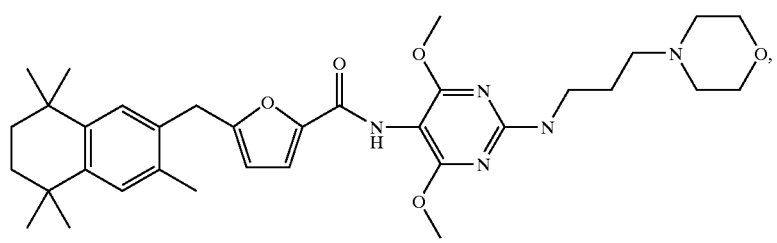
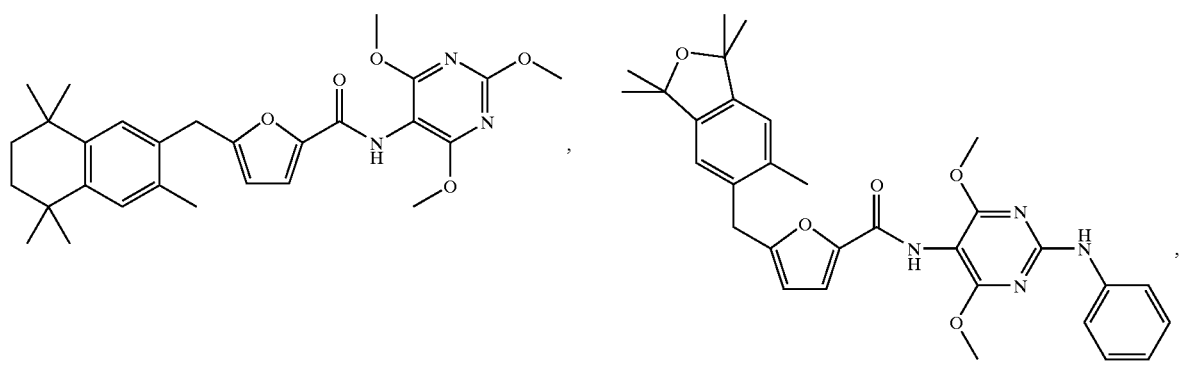
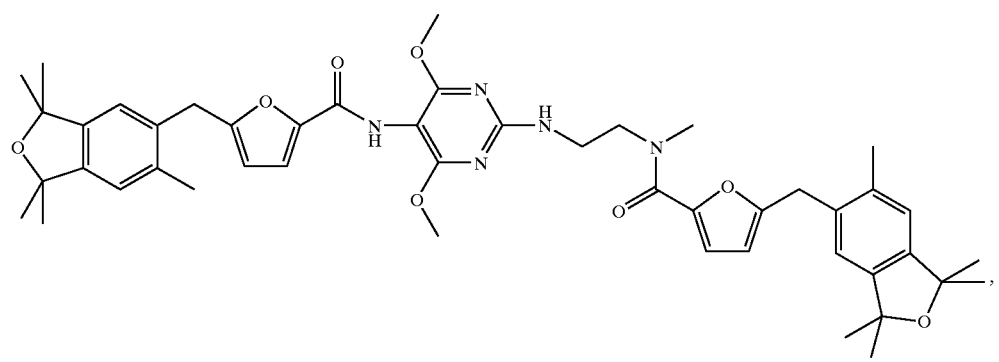
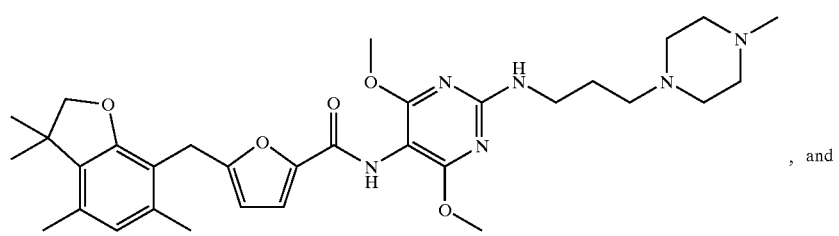
, and
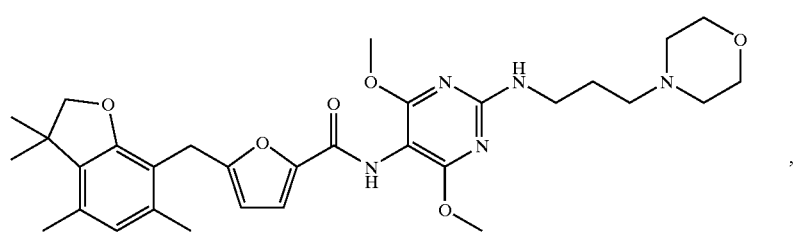
, or a pharmaceutically acceptable salt thereof.
14. A compound according to claim 1 and selected from the group consisting of:
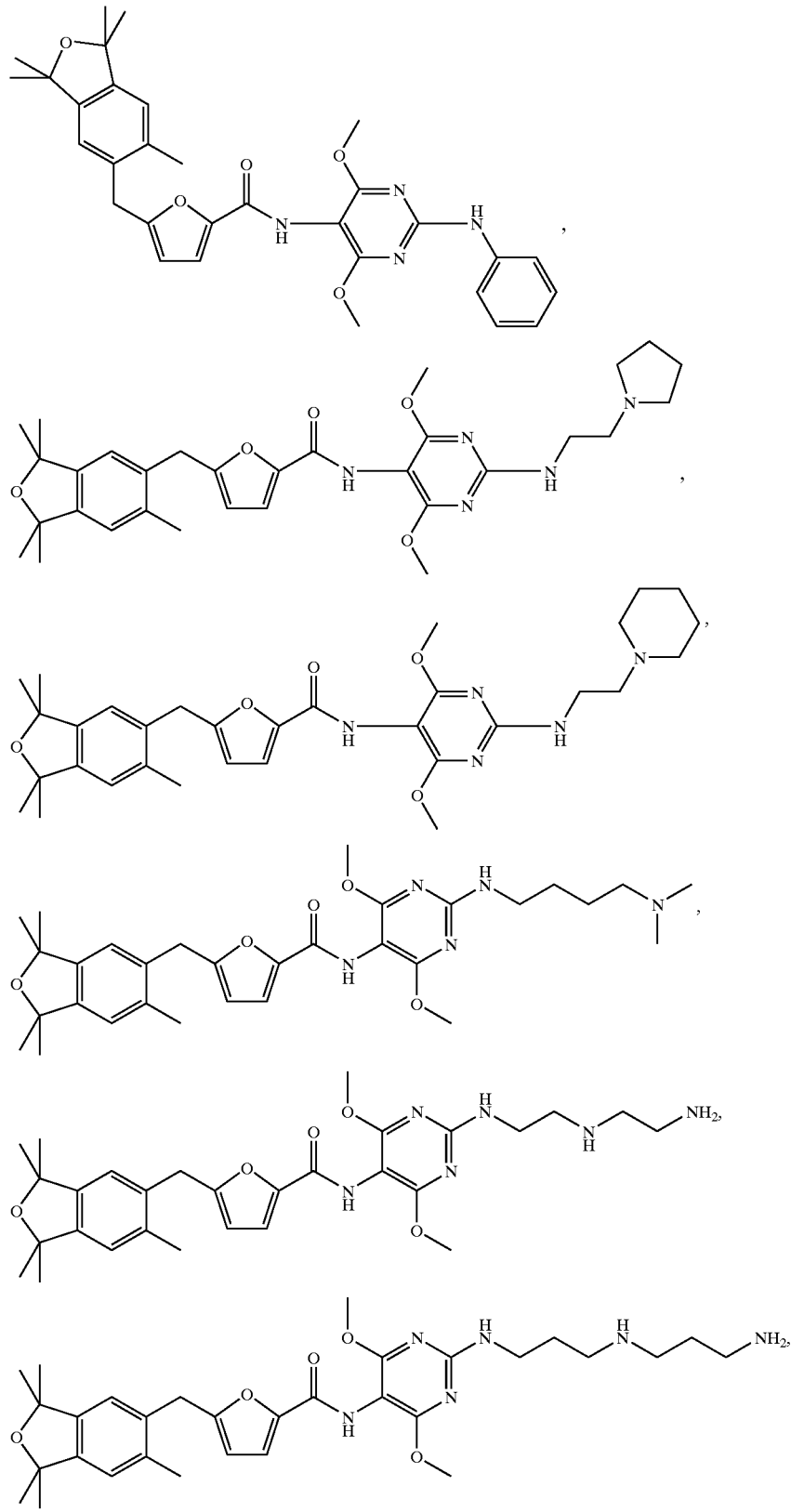

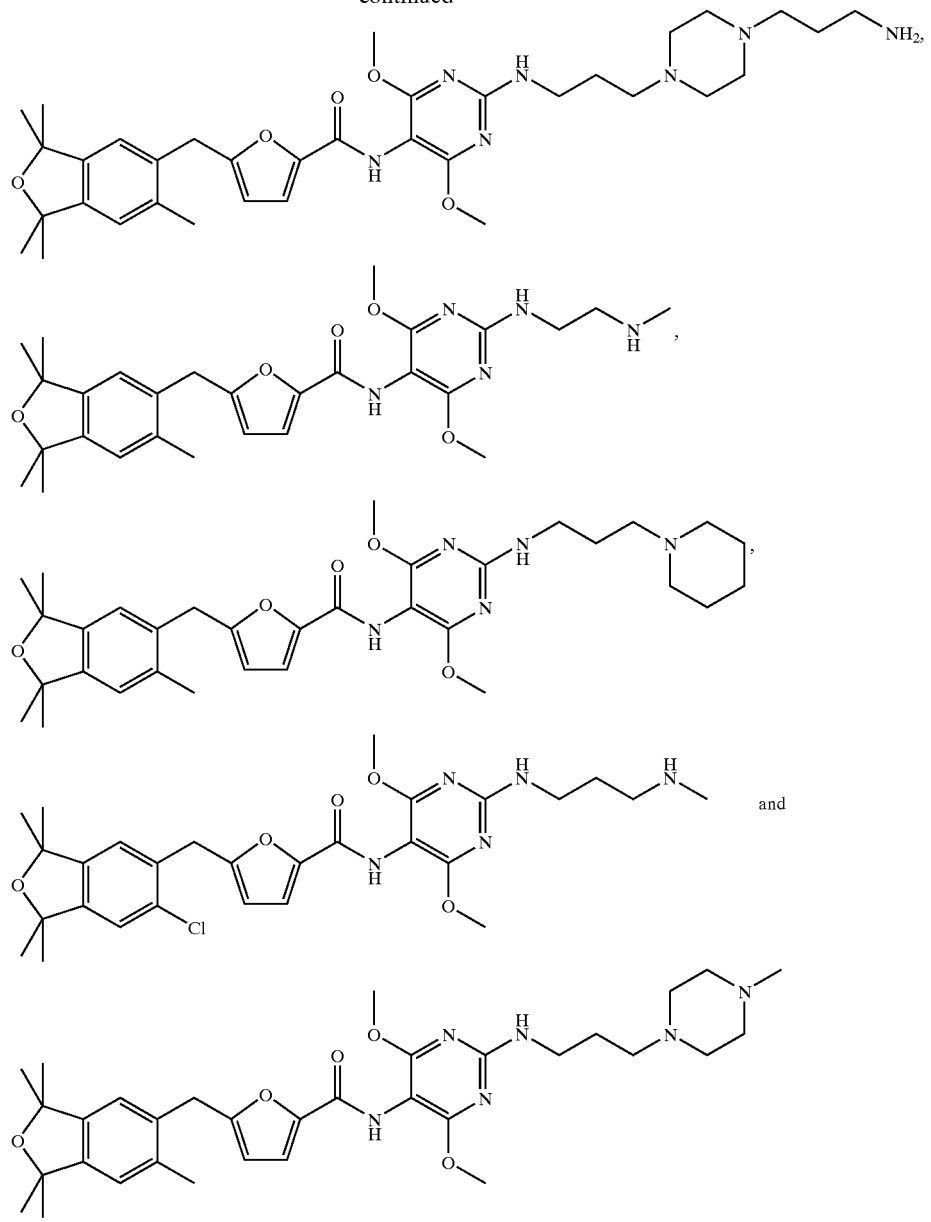
or a pharmaceutically acceptable salt thereof.
15. A pharmaceutical composition comprising: a therapeutically effective amount of an agent selected from the group consisting of compounds as defined in claim 1, 7, 13 or 14; and a pharmaceutically acceptable carrier.
* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: Gonadotropin-Releasing Hormone which plays a
      central role in the biology of reproduction.

<400> SEQUENCE: 1

Glu His Trp Ser Tyr Gly Leu Arg Pro Gly
1               5                   10